(12) United States Patent
Mandelkern et al.

(10) Patent No.: US 11,399,792 B2
(45) Date of Patent: Aug. 2, 2022

(54) METHODS, SYSTEMS, APPARATUSES, AND COMPUTER PROGRAMS FOR PROCESSING TOMOGRAPHIC IMAGES

(71) Applicant: DENTSPLY SIRONA INC., York, PA (US)

(72) Inventors: Stan Mandelkern, Teaneck, NJ (US); Joseph Lasker, Brooklyn, NY (US); Fred Duewer, Milpitas, CA (US)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 16/703,307

(22) Filed: Dec. 4, 2019

(65) Prior Publication Data
US 2020/0107793 A1   Apr. 9, 2020

Related U.S. Application Data

(63) Continuation of application No. 15/510,596, filed as application No. PCT/US2015/050497 on Sep. 16, 2015, now Pat. No. 10,912,530.
(Continued)

(51) Int. Cl.
*A61B 6/00* (2006.01)
*G06T 5/00* (2006.01)
(Continued)

(52) U.S. Cl.
CPC ............ *A61B 6/5217* (2013.01); *A61B 6/025* (2013.01); *A61B 6/027* (2013.01); *A61B 6/145* (2013.01); *A61B 6/463* (2013.01); *A61B 6/466* (2013.01); *A61B 6/467* (2013.01); *A61B 6/469* (2013.01); *A61B 6/5205* (2013.01); *A61B 6/5223* (2013.01); *A61B 6/5235* (2013.01); *A61B 6/5264* (2013.01); *G06T 5/003* (2013.01); *G06T 5/008* (2013.01); *G06T 7/0014* (2013.01);
(Continued)

(58) Field of Classification Search
None
See application file for complete search history.

(56) References Cited

U.S. PATENT DOCUMENTS 6,196,715 B1   3/2001   Nambu
2006/0018526 A1*  1/2006  Avinash .................. G06T 5/003
                                                                382/132
(Continued)

FOREIGN PATENT DOCUMENTS

WO        2013056733 A1      4/2013

OTHER PUBLICATIONS

European Search Report; EP 20153631; dated May 7, 2020 (completed).
(Continued)

*Primary Examiner* — Matthew C Bella
*Assistant Examiner* — Brian D Shin
(74) *Attorney, Agent, or Firm* — Dentsply Sirona Inc.

(57) ABSTRACT

A method, system and computer readable storage media for segmenting individual intra-oral measurements and registering said individual intraoral measurements to eliminate or reduce registration errors. An operator may use a dental camera to scan teeth and a trained deep neural network may automatically detect portions of the input images that can cause registration errors and reduce or eliminate the effect of these sources of registration errors.

18 Claims, 70 Drawing Sheets

Related U.S. Application Data

(60) Provisional application No. 62/214,830, filed on Sep. 4, 2015, provisional application No. 62/076,216, filed on Nov. 6, 2014, provisional application No. 62/050,881, filed on Sep. 16, 2014.

(51) Int. Cl.

| | | |
|---|---|---|
| *G06T 7/00* | (2017.01) | |
| *A61B 6/02* | (2006.01) | |
| *A61B 6/14* | (2006.01) | |
| *G06T 11/00* | (2006.01) | |
| *G06T 7/181* | (2017.01) | |
| *G06T 7/12* | (2017.01) | |
| *G06T 7/136* | (2017.01) | |
| *G06T 7/143* | (2017.01) | |
| *G06T 7/149* | (2017.01) | |
| *G06T 7/246* | (2017.01) | |
| *G06T 7/254* | (2017.01) | |
| *G06T 7/60* | (2017.01) | |

(52) U.S. Cl.
CPC ............... *G06T 7/12* (2017.01); *G06T 7/136* (2017.01); *G06T 7/143* (2017.01); *G06T 7/149* (2017.01); *G06T 7/181* (2017.01); *G06T 7/248* (2017.01); *G06T 7/254* (2017.01); *G06T 7/60* (2013.01); *G06T 11/005* (2013.01); *G06T 11/008* (2013.01); *A61B 6/4085* (2013.01); *G06T 2207/10116* (2013.01); *G06T 2207/20116* (2013.01)

(56) References Cited

U.S. PATENT DOCUMENTS

| | | |
|---|---|---|
| 2010/0215245 A1 | 8/2010 | Olivan |
| 2010/0260393 A1 | 10/2010 | Truyen |
| 2014/0169650 A1 | 6/2014 | Sakimoto |
| 2014/0219534 A1 | 8/2014 | Wiemker |
| 2015/0302615 A1* | 10/2015 | Fukuda ............... G06T 11/006 378/19 |
| 2016/0051215 A1* | 2/2016 | Chen ..................... A61B 6/469 715/771 |

OTHER PUBLICATIONS

Garib et al; "Periodontal effects of rapid maxillary expansion with tooth-tissue-borne and tooth-borne expanders: A computed tomography evaluation"; American Journal of Orthodontics & Dentofacial Orthopedics; Elsevier, Amsterdam, NL; vol. 129, No. 6; Jun. 1, 2006; pp. 749-758.

Adam M Timock et al; "Accuracy and reliability of buccal bone height and thickness measurements from cone-beam computed tomography imaging"; American Journal of Orthodontics and Dentofacial Orthopedics; vol. 140, No. 5; pp. 734-744.

European Office Action dated Dec. 15, 2021.

Ewa Pietka et al; "Computer-Assisted Bone Age Assessment: Image Preprocessing and Epiphyseal/Metaphyseal ROI Extraction"; IEEE Transactions on Medical Imaging; vol. 20, No. 8; Aug. 1, 2001.

European Office Action dated Dec. 13, 2021.

* cited by examiner

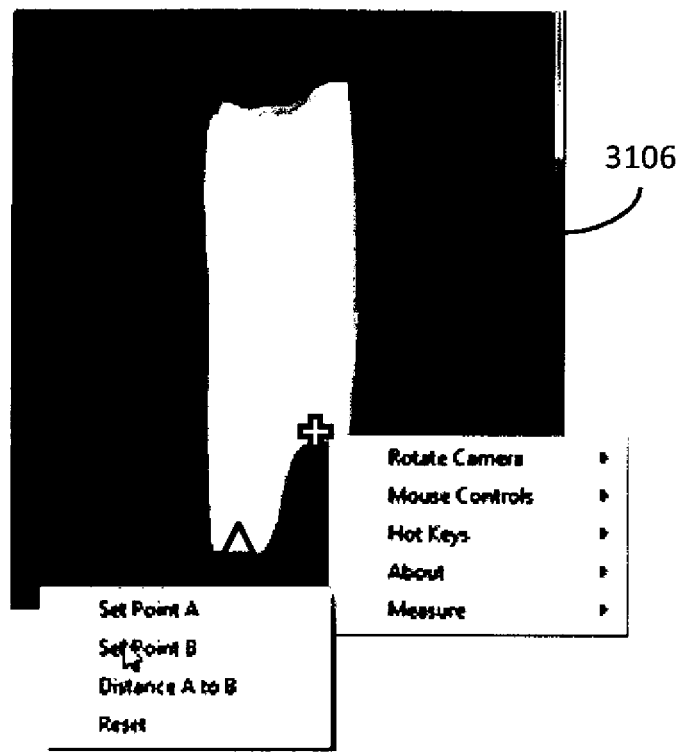
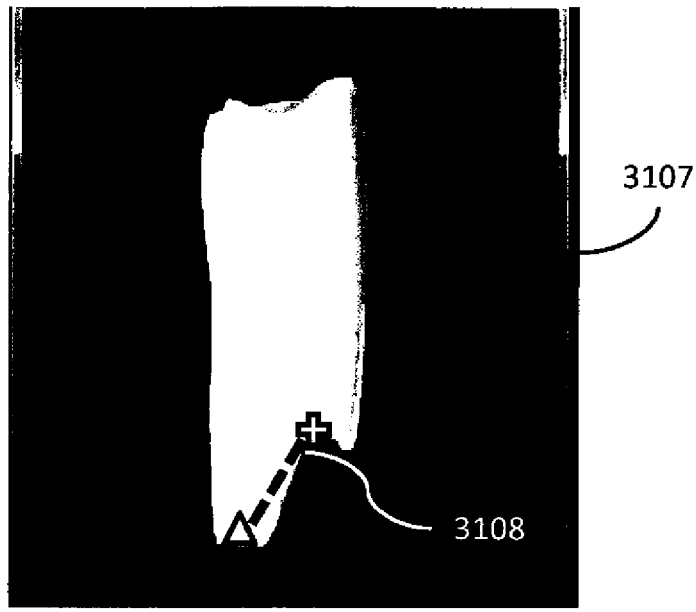
FIG. 31B

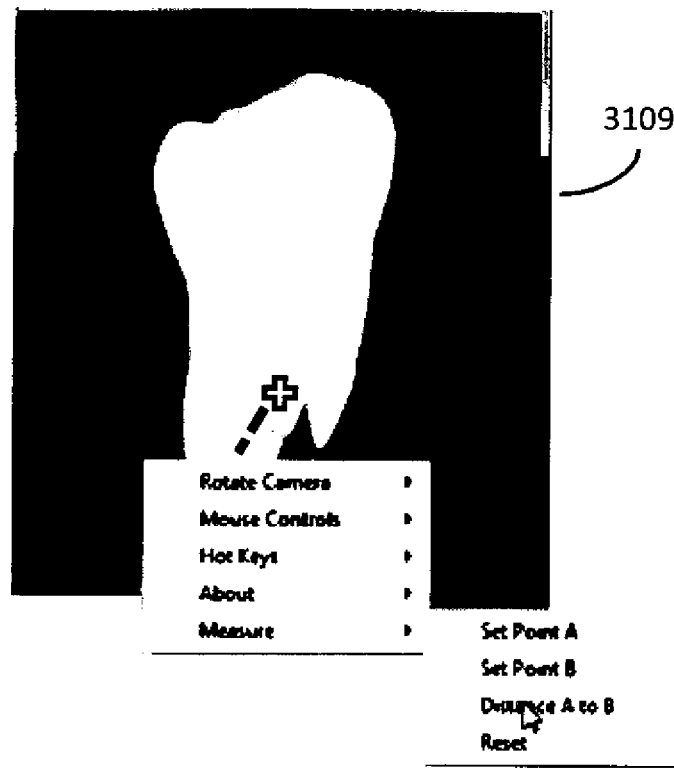
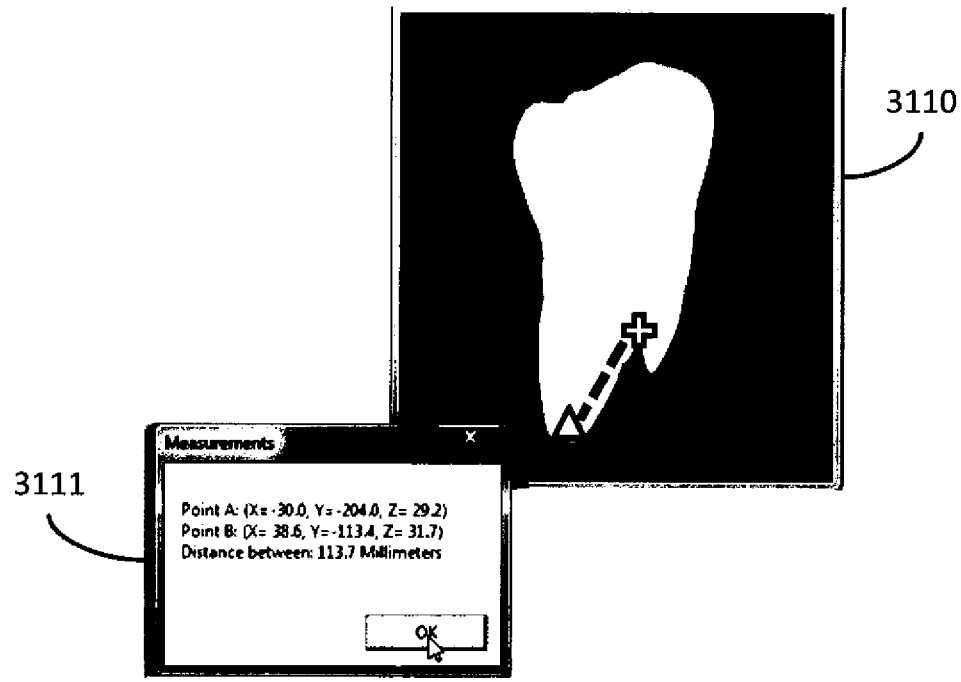
FIG. 31C

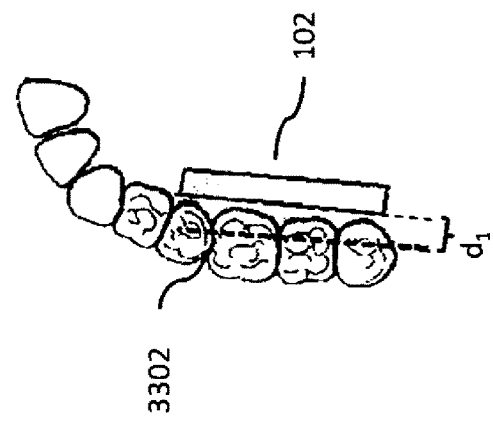
FIG. 33B
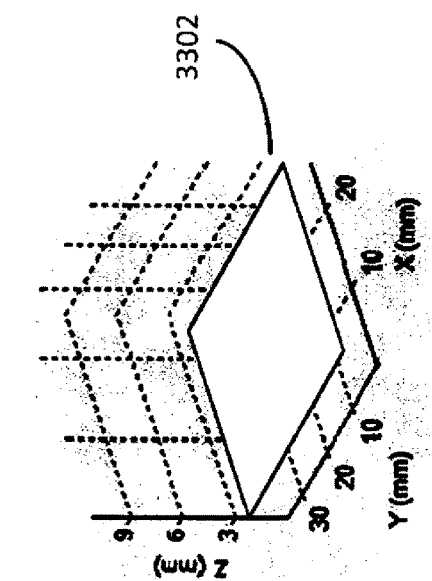
FIG. 33D
FIG. 33A
 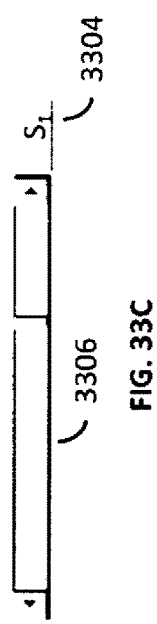
FIG. 33C

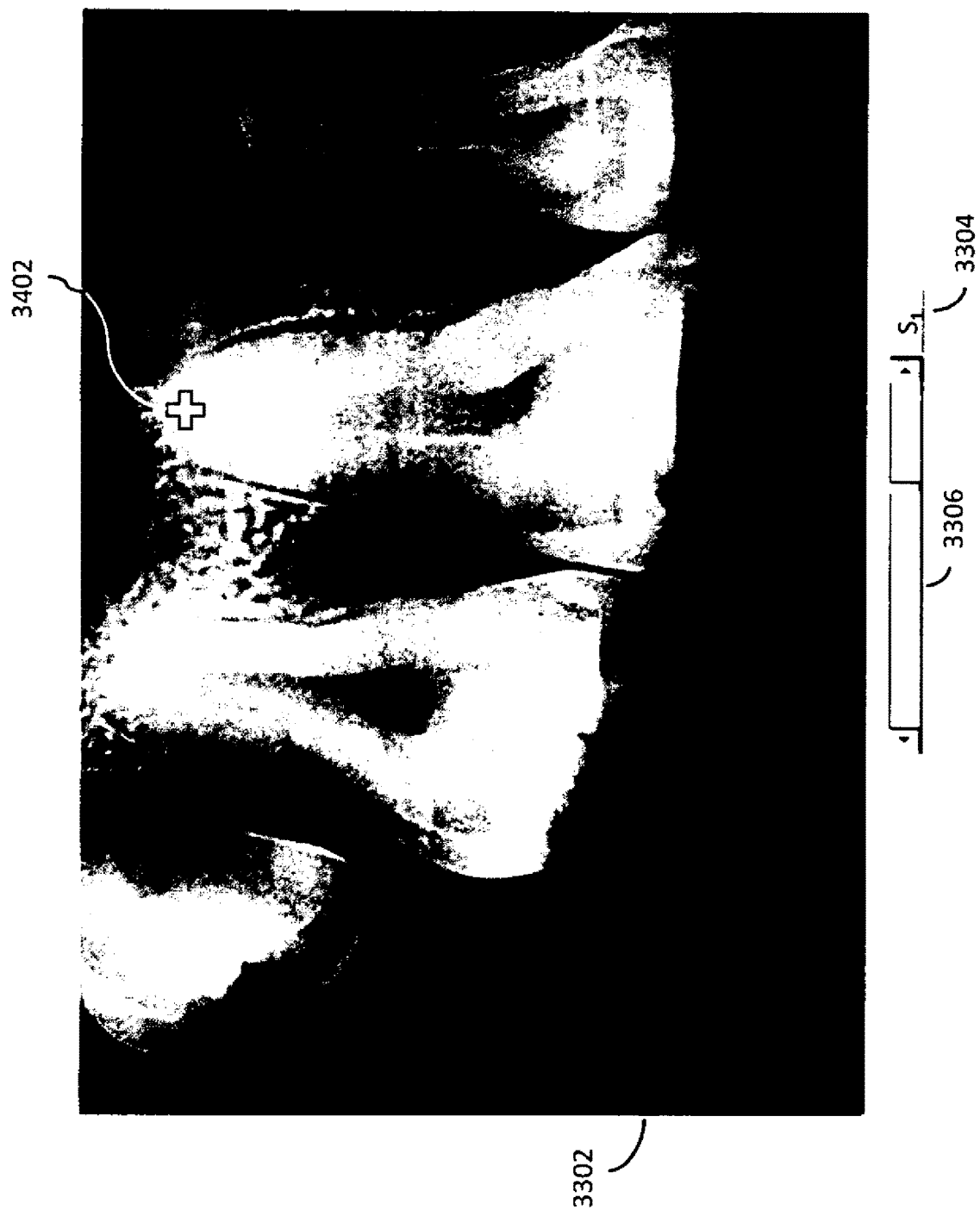

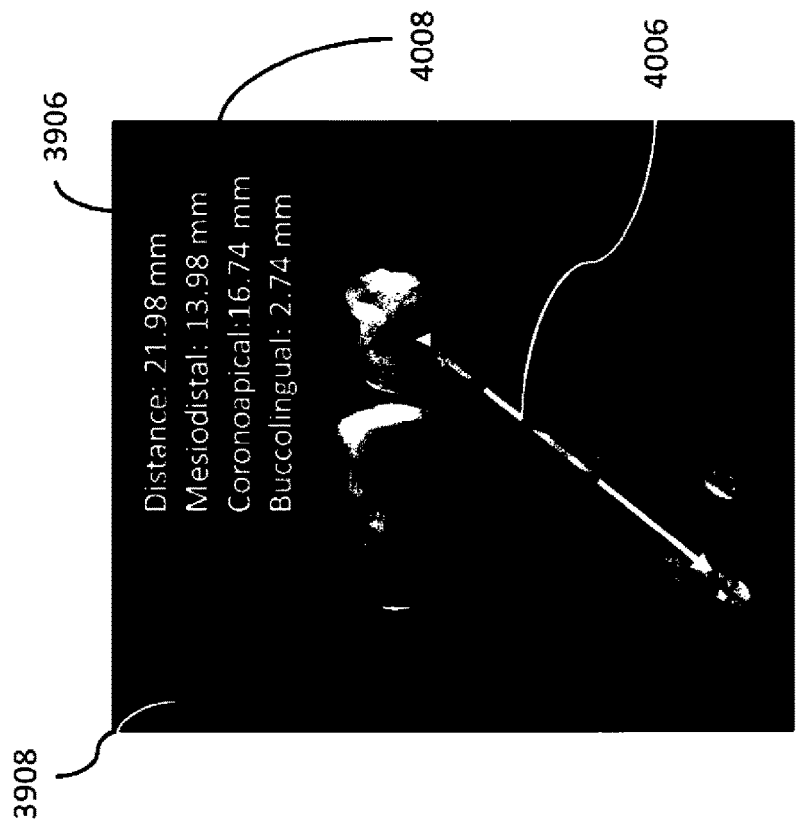
FIG. 40C
FIG. 40A
 
FIG. 40B

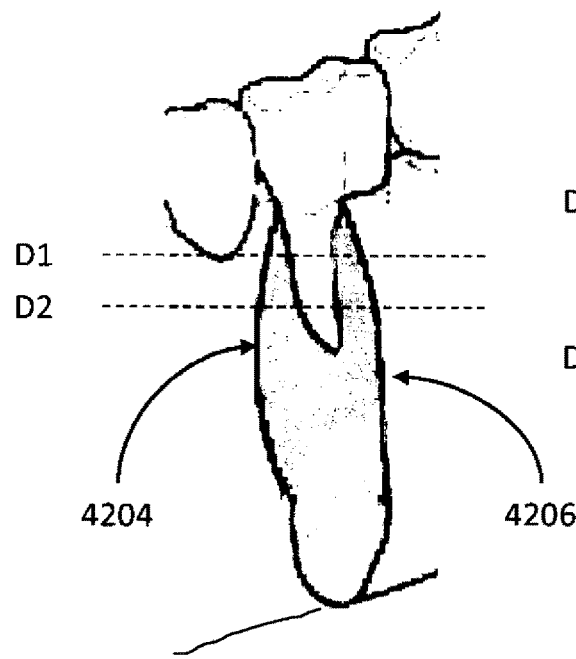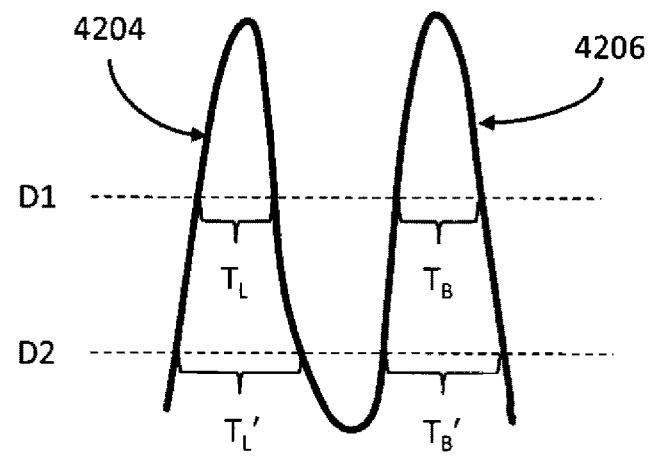
Fig. 53A
Fig. 53B
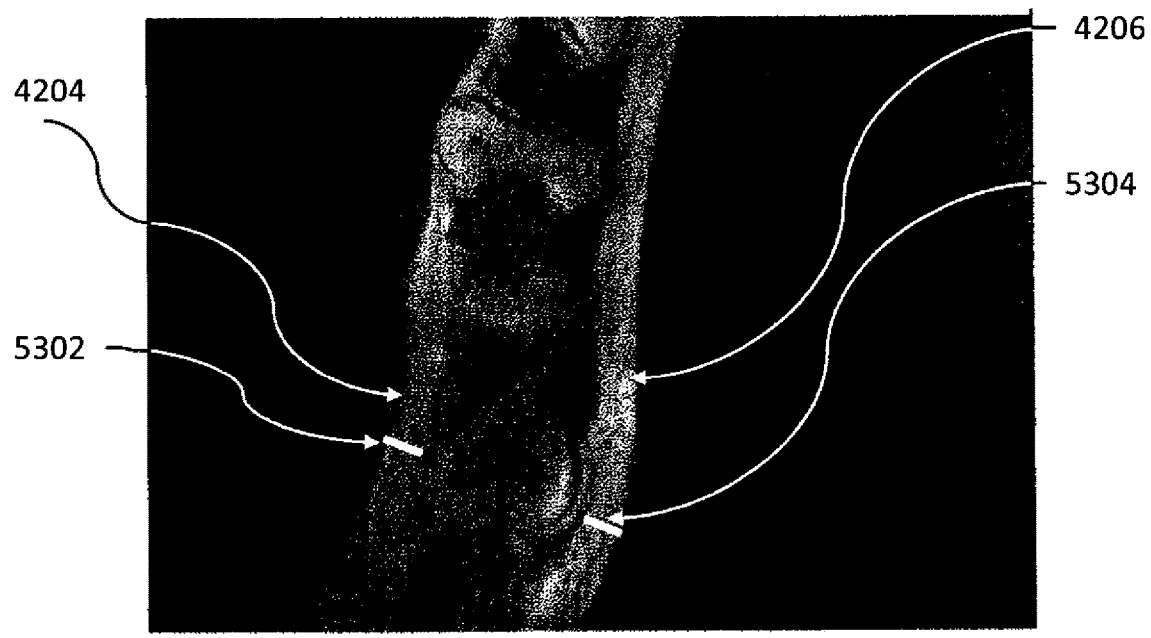
FIG. 53C

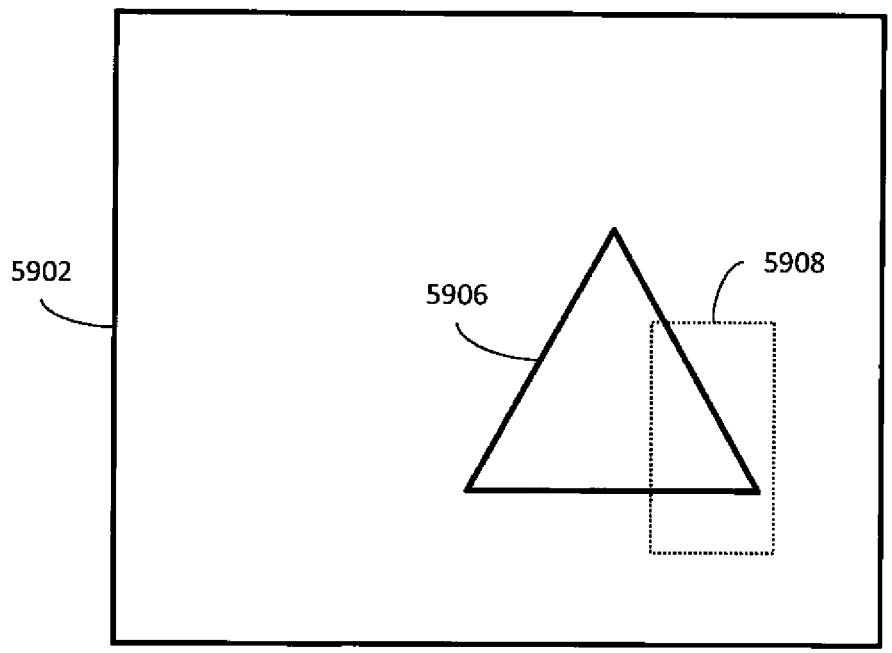
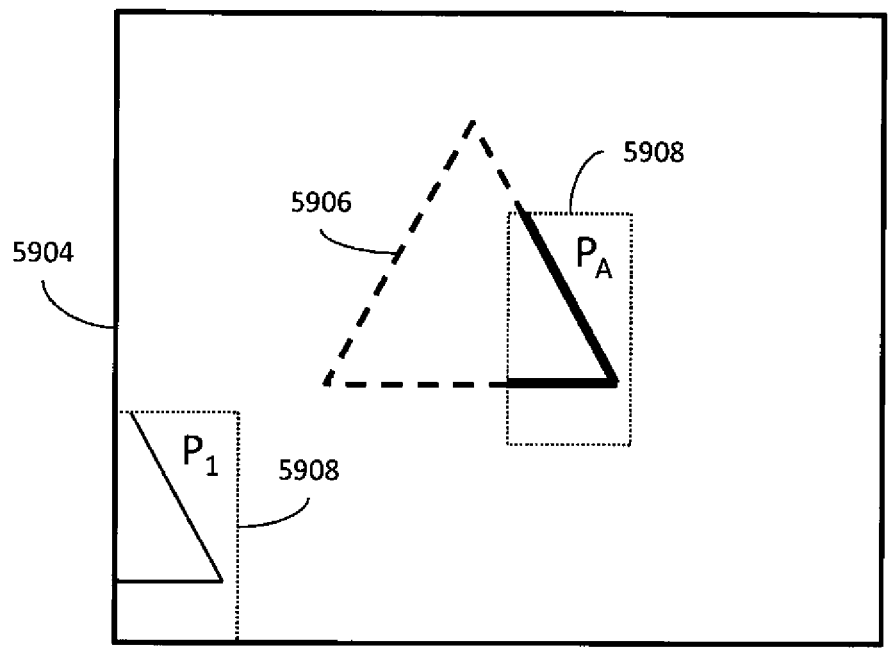
FIG. 59

METHODS, SYSTEMS, APPARATUSES, AND COMPUTER PROGRAMS FOR PROCESSING TOMOGRAPHIC IMAGES

CROSS-REFERENCE TO RELATED APPLICATIONS

This application is a continuation application of U.S. Non-Provisional patent application Ser. No. 15/510,596 filed Mar. 10, 2017, which is a National Stage Entry of PCT/US15/50497 filed Sep. 16, 2015 which claims priority to U.S. Provisional Patent Appln. No. 62/050,881, filed Sep. 16, 2014, 62/076,216, filed Nov. 6, 2014, and 62/214,830, filed Sep. 4, 2015, the contents of which are incorporated by reference herein in their entirety.

BACKGROUND

Field

The present application relates generally to obtaining tomographic images in a dental environment, and, more particularly, to methods, systems, apparatuses, and computer programs for processing tomographic images.

Description of Related Art

X-ray radiography can be performed by positioning an x-ray source on one side of an object (e.g., a patient or a portion thereof) and causing the x-ray source to emit x-rays through the object and toward an x-ray detector (e.g., radiographic film, an electronic digital detector, or a photostimulable phosphor plate) located on the other side of the object. As the x-rays pass through the object from the x-ray source, their energies are absorbed to varying degrees depending on the composition of the object, and x-rays arriving at the x-ray detector form a two-dimensional (2D) x-ray image (also known as a radiograph) based on the cumulative absorption through the object. This process is explained further in reference to FIG. 60A-FIG. 60C.

FIG. 60A shows a patient and an x-ray device 6000 positioned for obtaining an occlusal image of the mandible. A sensor or x-ray film (not shown) is disposed inside the patient's mouth. An exposure is recorded and an x-ray image is subsequently developed, as shown in FIG. 60B. In traditional x-ray imaging, the sensor (or film) records the intensity of the x-rays incident thereon, which are reduced (or attenuated) by the matter which lies in their respective paths. The recorded intensity represents that total attenuation of the x-ray through the image volume, as illustrated in FIG. 60C.

In FIG. 60C two x-rays (ray A and ray B) are incident on two adjacent sensor elements 6008 and 6010 of an x-ray detector. Ray A travels through two blocks of identical material, block 6002 and block 6004, each with an attenuation factor of 50%. Ray B travels through block 6006 which also has an attenuation factor of 50%. The intensity of Ray A recorded by sensor element 6008 is 25% of the original intensity. The intensity of Ray B recorded by sensor element 6010 is 50% of the original intensity. In a traditional x-ray image the recorded intensities are represented by light/dark regions. The lighter regions correspond to areas of greater x-ray attenuation and the darker regions correspond to areas of less, if any, x-ray attenuation. Thus, a two-dimensional projection image produced by sensor elements 6008 and 6010 will have a lighter region corresponding to sensor element 6008 and a darker region corresponding to sensor element 6010. However, from such a two-dimensional projection image it cannot be determined that there were two blocks of material (6002 and 6004) at different positions in the path of Ray A, as opposed to a single block of material which caused the same amount of x-ray attenuation. In other words, the traditional x-ray image contains no depth information. As such, overlapping objects may easily obscure one another and reduce the diagnostic usefulness of the projection image.

Computed tomography (CT) and cone beam computed tomography (CBCT) have been used to acquire three-dimensional data about a patient, which includes depth information. The three-dimensional data can be presented on a display screen for clinician review as a 3D rendering or as a stack of parallel 2D tomographic image slices. Each slice represents a cross-section of the patient's anatomy at a specified depth. While CT and CBCT machines may produce a stack of parallel 2D tomographic image slices, these machines carry a high cost of ownership, may be too large for use in chair-side imaging, and expose patients to a relatively high dose of x-rays.

Tomosynthesis is an emerging imaging modality that provides three-dimensional information about a patient in the form of tomographic image slices reconstructed from images taken of the patient with an x-ray source from multiple perspectives within a scan angle smaller than that of CT or CBCT (e.g., ±20°, compared with at least 180° in CBCT). Compared to CT or CBCT, tomosynthesis exposes patients to a lower x-ray dosage, acquires images faster, and may be less expensive.

Typically, diagnosis using tomosynthesis is performed by assembling a tomosynthesis stack of two-dimensional image slices that represent cross-sectional views through the patient's anatomy. A tomosynthesis stack may contain tens of tomosynthesis image slices. Clinicians locate features of interest within the patient's anatomy by evaluating image slices one at a time, either by manually flipping through sequential slices or by viewing the image slices as a cine loop, which are time-consuming processes. It may also be difficult to visually grasp aspects of anatomy in a proper or useful context from the two-dimensional images. Also, whether the tomographic images slices are acquired by CT, CBCT, or tomosynthesis, their usefulness for diagnosis and treatment is generally tied to their fidelity and quality.

Quality may be affected by image artifacts. Tomosynthesis datasets typically have less information than full CBCT imaging datasets due to the smaller scan angle, which may introduce distortions into the image slices in the form of artifacts. The extent of the distortions depends on the type of object imaged. For example, intraoral tomosynthesis imaging can exhibit significant artifacts because structures within the oral cavity are generally dense and radiopaque. Still further, spatial instability in the geometry of the tomosynthesis system and/or the object can result in misaligned projection images which can degrade the quality and spatial resolution of the reconstructed tomosynthesis image slices. Spatial instability may arise from intentional or unintentional motion of the patient, the x-ray source, the x-ray detector, or a combination thereof. It may therefore be desirable to diminish one or more of these limitations.

SUMMARY

One or more the above limitations may be diminished by methods, systems, apparatuses, and computer programs products for processing tomographic images as described herein.

In one embodiment, a method of identifying a tomographic image of a plurality of tomographic images is provided. Information specifying a region of interest in at least one of a plurality of projection images or in at least one of a plurality of tomographic images reconstructed from the plurality of projection images is received. A tomographic image of the plurality of tomographic images is identified. The identified tomographic image is in greater focus in an area corresponding to the region of interest than others of the plurality of tomographic images.

In another embodiment, an apparatus for identifying a tomographic image from a plurality of tomographic images. The apparatus includes a processor and a memory storing at least one control program. The processor and memory are operable to: receive information specifying a region of interest in at least one of a plurality of projection images or in at least one of a plurality of tomographic images reconstructed from a plurality of projection images, and identify a tomographic image of the plurality of tomographic images. The tomographic image is in greater focus in an area corresponding to the region of interest than others of the plurality of tomographic images.

In a further embodiment, a non-transitory computer-readable storage medium storing a program which, when executed by a computer system, causes the computer system to perform a method. The method includes receiving information specifying a region of interest in at least one of a plurality of projection images or in at least one of a plurality of tomographic images reconstructed from the plurality of projection images, and identifying a tomographic image of the plurality of tomographic images. The identified tomographic image is in greater focus in an area corresponding to the region of interest than others of the plurality of tomographic images.

In still another embodiment, a method for generating clinical information is provided. Information indicating at least one clinical aspect of an object is received. Clinical information of interest relating to the at least one clinical aspect is generated from a plurality of projection images. At least one of the steps is performed by a processor in conjunction with a memory.

In still a further embodiment, an apparatus for generating clinical information. The apparatus includes a processor and a memory storing at least one control program. The processor and the memory are operable to: receive information indicating at least one clinical aspect of an object, and generate, from a plurality of projection images, clinical information of interest relating to the at least one clinical aspect.

In yet another embodiment, a non-transitory computer readable storage medium storing a program which, when executed by a computer system, causes the computer system to perform a method. The method includes receiving information indicating at least one clinical aspect of an object, and generating, from a plurality of projection images, clinical information of interest relating to the at least one clinical aspect.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIGS. 31A to 31C are views for illustrating measurement of distances in a 3D image according to example embodiments herein.

FIGS. 33A-D are illustrations of a two-dimensional x-ray projection image, a tomosynthesis slice, a distance between the tomosynthesis slice and the x-ray detector, and the tomosynthesis slice within the image volume according to an example embodiment herein.

FIG. 34 is an image of a tomosynthesis slice according to an example embodiment herein.

FIGS. 40A-C are illustrations of a two-dimensional x-ray projection image, a tomosynthesis slice, and a volumetric image of the image volume with a vector disposed therein according to an example embodiment herein.

FIG. 53A is a perspective cross-sectional view of a human mandible.

FIG. 53B is a cross-sectional view of the lingual and buccal plates shown in FIG. 53A.

FIG. 53C is an exemplary two-dimensional image from a tomosynthesis stack.

FIG. 59 illustrates a correlation algorithm for determining the amount of shift for a region of interest.

Figure 1A:
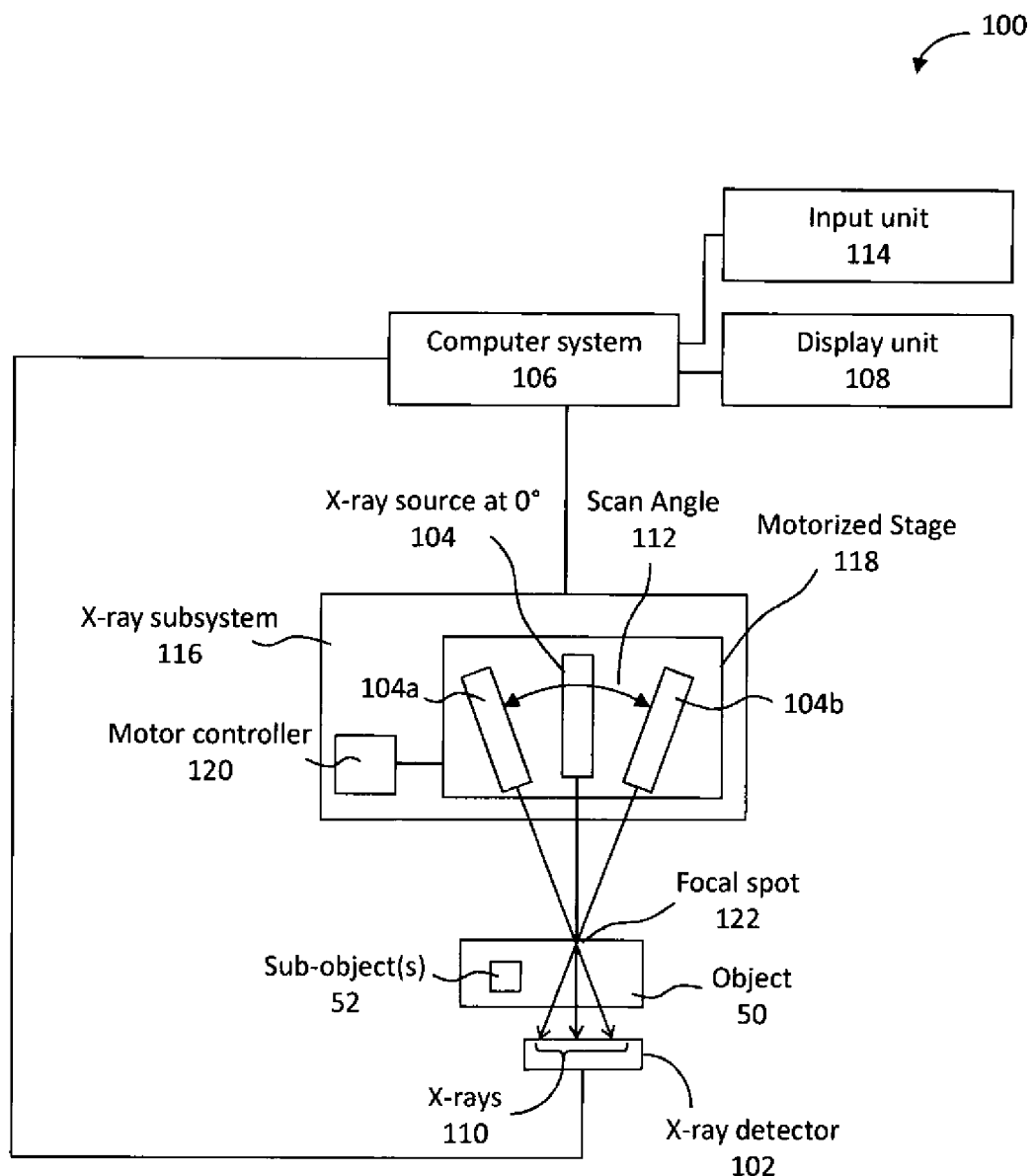
FIG. 1A is a system block diagram of a tomosynthesis system according to one example embodiment herein.

Different ones of the Figures may have at least some reference numerals that are the same in order to identify the same components, although a detailed description of each such component may not be provided below with respect to each Figure.

DETAILED DESCRIPTION OF THE PREFERRED EMBODIMENTS

In accordance with example aspects described herein, methods, systems, apparatuses, and computer programs are provided for generating clinical information from a tomographic dataset, and more particularly, for identifying within an intraoral tomosynthesis dataset high-focus images containing features of interest.

Tomosynthesis System

FIG. 1A illustrates a block diagram of an intraoral tomosynthesis system 100 for obtaining an intraoral tomosynthesis dataset, and which is constructed and operated in accordance with at least one example embodiment herein. The system 100 can be operated to obtain one or more x-ray images of an object 50 of interest, which may further include one or more sub-object(s) 52. For example, object 50 may be a tooth (or teeth) and surrounding dentition of a patient, and sub-object(s) 52 may be root structures within the tooth.

The system 100 includes an x-ray detector 102 and an x-ray subsystem 116, both of which, including subcomponents thereof, are electrically coupled to a computer system 106. In one example, the x-ray subsystem 116 hangs from a ceiling or wall-mounted mechanical arm (not shown), so as to be freely positioned relative to an object 50. The x-ray subsystem 116 further includes an x-ray source 104 mounted on a motorized stage 118 and an on-board motor controller 120. The on-board motor controller 120 controls the motion of the motorized stage 118.

The computer system 106 is electrically coupled to a display unit 108 and an input unit 114. The display unit 108 can be an output and/or input user interface.

The x-ray detector 102 is positioned on one side of the object 50 and the receiving surface of the x-ray detector 102 extends in an x-y plane in a Cartesian coordinate system. The x-ray detector 102 can be a small intraoral x-ray sensor that includes, for example, a complementary metal-oxide semiconductor (CMOS) digital detector array of pixels, a charge-coupled device (CCD) digital detector array of pixels, or the like. In an example embodiment herein, the size of the x-ray detector 102 varies according to the type of patient to whom object 50 belongs, and more particularly, the x-ray detector 102 may be one of a standard size employed in the dental industry. Examples of the standard dental sizes include a "Size-2" detector, which is approximately 27×37 mm in size and is typically used on adult patients, a "Size-1" detector, which is approximately 21×31 mm in size and is typically used on patients that are smaller than Size-2 adult patients, and a "Size-0" detector, which is approximately 20×26 mm in size and is typically used on pediatric patients. In a further example embodiment herein, each pixel of the x-ray detector 102 has a pixel width of 15 µm, and correspondingly, the Size-2 detector has approximately 4 million pixels in a 1700×2400 pixel array, the Size-1 detector has approximately 2.7 million pixels in a 1300×2000 pixel array, and the Size-0 detector has approximately 1.9 million pixels in a 1200×1600 pixel array. The color resolution of the x-ray detector 102 may be, in one example embodiment herein, a 12-bit grayscale resolution, although this example is not limiting, and other example color resolutions may include an 8-bit grayscale resolution, a 14-bit grayscale resolution, and a 16-bit grayscale resolution.

The x-ray source 104 is positioned on an opposite side of the object 50 from the x-ray detector 102. The x-ray source 104 emits x-rays 110 which pass through object 50 and are detected by the x-ray detector 102. The x-ray source 104 is oriented so as to emit x-rays 110 towards the receiving surface of the x-ray detector 102 in at least a z-axis direction of the Cartesian coordinate system, where the z-axis is orthogonal to the x-y plane associated with the receiving surface of the x-ray detector 102.

The x-ray source 104 can also emit x-rays 110 while positioned at each of multiple different locations within a scan angle 112, where a 0° position in the scan angle 112 corresponds to the position for emitting x-rays 110 along the z-axis. In one example embodiment herein, the user initially positions the x-ray subsystem 116, and hence, also the x-ray source 104, to a predetermined starting position relative to the object 50. The computer system 106 then controls the on-board motor controller 120 to move the x-ray source 104 via the motorized stage 118, based on the known starting position, to step through each of the different locations within the scan angle 112. The computer system 106 controls the x-ray source 104 to cause the source 104 to emit x-rays 110 at each of those locations.

The centroid of the x-rays 110 passes through a focal spot 122 at each of the different locations within the scan angle 112. The focal spot 122 may be, for example, located close to the detector such that x-rays 110 emitted from the x-ray source 104 positioned at the outer limits of the scan angle 112 are aimed at and do not miss the x-ray detector 102. In FIG. 1A, the 0° position is represented in x-ray source 104, while reference numerals 104a and 104b represent the same x-ray source 104 but in two other example positions within the scan angle 112. The scan angle 112 can be, for example, ±20° from the 0° position, although this example is not limiting.

Figure 1B:
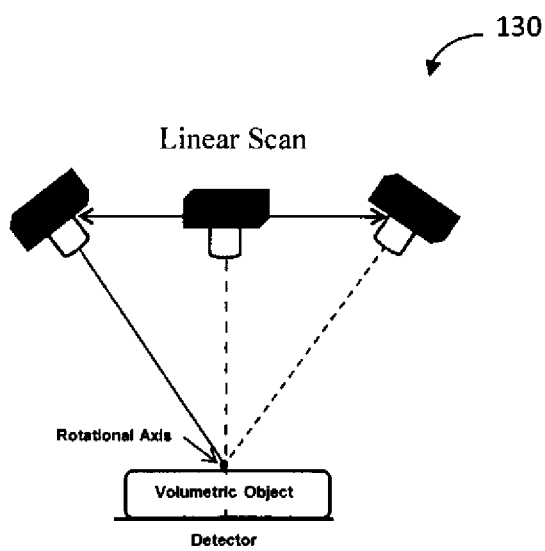
FIG. 1B illustrates an example of a linear scan path used by the tomosynthesis system according to an example embodiment herein.
Figure 1C:
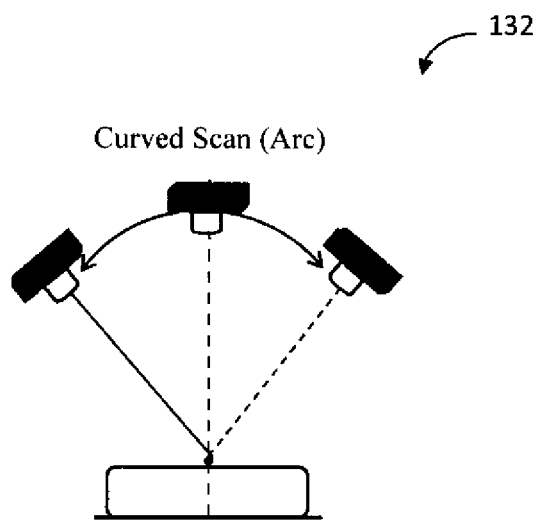
FIG. 1C illustrates an example of a curved scan path used by the tomosynthesis system according to an example embodiment herein.
Figure 1D:
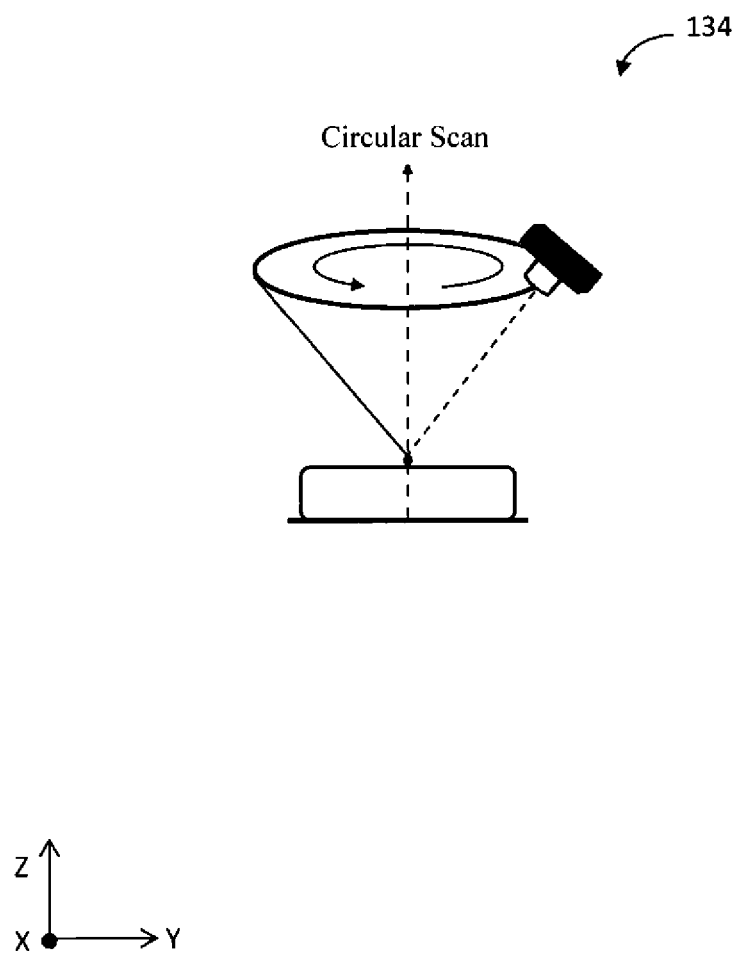
FIG. 1D illustrates an example of a circular scan path used by the tomosynthesis system according to an example embodiment herein.

Additionally, the motion of x-ray source 104 along the scan angle 112 may form different scan paths, such as, for example, a linear scan 130 shown in FIG. 1B, a curved scan 132 shown in FIG. 1C, or a circular scan 134 shown in FIG. 1D. In the linear scan 130 (FIG. 1B), the x-ray source 104 moves linearly in an x-y plane while emitting x-rays 110 toward the focal spot 122, forming a triangular sweep. In the curved scan 132 (FIG. 1C), the x-ray source 104 moves in an arc while emitting x-rays 110 toward the focal spot 122, forming a fan beam sweep. In the circular scan 134 (FIG. 1D), the x-ray source 104 rotates around the z-axis while emitting x-rays 110 toward the focal spot 122, forming a conical beam sweep. The scan positions also may be arranged in any particular one or more planes of the Cartesian coordinate system.

As emitted x-rays 110 pass through the object 50, photons of x-rays 110 will be more highly attenuated by high density structures of the object 50, such as calcium-rich teeth and bone, and less attenuated by soft tissues, such as gum and cheek. One or more of the attenuating structures can be sub-object(s) 52. X-rays 110 passing through and attenuated by object 50, are projected onto x-ray detector 102, which converts the x-rays 110 into electrical signals and provides the electrical signals to computer system 106. In one example embodiment, the x-ray detector 102 may be an indirect type of detector (e.g., a scintillator x-ray detector) that first converts x-rays 110 into an optical image and then converts the optical image into the electrical signals, and in another example embodiment, the x-ray detector 102 may be a direct type of detector (e.g., a semiconductor x-ray detector) that converts x-rays 110 directly into the electrical signals. The computer system 106 processes the electrical signals to form a two-dimensional projection image of the object 50. In one example embodiment herein, the image size of the two-dimensional projection image corresponds to the dimensions and the number of pixels of the x-ray detector 102.

Figure 1E:
FIG. 1E illustrates an example of shadow casting from an orthogonal projection angle.
Figure 1F:
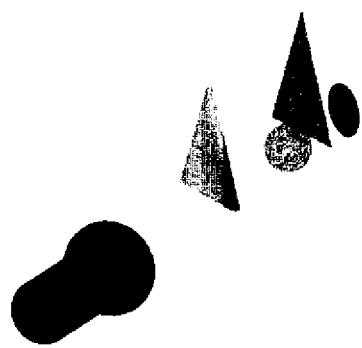
FIG. 1F illustrates an example of shadow casting from a non-orthogonal projection angle and the parallax induced in the image of the objects.

The system 100 can collect a plurality of projection images, as described above, by first positioning the x-ray source 104 at different angles, including at least the 0° position, and emitting x-rays 110 at each of those different angles through object 50 towards x-ray detector 102. For example, the plurality of projection images may include a total of fifty-one projections: one orthogonal projection image, obtained when the x-ray source is at the 0° position, and fifty projection images, each obtained when the x-ray source 104 is positioned at different angles within a range of ±20° from the z-axis (corresponding to the scan angle 112). In other example embodiments, the number of projection images may range from twenty-five to seventy. Because the orthogonal projection image is obtained when the x-ray source is at the 0° position, the orthogonal projection image has the same appearance as a conventional x-ray image. That is, the two-dimensional orthogonal projection image has no depth perception, and one or more sub-object(s) 52 within object 50 may appear overlaid one on top of another in the orthogonal projection image, as represented in FIG. 1E, for example. On the other hand, sub-object(s) 52 at different depths of the z-axis within object 50 undergo varying degrees of parallax when imaged from different angles along the scan angle 112, as represented in FIG. 1F, for example.

The computer system 106 processes the plurality of projection images to reconstruct a series of two-dimensional tomosynthesis image slices, also known as a tomosynthesis stack of images, in a manner to be described below. Each image slice is parallel to the plane in which the receiving surface of the x-ray detector 102 extends and at different depths of the z-axis.

The computer system 106 further processes the tomosynthesis image slices in a manner to be described below, to generate clinically relevant information related to object 50 (e.g., a patient's dental anatomy), and in a further example embodiment herein, related to sub-object(s) 52. The extracted information may include the identification, within the tomosynthesis stack of images, of high-focus images that contain features of interest therein. In one example embodiment herein, the computer system 106 obtains input from a user via input unit 114 and/or display unit 108 to guide the further processing of the tomosynthesis slices.

The orthogonal projection image, one or more image slices of the tomosynthesis stack, and the extracted information are provided by the computer system 106 for display to the user on the display unit 108.

Compared to a dental CBCT system, the intraoral tomosynthesis imaging system 100 carries a lower cost of ownership, can acquire images faster and with higher resolution (e.g., a per pixel resolution of approximately 20 μm, compared to a per pixel resolution of 100-500 μm with CBCT), and exposes patients to a lower x-ray dose (e.g. approximately an order of magnitude lower in some cases, owing in part to a smaller field of view, a smaller scan angle, and the need to only penetrate the anatomy between the x-ray source 104 and the x-ray detector 102, rather than the complete jaw). Additionally, in some example embodiments herein, the intraoral tomosynthesis system 100 can resemble a conventional x-ray radiography system, and can use the same or substantially similar equipment, such as, for example, the ceiling- or wall-mounted mechanical arm for positioning the x-ray source 104, a similarly-sized x-ray source 104, and the intraoral x-ray detector 102. Accordingly, operation of the intraoral tomosynthesis system 100 is more familiar and less complex to a clinician, compared to dental CBCT, and also can be used chair-side.

Computer System for Tomosynthesis Imaging

Having described a system 100 for acquiring a tomosynthesis dataset and for generating clinically relevant information from a tomosynthesis dataset, including the identification of high-focus images containing features of interest, reference will now be made to FIG. 2A, which shows a block diagram of a computer system 200 that may be employed in accordance with at least some of the example embodiments herein. Although various embodiments are described herein in terms of this exemplary computer system 200, after reading this description, it will become apparent to a person skilled in the relevant art(s) how to implement the invention using other computer systems and/or architectures.

Figure 2A:
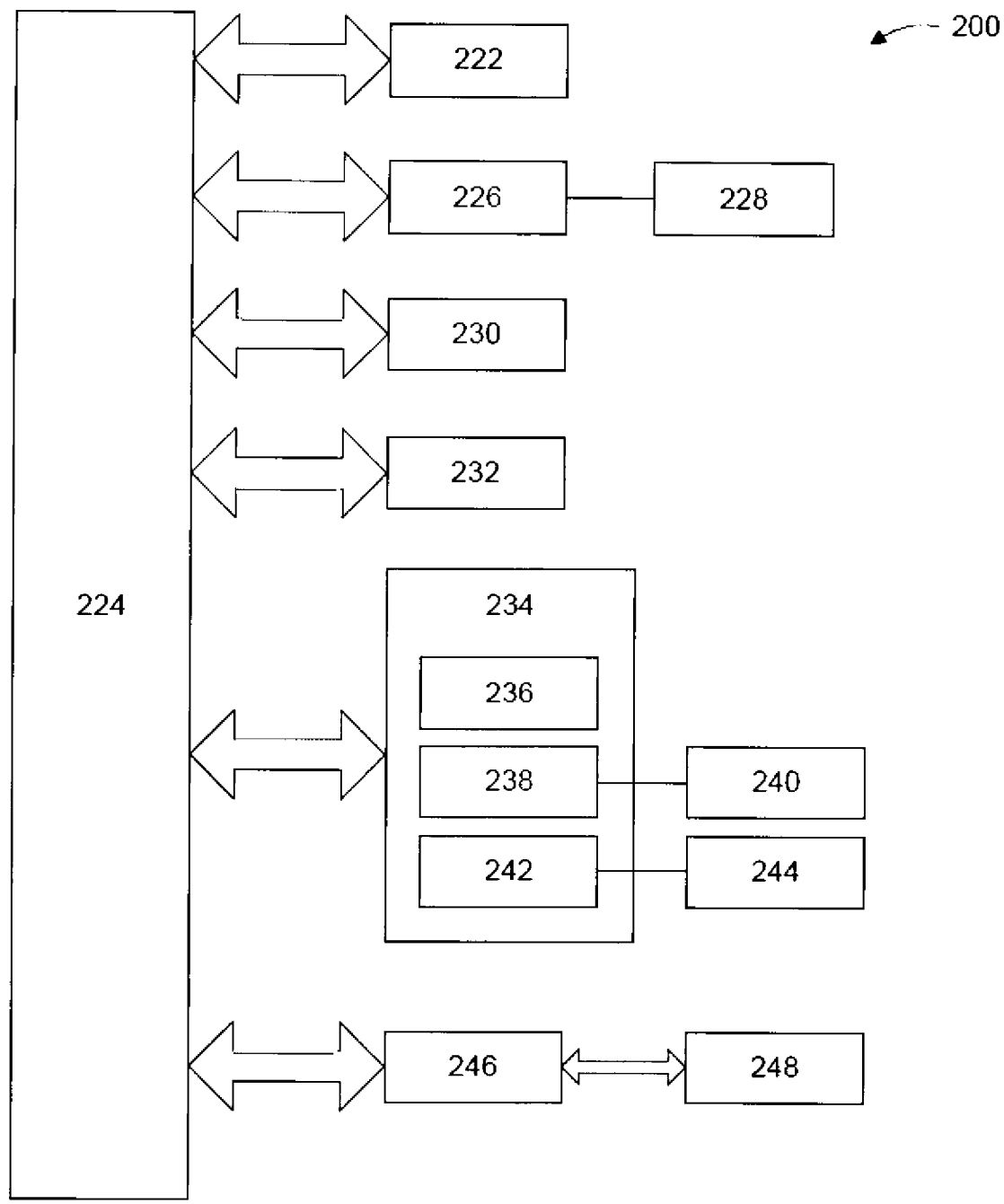
FIG. 2A illustrates a block diagram of an example computer system of the tomosynthesis system shown in FIG. 1A.

FIG. 2A illustrates a block diagram of the computer system 200. In one example embodiment herein, at least some components of the computer system 200 (such as all those components, or all besides component 228) can form or be included in the computer system 106 shown in FIG. 1A. The computer system 200 includes at least one computer processor 222 (also referred to as a "controller"). The computer processor 222 may include, for example, a central processing unit, a multiple processing unit, an application-specific integrated circuit ("ASIC"), a field programmable gate array ("FPGA"), or the like. The processor 222 is connected to a communication infrastructure 224 (e.g., a communications bus, a cross-over bar device, or a network).

The computer system 200 also includes a display interface (or other output interface) 226 that forwards video graphics, text, and other data from the communication infrastructure 224 (or from a frame buffer (not shown)) for display on a display unit 228 (which, in one example embodiment, can form or be included in the display unit 108). For example, the display interface 226 can include a video card with a graphics processing unit.

The computer system 200 also includes an input unit 230 that can be used by a user of the computer system 200 to send information to the computer processor 222. In one example embodiment herein, the input unit 230 can form or be included in the input unit 114. For example, the input unit 230 can include a keyboard device and/or a mouse device or other input device. In one example, the display unit 228, the input unit 230, and the computer processor 222 can collectively form a user interface.

In an example embodiment that includes a touch screen, for example, the input unit 230 and the display unit 228 can be combined, or represent a same user interface. In such an embodiment, a user touching the display unit 228 can cause corresponding signals to be sent from the display unit 228 to the display interface 226, which can forward those signals to a processor such as processor 222, for example.

In addition, the computer system 200 includes a main memory 232, which preferably is a random access memory ("RAM"), and also may include a secondary memory 234. The secondary memory 234 can include, for example, a hard disk drive 236 and/or a removable-storage drive 238 (e.g., a floppy disk drive, a magnetic tape drive, an optical disk drive, a flash memory drive, and the like). The removable-storage drive 238 reads from and/or writes to a removable storage unit 240 in a well-known manner. The removable storage unit 240 may be, for example, a floppy disk, a magnetic tape, an optical disk, a flash memory device, and the like, which is written to and read from by the removable-storage drive 238. The removable storage unit 240 can include a non-transitory computer-readable storage medium storing computer-executable software instructions and/or data.

In alternative embodiments, the secondary memory 234 can include other computer-readable media storing computer-executable programs or other instructions to be loaded into the computer system 200. Such devices can include a removable storage unit 244 and an interface 242 (e.g., a program cartridge and a cartridge interface similar to those used with video game systems); a removable memory chip (e.g., an erasable programmable read-only memory ("EPROM") or a programmable read-only memory ("PROM")) and an associated memory socket; and other removable storage units 244 and interfaces 242 that allow software and data to be transferred from the removable storage unit 244 to other parts of the computer system 200.

The computer system 200 also can include a communications interface 246 that enables software and data to be transferred between the computer system 200 and external devices. Examples of the communications interface 246 include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCMCIA") interface, and the like. Software and data transferred via the communications interface 246 can be in the form of signals, which can be electronic, electromagnetic, optical or another type of signal that is capable of being transmitted and/or received by the communications interface 246. Signals are provided to the communications interface 246 via a communications path 248 (e.g., a channel). The communications path 248 carries signals and can be implemented using wire or cable, fiber optics, a telephone line, a cellular link, a radio-frequency ("RF") link, or the like. The communications interface 246 may be used to transfer software or data or other information between the computer system 200 and a remote server or cloud-based storage (not shown).

One or more computer programs (also referred to as computer control logic) are stored in the main memory 232 and/or the secondary memory 234. The computer programs also can be received via the communications interface 246. The computer programs include computer-executable instructions which, when executed by the computer processor 222, cause the computer system 200 to perform the procedures as described herein (and shown in figures), for example. Accordingly, the computer programs can control the computer system 106 and other components (e.g., the x-ray detector 102 and the x-ray source 104) of the intraoral tomosynthesis system 100.

In one example embodiment herein, the software can be stored in a non-transitory computer-readable storage medium and loaded into the main memory 232 and/or the secondary memory 234 of the computer system 200 using the removable-storage drive 238, the hard disk drive 236, and/or the communications interface 246. Control logic (software), when executed by the processor 222, causes the computer system 200, and more generally the intraoral tomosynthesis system 100, to perform the procedures described herein.

In another example embodiment hardware components such as ASICs, FPGAs, and the like, can be used to carry out the functionality described herein. Implementation of such a hardware arrangement so as to perform the functions described herein will be apparent to persons skilled in the relevant art(s) in view of this description.

Having provided a general description of the tomosynthesis system 100, techniques for processing data from the tomosynthesis system 100 (or as the case may be a CT or CBCT machine as well) will be described below. As one of ordinary skill will appreciate, description corresponding to one technique may be applicable to another technique described herein.

Generating Clinical Information from a Dataset

Generally, for x-ray images to have value and utility in clinical diagnosis and treatment, they should have high image fidelity and quality (as measured by resolution, brightness, contrast, signal-to-noise ratio, and the like, although these example metrics are not limiting) so that anatomies of interest can be clearly identified, analyzed (e.g., analysis of shape, composition, disease progression, etc.), and distinguished from other surrounding anatomies.

In addition to providing tomosynthesis image slices with good image fidelity and quality (although such is not necessary), an intraoral tomosynthesis system 100 according to example aspects herein augments the tomosynthesis image slices by automatically or semi-automatically generating clinical information of interest about the imaged object 50 and presenting the same to the clinician user. In an example embodiment herein, the clinical information of interest relates to anatomical features (such as sub-object(s) 52) located at a depth within the object 50, and such anatomical features may not be readily apparent in the tomosynthesis image slices under visual inspection by the clinician user and also may not be visible in a conventional 2D radiograph due to overlapping features from other depths.

Figure 2B:
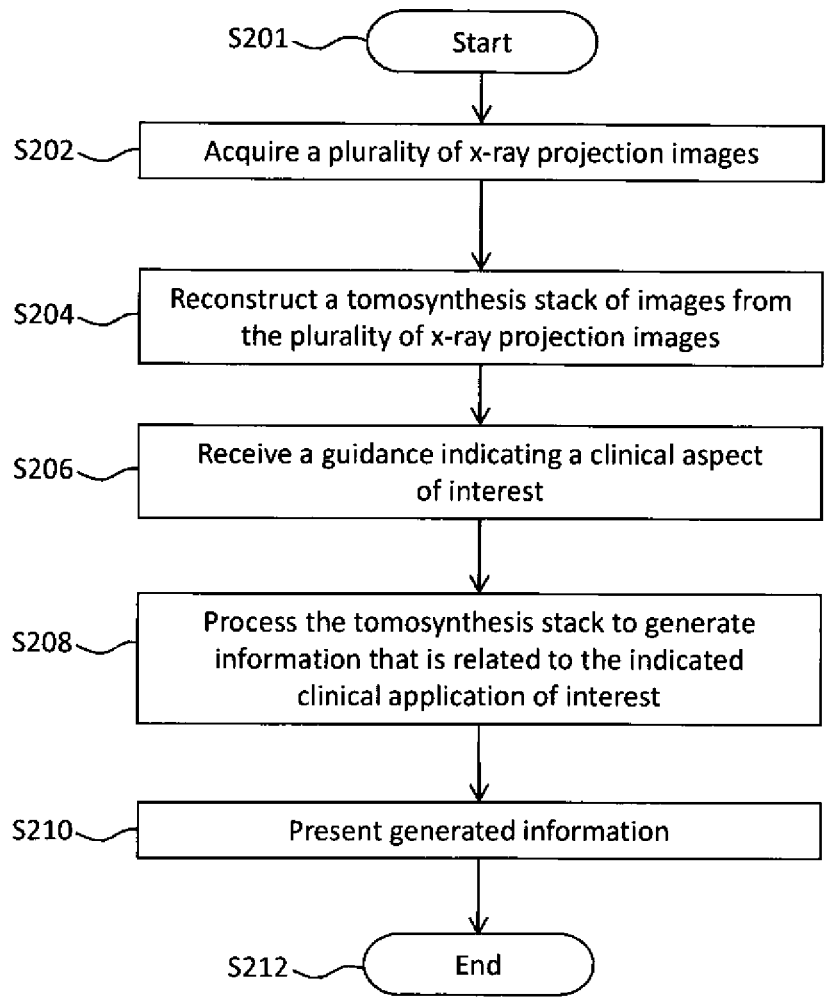
FIG. 2B is a flowchart illustrating a procedure for generating clinical information from a tomosynthesis dataset according to an example aspect herein.

The intraoral tomosynthesis system 100 will now be further described in conjunction with FIG. 2B, which shows a flow diagram of a process for generating clinical information of interest according to an example embodiment herein.

The process of FIG. 2B starts at Step S201, and in Step S202, the tomosynthesis system 100 acquires a plurality of projection images of the object 50 over a scan angle 112.

In Step S204, the computer system 106 processes the plurality of projection images to reconstruct a series of two-dimensional tomosynthesis image slices (also known as a tomosynthesis stack), each image slice representing a cross-section of the object 50 that is parallel to the x-ray detector 102 and each slice image also being positioned at a different, respective, location along the z-axis (i.e., in a depth of the object 50) than other image slices. (The reconstruction of the tomosynthesis stack in Step S204 can be substantially the same process as that of Step S304 of FIG. 3 described in greater detail herein below.)

In Step S206, the computer system 106 receives, via input unit 114 and/or display unit 108, a guidance from a clinician user indicating a clinical aspect of interest. In an example embodiment herein, the received guidance may be a user selection from among a predetermined list of tools presented by the computer system 106.

The guidance received in Step S206 may be, for example, and without limitation, a selection of at least one region of interest on at least one of the projection images or the tomosynthesis image slices, at least one anatomy of interest (e.g., mental foramen, nerve canal, sinus floor, sinus cavity, nasal cavity, periodontal ligament, lamina dura, or other dental anatomies), a type of dental procedure (e.g., an endodontic procedure, a periodontic procedure, an implantation, caries detection, crack detection, and the like), a measurement inquiry (e.g., a distance measurement, a volumetric measurement, a density measurement, and the like), or any combination thereof In Step S208, the computer system 106 processes the tomosynthesis stack to generate information that is relevant to the clinical aspect of interest indicated by the guidance received in Step S206. In an example embodiment herein, the computer system 106 performs a processing in Step S208 that is predetermined to correspond to the received guidance.

Non-limiting examples of tomosynthesis stack processing that can be performed in Step S208 (and the information generated thereby) for a particular received guidance are as follows.

Figure 11:
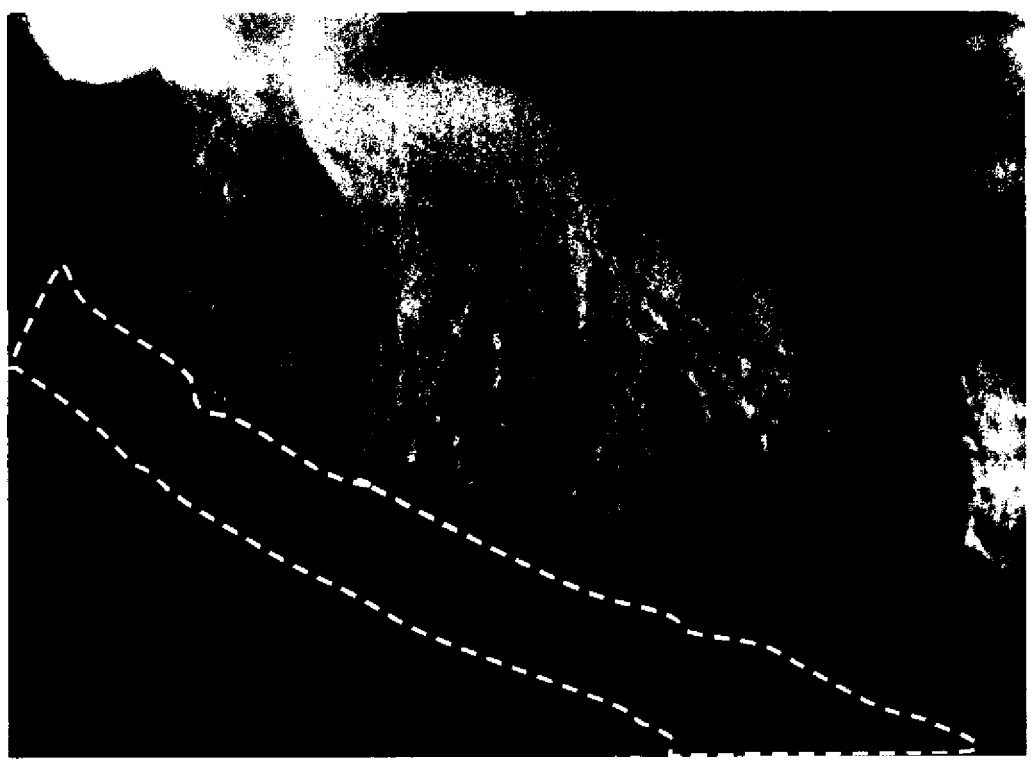
FIG. 11 illustrates an example tomosynthesis image slice with a nerve canal indicated.
Figure 12:
FIG. 12 illustrates an example tomosynthesis image slice with a sinus cavity indicated.
Figure 13A:
FIG. 13A illustrates an example 2D radiograph.
Figure 13B:
FIG. 13B illustrates an example tomosynthesis image slice of the anatomy of FIG. 13A, wherein the nasal cavity is indicated.
Figure 13C:
FIG. 13C illustrates another example tomosynthesis image slice of the anatomy of FIG. 13A, wherein the nasal cavity is indicated.

In an example embodiment herein where the received guidance is a selection of at least one region of interest on at least one of the projection images or the tomosynthesis image slices, the computer system 106 processes the tomosynthesis stack according to a process described further herein below with reference to FIG. 3.

Where the received guidance is at least one anatomy of interest (e.g., mental foramen, nerve canal, sinus floor, sinus cavity, nasal cavity, periodontal ligament, lamina dura, or other dental anatomies), the computer system 106 processes the tomosynthesis stack to identify the anatomy of interest (e.g., by way of image segmentation). One or more image segmentation techniques may be used to identify the anatomy of interest including, for example, a Hough transformation, a gradient segmentation technique, and a minimal path (geodesic) technique, which are discussed in further detail below. The computer system 106 generates, as generated information, a display that indicates the anatomy of interest (e.g., by highlighting, outlining, or the like). In one example embodiment herein, the display can be the tomosynthesis image slices with the identified anatomy indicated thereon or a 3D rendering of the identified anatomy. For example, FIG. 11 illustrates a tomosynthesis image slice with a nerve canal 1102 outlined thereon, and FIG. 12 illustrates a tomosynthesis image slice with a sinus cavity 1202 outlined thereon. As another example, FIG. 13A illustrates a 2D radiograph of a patient's anatomy, wherein a nasal cavity is less clearly defined, but, by virtue of performing Step S208 on a tomosynthesis dataset acquired from the same anatomy, the computer system 106 identifies the nasal cavity and indicates at least the nasal cavity walls 1302, 1304, 1306, and 1308 on the tomosynthesis image slices shown in FIGS. 13B and 13C.

If the received guidance is a type of dental procedure (e.g., an endodontic procedure, a periodontic procedure, an implantation, caries detection, crack detection, and the like), the computer system 106 generates information specific to the dental procedure.

For example, for a guidance indicating an endodontic root canal procedure, the computer system 106 processes the tomosynthesis dataset to identify root canals and generates a display of the identified root canals as the generated information (as discussed below). For example, the generated information can be the tomosynthesis image slices with the root canals highlighted and/or a 3D rendering of the root canals. In an additional example embodiment herein, the computer system 106 can generate spatial information related to the shape of the root canal, such as, for example, its location, curvature, and length.

For a received guidance indicating an implantation, the computer system 106, in an example embodiment herein, processes the tomosynthesis stack and generates, as the generated information, locations of anatomical landmarks of interest for an implant procedure, such as, for example, a location of the nerve canal, a location of the sinus floor, a location of the gingival margin, and a location of the buccal plate, through image segmentation. The computer system 106 can also generate, as the generated information, a 3D rendering of the jaw with the teeth virtually extracted.

For a received guidance indicating caries detection, the computer system 106, in an example embodiment herein, processes the tomosynthesis stack to detect caries and generates, as the generated information, the locations of carious lesion(s). In one embodiment, the guidance may include information that the computer system 106 uses to evaluate segmented regions and identify one or more of the regions as carious regions. Such information may include, for example, expected region size and attenuation amounts for a carious region. The locations of carious lesion(s) can be in the form of the tomosynthesis image slices with the carious region(s) highlighted thereon or a 3D rendering of the affected tooth of teeth with the carious volume(s) highlighted thereon.

Figure 14A:
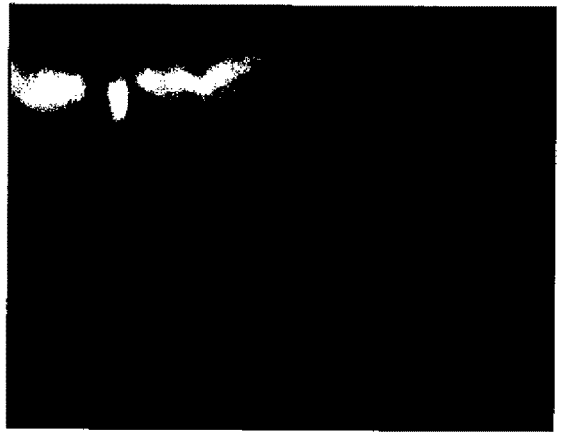
FIG. 14A illustrates an example 2D radiograph.
Figure 14B:
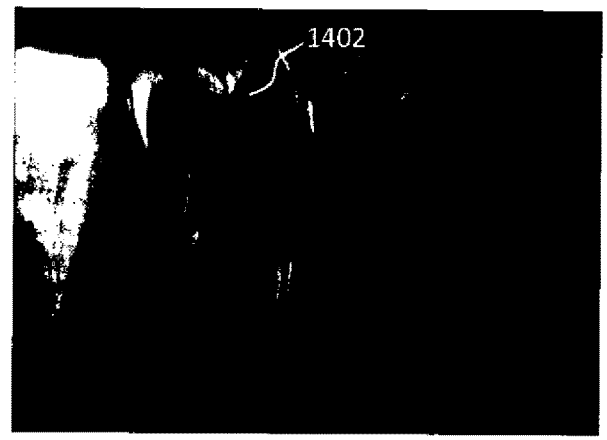
FIG. 14B illustrates an example tomosynthesis image slice of the teeth of FIG. 14A, wherein a crack is visible.
Figure 14C:
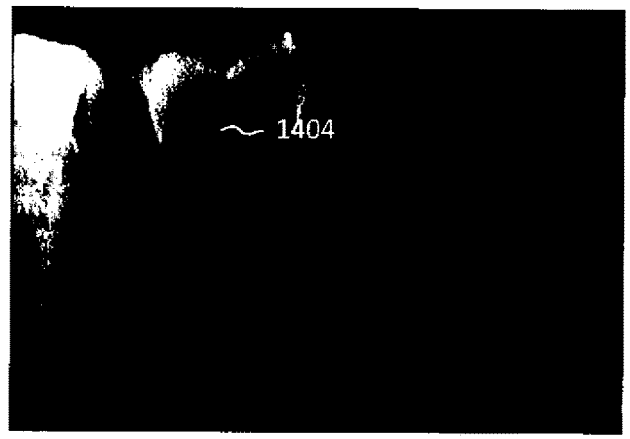
FIG. 14C illustrates another example tomosynthesis image slice of the teeth of FIG. 14A, wherein a crack is visible.

For a received guidance indicating crack detection, the computer system 106, in an example embodiment herein, processes the tomosynthesis stack to detect cracks and generates, as the generated information, the location of any cracks in the imaged tooth or teeth. In some example embodiments herein, the location of a crack can be in the form of the tomosynthesis image slices with the crack indicated thereon or a 3D rendering of the affected tooth of teeth with the crack indicated thereon. For example, the computer system 106 can process a tomosynthesis dataset to identify cracks in the imaged teeth (using image segmentation), and then generate the tomosynthesis image slices shown in FIGS. 14B and 14C with the identified cracks 1402 and 1404 indicated thereon, respectively.

In an example embodiment herein where the received guidance is a measurement inquiry (e.g., a distance measurement, an 2D area or 3D volumetric measurement, a density measurement, and the like), the computer system 106 processes the tomosynthesis stack to calculate the requested measurement as the generated information. For example, the computer system 100 can calculate, as the generated information, a distance between at least two user-selected points in the tomosynthesis dataset, a distance between two or more anatomies identified in the manner described above, an area or volume of an identified anatomy or of a user-selected region of the tomosynthesis dataset, or a density of an identified anatomy or of a region of the tomosynthesis dataset.

In Step S210, the computer system 106 presents the information generated in Step S208 to the user on the display unit 108. In an example embodiment herein, the computer system 106 can present the information generated in Step S208 by way of a user interface displayed on display unit 108.

Figure 15:
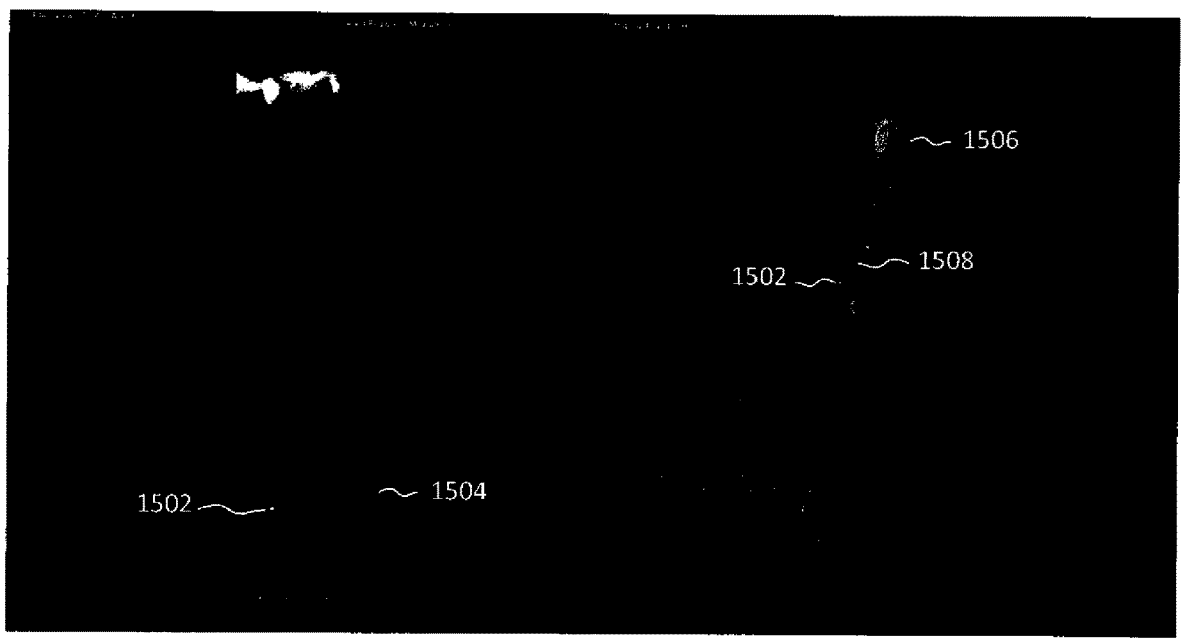
FIG. 15 illustrates an example user interface that displays clinical information of interest according to an example embodiment herein.

FIG. 15 illustrates a particular example of a user interface for presenting, in accordance with Step S210, information generated in Step S208 in response to a guidance received in Step S206 to locate the mental foramen 1502. In the particular example shown in FIG. 15, the computer system 106 displays a tomosynthesis image slice 1504 with the location of the mental foramen 1502 indicated thereon, a 3D rendering of a tooth 1506 with the location of the mental foramen 1502 indicated in 3D space in relation to the 3D-rendered tooth 1506, and a distance measurement 1508 from the apex of the 3D-rendered tooth 1506 to the mental foramen 1502.

The process of FIG. 2B ends at Step S212.

As can be appreciated in view of the foregoing, by virtue of the processing being performed on a tomosynthesis stack, which includes 3D information about the object 50 as explained above, the generated information also provides to the clinician user a depth information and depth context about the object 50 that may not be readily apparent in the tomosynthesis image slices under visual inspection by the clinician user and also may not be visible in a conventional 2D radiograph due to overlapping features from other depths.

Figure 16A:
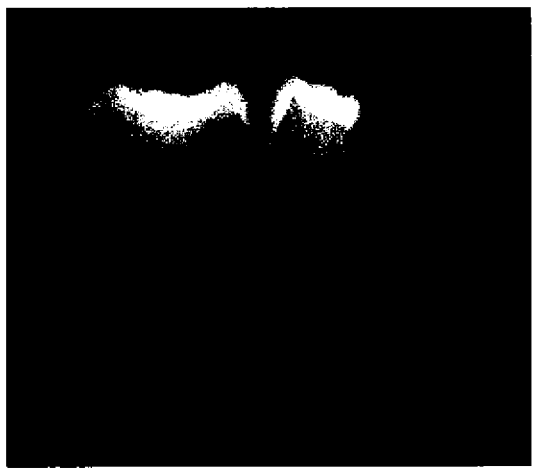
FIG. 16A illustrates an example 2D radiograph.
Figure 16B:
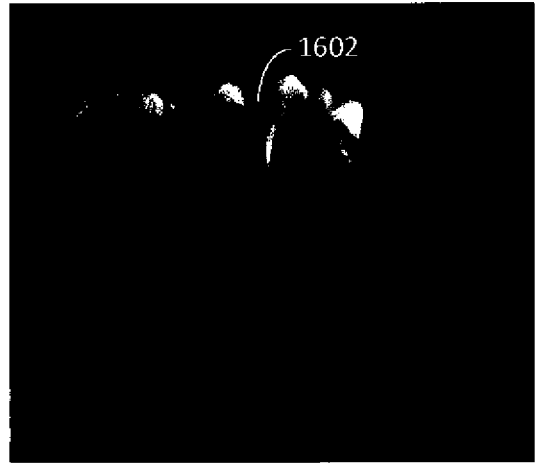
FIG. 16B illustrates an example tomosynthesis image slice of the teeth of FIG. 16A, wherein the interproximal space is visible.

As one particular example of useful depth information provided to a user, the tomosynthesis system 100 performing the process of FIG. 2B can automatically detect interproximal caries between teeth, because an interproximal space (e.g., space 1602 on FIG. 16B) between teeth is visible in at least one of the tomosynthesis image slices but would be obscured by overlapping anatomies in a conventional 2D radiograph of the same region (e.g., FIG. 16A). As another particular example of a depth information, the tomosynthesis system 100 performing the process of FIG. 2B can automatically detect dental cracks (e.g., cracks 1402 and 1404 on FIGS. 14B and 14C, respectively) in individual ones of the tomosynthesis image slices, which also may be obscured by overlapping anatomies in a conventional 2D radiograph (e.g., FIG. 14A).

Additionally, by virtue of using the computer system 106 to perform at least part of the process shown in FIG. 2B and described above, the tomosynthesis system 100 can be controlled to acquire images of lower fidelity and lower quality, thus potentially lowering the x-ray exposure to the patient and reducing image acquisition time, even while generating and presenting clinical information of high value and utility.

Identifying High-Focus Images within a Dataset

Figure 3:
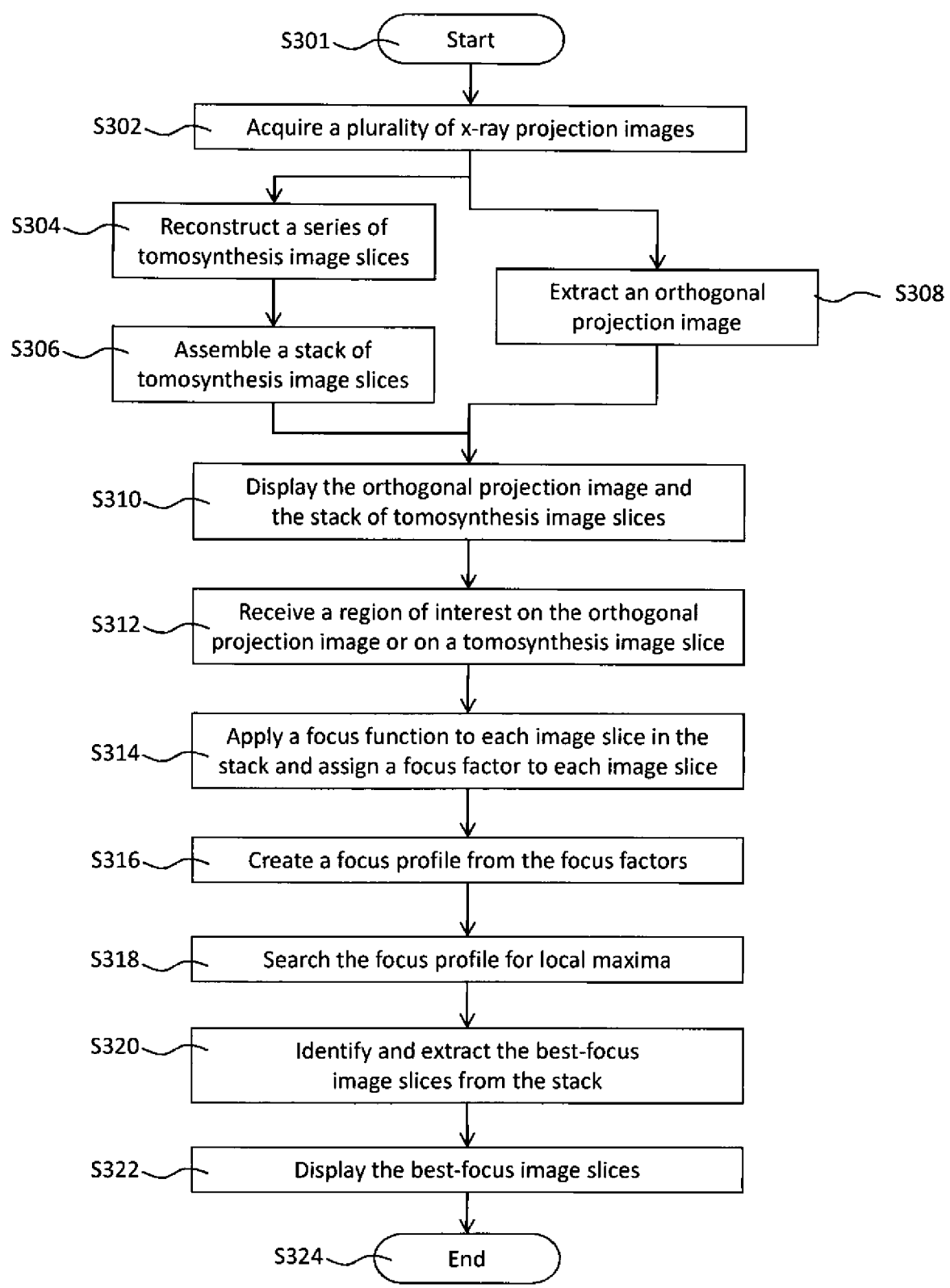
FIG. 3 is a flowchart illustrating a procedure for identifying high-focus images within a tomosynthesis dataset according to an example embodiment herein.

The intraoral tomosynthesis system 100 will now be further described in conjunction with FIG. 3, which shows a flow diagram of a process according to an example embodiment herein for identifying high-focus images within a tomosynthesis dataset. Prior to starting the process, the x-ray detector 102 and x-ray source 104 are aligned manually by a user to a starting position, as described above, in one example embodiment herein.

The process of FIG. 3 starts at Step S301, and, in Step S302, the intraoral tomosynthesis system 100 acquires a plurality of projection images of object 50 over a scan angle 112 (which may be predetermined), including the orthogonal projection image, in the manner described above. For example, the x-ray source 104 is moved by the motorized stage 118 and control circuitry 120 to different positions within the scan angle 112, and the computer system 106 controls the x-ray source 104 to emit x-rays 110 at each position. In one example embodiment herein, x-ray source 104 is scanned, by pivoting at a point along the z-axis, from −20° from the z-axis to +20° from the z-axis in evenly distributed increments of 0.8° to provide 51 scan angles, including the 0° position, although this example is not limiting. The x-rays 110 then pass through and are attenuated by the object 50 before being projected onto the x-ray detector 102. The x-ray detector 102 converts the x-rays 110 into electrical signals (either directly or indirectly, as described above) and provides the electrical signals to the computer system 106. The computer system 106 processes the electrical signals collected at each scan angle position to acquire the plurality of projection images, each image comprising an array of pixels. The image acquired with the x-ray source 104 at the 0° position is also referred to herein as an orthogonal projection image.

In one example embodiment herein, the color depth of each pixel value of the projection images may be 12-bit grayscale, and the dimensions of the projection images correspond to the standard dental size of the x-ray detector 102, as described above. For example, a Size-2 detector may produce projection images that are approximately 1700×2400 pixels in size, a Size-1 detector may produce projection images that are approximately 1300×2000 pixels in size, and a Size-0 detector may produce projection images that are approximately 1200×1600 pixels in size.

In Step S304, the computer system 106 processes the plurality of projection images acquired in Step S302 using a reconstruction technique in order to reconstruct a series of two-dimensional tomosynthesis image slices and may also perform deblurring and other image enhancements, as will be described further herein. Each reconstructed image slice is a tomographic section of object 50 comprising an array of pixels, that is, each image slice represents a cross-section of object 50 that is parallel to the x-y plane in which the receiving surface of the x-ray detector 102 extends, has a slice thickness along the z-axis, and is positioned at a different, respective location along the z-axis than other image slices. The slice thickness is a function of the reconstruction technique and aspects of the geometry of the system 100, including, primarily, the scan angle 112. For example, each image slice may have a slice thickness of 0.5 mm by virtue of the geometry of the system 100 and the reconstruction technique. The desired location of each reconstructed image slice along the z-axis is provided as an input to the reconstruction performed in Step S304 either as a pre-programmed parameter in computer system 106 or by user input via input unit 114 and/or display unit 108. By example only, the computer system 106 can be instructed to reconstruct, from the plurality of projection images, a first image slice that is one millimeter (1 mm) away from the surface of x-ray detector 102 along the z-axis, a last image slice being at fifteen millimeters (15 mm) away from the surface of the x-ray detector 102, and image slices between the first image slice and the last image slice at regular increments along the z-axis of two-hundred micrometers (200 μm), for a total of seventy-one image slices.

Reconstruction of the tomosynthesis image slices in Step S304 may be performed in accordance with any existing or later developed reconstruction technique. For example, a shift-and-add method, filtered backprojection, matrix inversion tomosynthesis, generalized filtered backprojection, SIRT (simultaneous iterative reconstruction technique), or algebraic technique, among others, may be used. In one example embodiment herein, reconstruction of the tomosynthesis image slices in Step S304 utilizes a shift-and-add technique. The shift-and-add technique utilizes information about the depth of sub-object(s) 52 along the z-axis that is reflected in the parallax captured by the plurality of projection images, as described above. According to this example embodiment, an image slice is reconstructed by first spatially shifting each projection image by an amount that is geometrically related to the distance between the image slice and the focal spot 122 along the z-axis. The shifted projection images are then averaged together to result in the image slice, where all sub-objects 52 in the plane of the image slice are in focus and sub-objects 52 outside of that plane are out of focus and blurry. This shift-and-add process is repeated for each image slice to be reconstructed. In the case of the image slice corresponding to the x-y plane that includes the focal spot 122, the projection images are averaged together without first shifting because sub-objects 52 are already in focus for that plane.

The foregoing describes a basic shift-and-add reconstruction technique. In one example embodiment herein, a deblurring technique that substantially reduces or removes blurry, out-of-plane sub-objects from an image slice can be performed in conjunction with the reconstruction technique (whether shift-and-add or another technique). Examples of deblurring techniques that can be employed include, for example, spatial frequency filtering, ectomography, filtered backprojection, selective plane removal, iterative restoration, and matrix inversion tomosynthesis, each of which may be used in Step S304 to deblur images reconstructed by the shift-and-add reconstruction technique (or another reconstruction technique, if employed).

In another example embodiment herein, Step S304 also can include the computer system 106 performing further automated image enhancements such as, for example, image sharpening, brightness optimization, and/or contrast optimization, on each reconstructed (and deblurred, where deblurring is performed) image slice in a known manner.

Additionally, in another example embodiment herein, the dimensions, position, and orientation of each image slice reconstructed in Step S304 are the same as the corresponding characteristics of the orthogonal projection image. Thus, when tomosynthesis image slices (or portions thereof) and the orthogonal projection image are overlaid over one another, corresponding anatomical features appearing in the images will be overlapped and aligned without scaling, rotation, or other transformation of the images.

In Step S306, the computer system 106 assembles the tomosynthesis image slices into an ordered stack of two-dimensional tomosynthesis images slices. Each image slice is assembled into the stack according to its corresponding location in object 50 along the z-axis, such that the image slices in the stack are ordered along the z-axis in the order of such locations along that axis. Each image slice is associated with an image number representing the position of that image in the ordered stack. For example, in a stack of sixty tomosynthesis image slices assembled from sixty tomosynthesis image slices, image number one can be the image slice closest to the x-ray detector 102 and image number sixty can be the image slice farthest from the x-ray detector 102. In one example embodiment herein, images of the plurality of projection images and image slices of the tomosynthesis stack have the same dimensional resolution and color depth characteristics.

After Step S306, control passes to Step S310, which will be described below. Before describing that step, Step S308 will first be described. Like Step S304, Step S308 is performed after Step S302 is performed.

In Step S308, the orthogonal projection image is extracted from the plurality of projection images acquired in Step S302. Because, as described above, the orthogonal projection image is defined as the projection image captured while the x-ray source 104 is in the 0° scan angle position, no reconstruction is necessary to extract that image. In one example embodiment herein, the orthogonal projection image is extracted and stored in the main memory 232, although it may be stored instead in the secondary memory 234, and can be retrieved therefrom for display in Step S310 and/or Step S322. In another example embodiment herein, the extracted orthogonal projection image may undergo automated image enhancements (performed by computer system 106) such as, for example, image sharpening, brightness optimization, and/or contrast optimization, in a known manner.

Figure 10:
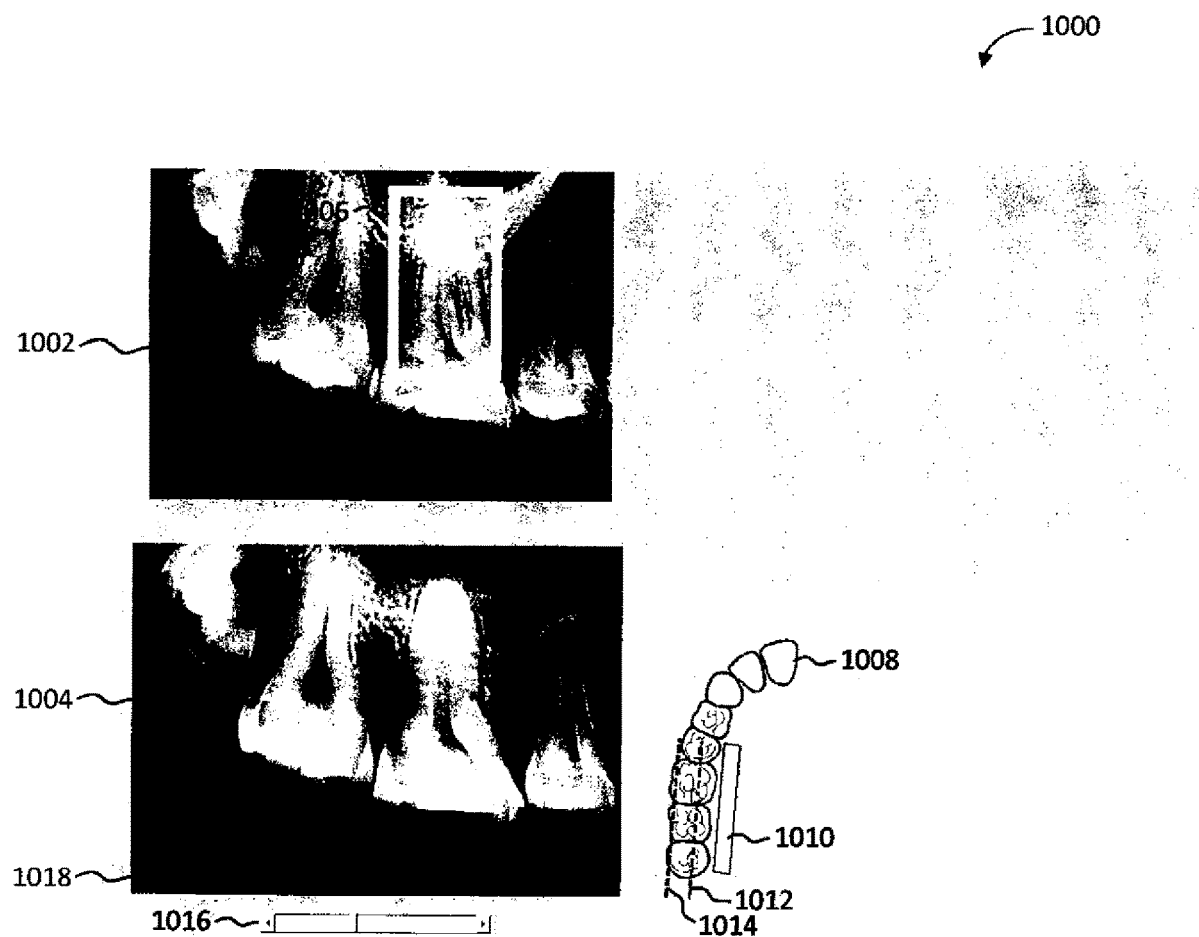
FIG. 10 illustrates an example user interface that displays high-focus tomosynthesis image slices according to an example embodiment herein.

In Step S310, the stack of tomosynthesis image slices assembled in Step S306 and the orthogonal projection image extracted in Step S308 are displayed on the display unit 108. In one example embodiment herein, the displaying can be performed as to show the entire stack, or one or more selected image slices of the stack, using display unit 108, and interactive controls (e.g. via display unit 108 and/or input device 114) enable a user to select between those two options, and to select one or more image slices for display, and also to select one or more particular regions of interest in the image(s) for display (whether in zoom or non-zoom, or reduced fashion). In a further example embodiment, as described below, stack controls 1016 illustrated in FIG. 10 are provided and can include a scroll bar, which enables the user to manually select which image slice is displayed on the display unit 108, and/or can include selectable control items, such as play, pause, skip forward, and skip backward, (not shown) to enable the user to control automatic display of the tomosynthesis stack, as a cine loop for example, on the display unit 108.

In Step S312, the computer system 106 receives, via input unit 114 and/or display unit 108, an indication of a region of interest from a user. In one example embodiment herein, the user indicates a region of interest on the orthogonal projection image displayed on the display unit 108 in Step S310. In an alternative example embodiment herein, the user indicates a region of interest on a tomosynthesis image slice displayed on the display unit 108 in Step S310.

Figure 4:
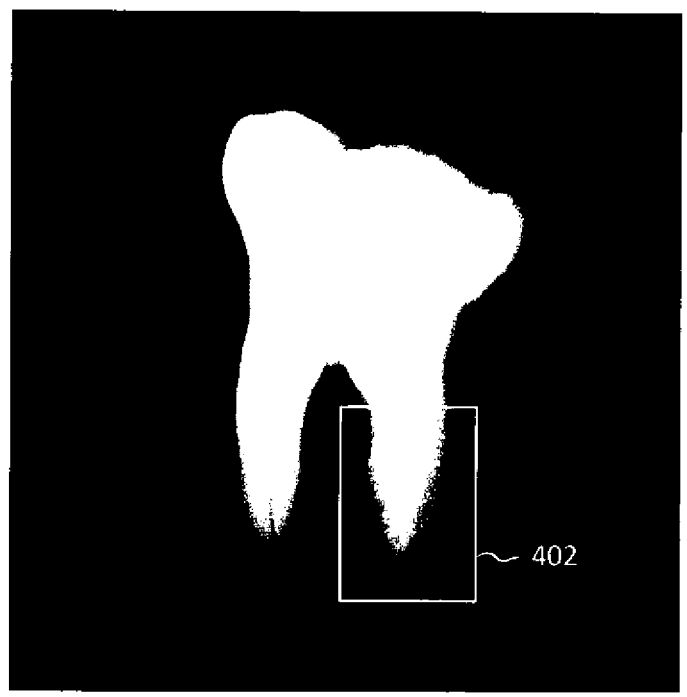
FIG. 4 illustrates an example orthogonal projection image of a tooth and a region of interest indication thereon.

Additionally, the region of interest may be a rectangular marquee (or any other outlining tool, including but not limited to a hand-drawn outline, a marquee of a predetermined shape, and the like) drawn on the orthogonal projection image or tomosynthesis image slice displayed on the display unit 108 in Step S310. For example, FIG. 4 illustrates an example of a rectangular region of interest 402 drawn over an example orthogonal projection image, although this example is not limiting.

In Step S314, the computer system 106 applies a focus function to determine the degree to which the region of interest of each image slice in the tomosynthesis stack is in focus and assigns a focus factor to each image slice based on the results of the focus function. In one example embodiment herein, prior to applying the focus function, the computer system 106 pre-processes image slices in the tomosynthesis stack to reduce image artifacts, such as ringing, motion blur, hot-pixels, and x-ray generated noise. In a further example embodiment herein, the image pre-processing includes applying a Gaussian blur filter to each image slice in a known manner.

After pre-processing image slices, if performed, the computer system 106 applies the focus function to each image slice in the tomosynthesis stack. For example, first, the computer system 106 extracts a region of interest image, which is a portion of the tomosynthesis slice image corresponding to the region of interest received in Step S312. Then, the region of interest image is padded on all sides to avoid or substantially minimize possible creation (if any) of image processing artifacts in a border region during subsequent processing in Step S312, including the deriving of a variance image as described below. The pixel values of the padding may be, for example, a constant value (e.g., zero), an extension of the border pixels of the region of interest image, or a mirror image of the border pixels of the region of interest image. After the region of interest image has been padded, a variance image is derived by iterating a variance kernel operator, for example, a 5×5 pixel matrix, through each pixel coordinate of the region of interest image. At each iterative pixel coordinate, the statistical variance of pixel values of the region of interest image within the variance kernel operator is calculated, and the result is assigned to a corresponding pixel coordinate in the variance image. Then, the variance image is cropped to the same size as that of the unpadded region of interest image. Lastly, the focus factor is calculated as the statistical mean of the pixel values in the cropped variance image. Accordingly, a high focus factor corresponds to a high mean variance within the region of interest image. The focus factor is assigned to the image slice, and correspondingly, the focus factor is associated with the image number of the image slice to which it is assigned. The foregoing process is applied to each slice, for example, by serial iteration and/or in parallel, to assign a focus factor to each image slice.

In the preceding example embodiment, performing the focus function on the region of interest portion of each image slice instead of on the full view of each image slice facilitates the process of FIG. 3 in identifying the z-axis location of images slices that are in high focus within the region of interest relative to other images slices. The focus function can be performed on the full view of image slices; however, focusing techniques performed on the full view may, in at least some cases, function less effectively to identify the location of high-focus images, because the full view of most, if not all, image slices contains both in-focus and out-of-focus regions.

Figure 5:
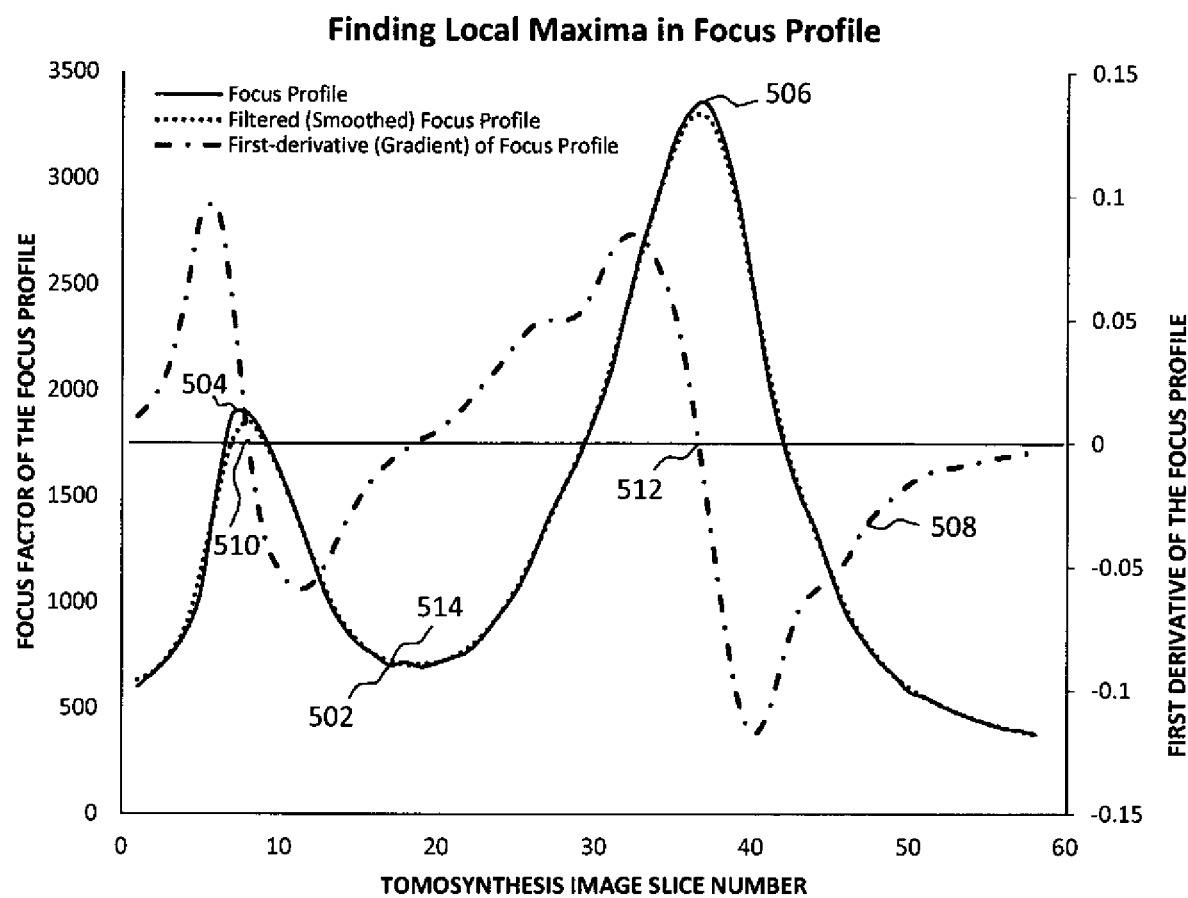
FIG. 5 illustrates an example focus profile within the region of interest of the tooth of FIG. 4.

In Step S316, the computer system 106 creates a focus profile from a series of the focus factors assigned in Step S314, where the focus factors are ordered in the focus profile according to their corresponding image numbers. FIG. 5 illustrates an example focus profile 502 (shown as a solid line) within the region of interest 402 of FIG. 4. The focus profile 502 of FIG. 5 is shown as a graph plotting the focus factor on the left side y-axis for each image slice number on the x-axis.

In Step S318, the computer system 106 searches for a local extremum in the focus profile (i.e., a local maximum or a local minimum), using known techniques. A focus profile may have more than one local extremum. For example, FIG. 5 illustrates, in addition to the example of the focus profile 502, local maxima 504 and 506 identified as a result of Step S318 being performed.

In one example embodiment herein, the computer system 106 compares each focus factor to its neighbors iteratively, wherein neighbors are defined as the focus factors within a predetermined range of image numbers of the focus factor being evaluated during an iteration. If the focus factor being evaluated is greater than the individual focus factors of all of its neighbors, the focus factor being evaluated is designated a local maximum; otherwise, it is not designated a local maximum.

In another example embodiment herein, the computer system 106 performs a first derivative test to search for the local maximum of the focus profile. A first derivative of the focus profile is calculated from the focus profile (e.g., calculating a difference value at each image number of the focus profile by subtracting the focus factor at one image number from the focus factor of the next greater image number), and then the local maximum is identified as corresponding to the image number where the first derivative of the focus profile crosses zero from positive to negative. For example, FIG. 5 illustrates a first derivative 508 (shown as a dot-dash line, with magnitude of the first derivative on the right side y-axis) corresponding to the focus profile 502. Local maxima 504 and 506 are identified as corresponding to first derivative zero crossings 510 and 512, respectively, as a result of performing Step S318 according to an example of the present embodiment.

In a further example embodiment herein, the focus profile is filtered, that is, smoothed, by a moving average before searching for a local maximum in the focus profile. FIG. 5 illustrates a filtered (smoothed) focus profile 514 (shown as a dotted line) corresponding to the focus profile 502. The size of the moving average sample window may be, for example, three neighboring focus factors. For some focus profiles, smoothing may improve the accuracy of the local maximum search.

In Step S320, the computer system 106 identifies the image number corresponding to the local maximum identified in Step S318 and extracts the image slice associated with that identified image number from the stack of tomosynthesis images for display in Step S322. The extracted image slice is also referred to herein as a high-focus image, because it has a greater focus factor (that is, it is in greater focus) than other nearby image slices, as determined in Step S318. In one example embodiment herein, the high-focus image is extracted and stored in the main memory 232, although it may be stored instead in the secondary memory 234, and can be retrieved therefrom for display in Step S322.

Figure 6:
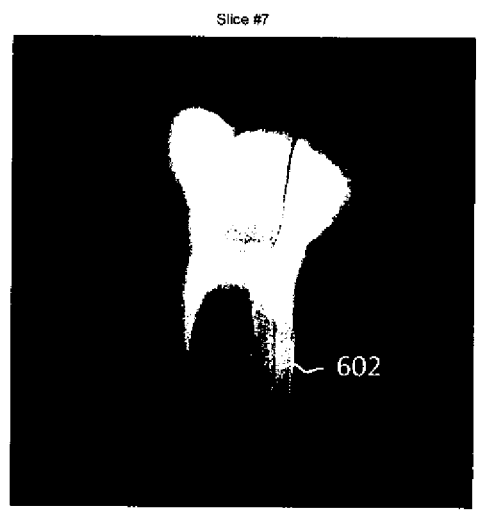
FIG. 6 illustrates an example high-focus tomosynthesis image slice of the tooth of FIG. 4.
Figure 7:
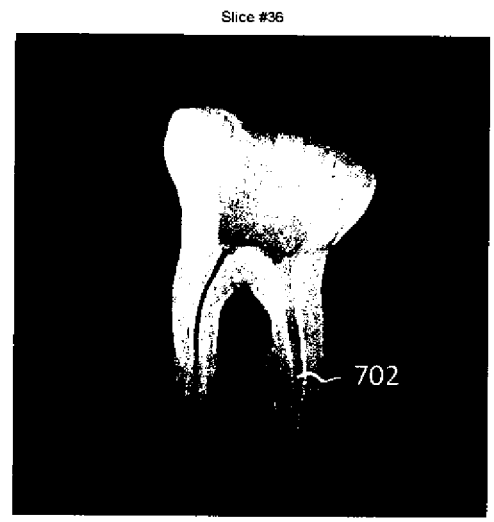
FIG. 7 illustrates another example high-focus tomosynthesis image slice of the tooth of FIG. 4.

In the case where more than one local maximum is found in Step S318, more than one high-focus image corresponding to those local maxima are extracted. In an example embodiment herein, the high-focus images show one or more sub-object(s) 52 with clarity, by virtue of the processing performed in Steps S314, S316, and S318, even though the sub-object(s) 52 may not be visible in the conventional orthogonal projection image. This is because the presence of in-focus sub-object(s) 52 (e.g., anatomical features) in a high-focus image generally corresponds to a high mean variance in the region of interest of that high-focus image, and the high mean variance can be identified as a local maximum in Step S320. For example, FIGS. 6 and 7 illustrate examples of image slices extracted by performing Step S320. First, local maxima 502 and 504 in FIG. 5 are identified as corresponding to image numbers 7 and 36 in the tomosynthesis stack. In FIGS. 6 and 7, which correspond to image numbers 7 and 36, respectively, clearly defined root structures 602 and 702 can be seen, where those structures appear more clearly than in the orthogonal projection image shown on FIG. 4.

Figure 8:
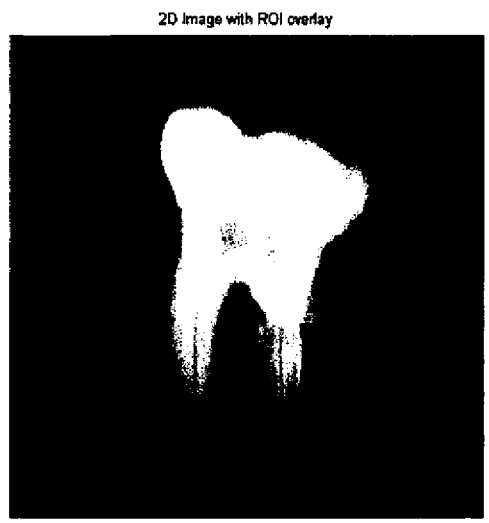
FIG. 8 illustrates the example orthogonal projection image of FIG. 4 with a portion of FIG. 6 overlaid thereon within the region of interest.
Figure 9:
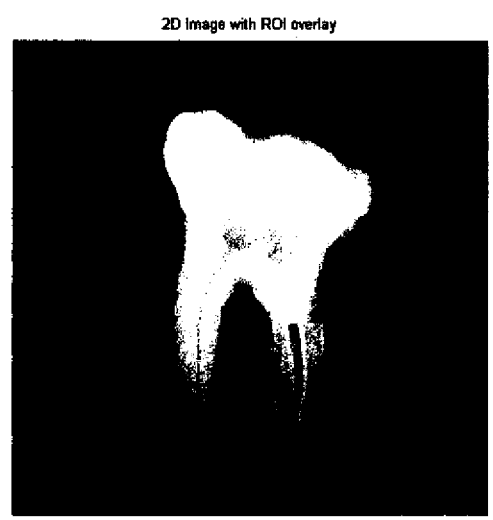
FIG. 9 illustrates the example orthogonal projection image of FIG. 4 with a portion of FIG. 7 overlaid thereon within the region of interest.

In Step S322, the computer system 106 displays the high-focus image(s) extracted in Step S320 on the display unit 108. In one example embodiment herein, the display unit 108 displays a composite image comprising a portion of the high-focus image extracted in Step S320, overlaid on the orthogonal projection image extracted in Step S308. The composite image is formed by using the region of interest received in Step S312 to select a corresponding portion of the high-focus image extracted in Step S320. The portion of the high-focus image is then overlaid on the region of interest indicated in Step S312 of the orthogonal projection image extracted in Step S308. For example, in the example embodiment described above in Step S304 where each image slice and the orthogonal projection image have the same dimensions, position, and orientation, the region of interest indicated in Step S312 corresponds to the same pixel locations in both the high-focus images extracted in Step S320 and the orthogonal projection image extracted in Step S308. In the case where more than one high-focus image is extracted in Step S320, more than one composite image can be displayed in Step S322. For example, FIGS. 8 and 9 illustrate examples of the orthogonal projection image shown in FIG. 4 with the region of interest portions from the high-focus images of FIGS. 6 and 7, respectively, overlaid thereon.

In another example embodiment herein, displaying the high-focus image(s) in Step S322 can also include displaying a user interface on display unit 108, with which the user may interact via input unit 114 and/or display unit 108. FIG. 10 illustrates an example of such a user interface 1000. The user interface 1000 can display an orthogonal projection image in an orthogonal projection image viewport 1002. A region of interest 1006 can be visually depicted in the orthogonal projection image viewport 1002 and can be the same region of interest obtained from the user in Step S312.

The user interface 1000 can also display, in a tomosynthesis image viewport 1004, the entire stack of tomosynthesis image slices, or one or more selected image slices of the stack. Stack controls 1016 can be provided to enable the user to manually select, via a scroll bar for example, which image slice of the tomosynthesis stack to display on the tomosynthesis image viewport 1004. In another example embodiment herein, the stack controls 1016 may include selectable control items, such as, for example, play, pause, skip forward, and skip backward, (not shown), or the like, to enable the user to control automatic display of the tomosynthesis stack, as a cine loop for example, on the tomosynthesis image viewport 1004. An image location indicator 1018 also can be provided to indicate to where in object 50 along the z-axis relative to the x-ray detector 102 the image slice appearing in the tomosynthesis image viewport 1004 corresponds. The location along the z-axis of the image slice appearing in the tomosynthesis image viewport 1004, represented by the image location indicator 1018, is known, because, as described above, the location of each image slice in the stack of tomosynthesis image slices reconstructed in Step S304 was provided as an input to the tomosynthesis image reconstruction process of that step. In an alternative embodiment herein, the z-axis location represented by the image location indicator 1018 can be calculated (e.g., by the computer system 106 or the computer processor 222) by multiplying the image number of the image appearing in the tomosynthesis image viewport 1004 by the z-axis slice thickness, which is a function of the known geometry of the system (e.g., the scan angle 112).

The user interface 1000 can also include pictorial indicators to help the user navigate the stack of tomosynthesis image slices, such as, for example, a representation of the imaged object 1008 (which is a pictorial representation of object 50), an x-ray detector icon 1010 (placed in relation to the representation of the imaged object 1008 to indicate the placement of x-ray detector 102 relative to object 50 in Step S302), and high-focus image indicator lines 1012 and 1014 within the imaged anatomy 1008 (which are pictorial representations that indicate the z-axis location within object 50 of high-focus images identified and extracted in Step S320).

The number of high-focus image indicator lines appearing on the user interface 1000 corresponds with the number of high-focus images extracted in Step S320. For example, in FIG. 10, two high-focus image indicator lines 1012 and 1014 are shown, representing two high-focus images extracted in Step S320 and illustrated in the examples of FIGS. 6 and 7, respectively. In one example embodiment herein, selecting a high-focus image indicator line will display the corresponding high-focus image identified and extracted in Step S320 in the tomosynthesis image viewport 1004.

The process of FIG. 3 ends at Step S324.

Clinician users are accustomed to reading conventional two-dimensional x-ray images due to their long-established use in medicine, but 3D datasets may be less familiar and more difficult to analyze. It can be appreciated that automated extraction of information from a 3D tomographic dataset, including the identification within the 3D tomographic dataset of high-focus images that contain features of interest (e.g., anatomical features), and presentation of the extracted information to a user may be useful. A clinician user may find it more intuitive to have a portion of the high-focus image, which shows the feature of interest, overlaid on and within the context of the two-dimensional orthogonal projection image, with which they are accustomed from long-established practice. Additionally, automated presentation of the extracted information can save the clinician user the time and effort associated with manually scrolling through and analyzing a large number of image slices in order to locate features of interest.

Reducing Image Reconstruction Artifacts

Figure 17A:
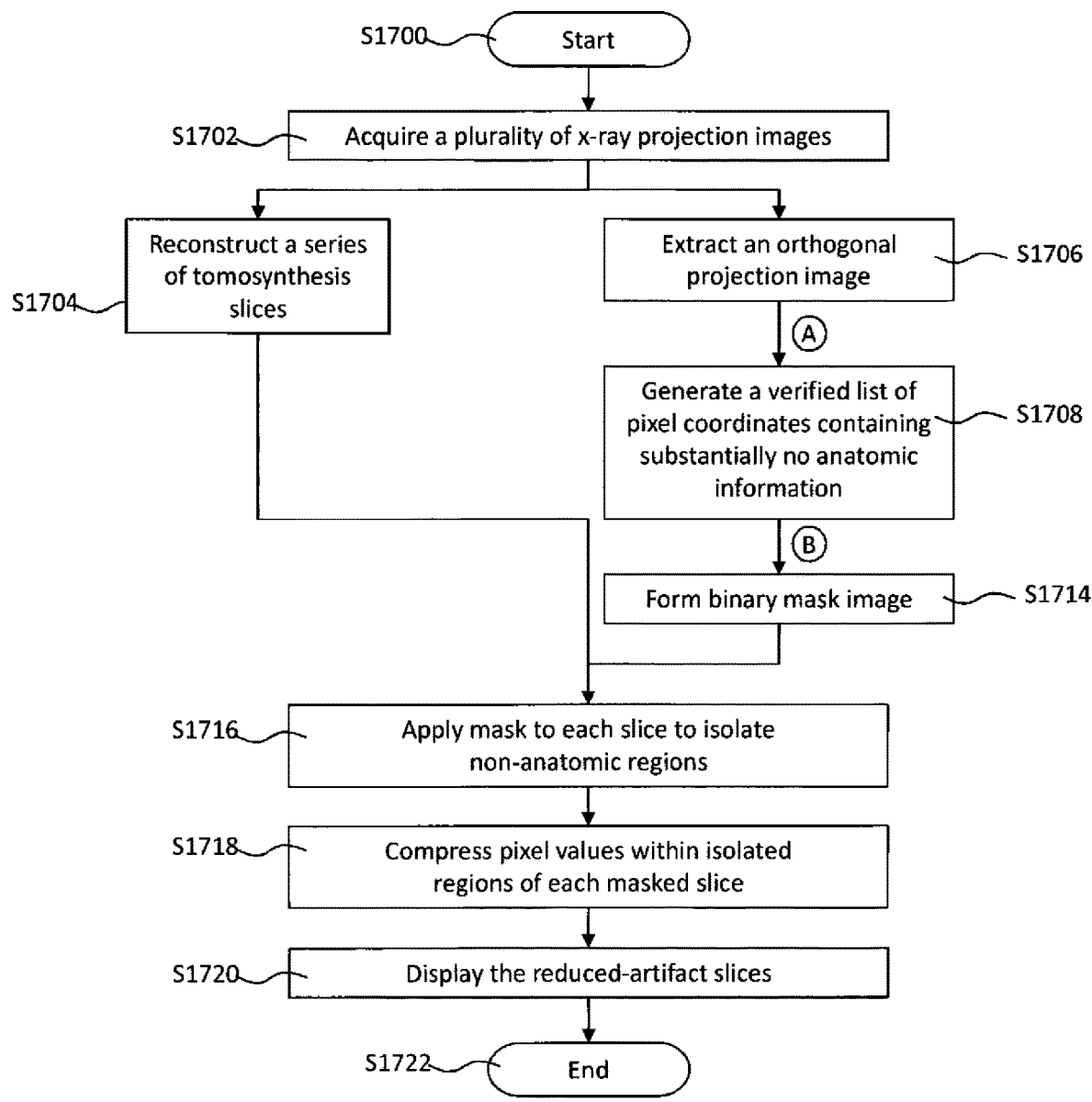
FIG. 17A is a flowchart illustrating a process for generating a mask based on a two-dimensional orthogonal projection image and using the mask to guide a process for reducing image reconstruction artifacts in an intraoral tomosynthesis dataset according to an example embodiment herein.

The above intraoral tomosynthesis system 100 will now be further described in conjunction with FIG. 17A, which shows a flow diagram of a process according to an example embodiment herein for using a mask based on a two-dimensional orthogonal projection image to guide a process for reducing image reconstruction artifacts in an intraoral tomosynthesis dataset.

Prior to starting the process, the x-ray detector 102 and x-ray source 104 are aligned manually by a user to a starting position, as described above, in one example embodiment herein.

The process of FIG. 17A starts at Step S1700, and in Step S1702 the intraoral tomosynthesis system 100 acquires a plurality of projection images of object 50 over a scan angle 112 (which may be predetermined), including the orthogonal projection image, in the manner described above. For example, the x-ray source 104 is moved by the motorized stage 116 and control circuitry 118 to different positions within the scan angle 112, and the computer system 106 controls the x-ray source 104 to emit x-rays 110 at each position. In one example embodiment herein, x-ray source 104 is scanned, by pivoting at a point along the z-axis, from −20° from the z-axis to +20° from the z-axis in evenly distributed increments of 0.8° to provide 51 scan angles, including the 0° position, although this example is not limiting. The x-rays 110 then pass through and are attenuated by the object 50 before being projected onto the x-ray detector 102. The x-ray detector 102 converts the x-rays 110 into electrical signals (either directly or indirectly, as described above) and provides the electrical signals to the computer system 106. The computer system 106 processes the electrical signals collected at each scan angle position to acquire the plurality of projection images, each image comprising an array of pixels. The image acquired with the x-ray source 104 at the 0° position is also referred to herein as an orthogonal projection image.

In one example embodiment herein, the color depth of each pixel value of the projection images may be 12-bit grayscale, and the dimensions of the projection images correspond to the standard dental size of the x-ray detector 102, as described above. For example, a Size-2 detector may produce projection images that are approximately 1700×2400 pixels in size, a Size-1 detector may produce projection images that are approximately 1300×2000 pixels in size, and a Size-0 detector may produce projection images that are approximately 1200×1600 pixels in size.

In Step S1704, the computer system 106 processes the plurality of projection images acquired in Step S302 using a reconstruction technique in order to reconstruct a series of two-dimensional tomosynthesis image slices and may also perform deblurring and other image enhancements, as will be described further herein. Each reconstructed image slice is a tomographic section of object 50 comprising an array of pixels (each pixel being located at a pixel coordinate), that is, each image slice represents a cross-section of object 50 that is parallel to the x-y plane in which the receiving surface of the x-ray detector 102 extends, has a slice thickness along the z-axis, and is positioned at a different, respective location along the z-axis than other image slices. The slice thickness is a function of the reconstruction technique and aspects of the geometry of the system 100, including, primarily, the scan angle 112. For example, each image slice may have a slice thickness of 0.5 mm by virtue of the geometry of the system 100 and the reconstruction technique. The desired location of each reconstructed image slice along the z-axis is provided as an input to the reconstruction performed in Step S304 either as a pre-programmed parameter in computer system 106 or by user input via input unit 114 and/or display unit 108. By example only, the computer system 106 can be instructed to reconstruct, from the plurality of projection images, a first image slice that is one millimeter (1 mm) away from the surface of x-ray detector 102 along the z-axis, a last image slice being at fifteen millimeters (15 mm) away from the surface of the x-ray detector 102, and image slices between the first image slice and the last image slice at regular increments along the z-axis of two-hundred micrometers (200 μm), for a total of seventy-one image slices.

Reconstruction of the tomosynthesis image slices in Step S1704 may be performed in accordance with any existing or later developed reconstruction technique. In one example embodiment herein, reconstruction of the tomosynthesis image slices in Step S1704 utilizes a shift-and-add technique, described above. The shift-and-add technique utilizes information about the depth of sub-object(s) 52 along the z-axis that is reflected in the parallax captured by the plurality of projection images, as described above. According to this example embodiment, an image slice is reconstructed by first spatially shifting each projection image by an amount that is geometrically related to the distance between the image slice and the tomographic focal spot 122 along the z-axis. The shifted projection images are then averaged together to result in the image slice, where all sub-objects 52 in the plane of the image slice are in focus and sub-objects 52 outside of that plane are out of focus and blurry. This shift-and-add process is repeated for each image slice to be reconstructed. In the case of the image slice corresponding to the x-y plane that includes the tomographic focal spot 122, the projection images are averaged together without first shifting because sub-objects 52 are already in focus for that plane.

The foregoing describes a basic shift-and-add reconstruction technique. In one example embodiment herein, a deblurring technique that substantially reduces or removes blurry, out-of-plane sub-objects from an image slice can be performed in conjunction with the reconstruction technique (whether shift-and-add or another technique). Examples of deblurring techniques that can be employed include, for example, spatial frequency filtering, ectomography, filtered backprojection, selective plane removal, iterative restoration, and matrix inversion tomosynthesis, each of which may be used in Step S1704 to deblur images reconstructed by the shift-and-add reconstruction technique (or another reconstruction technique, if employed).

In another example embodiment herein, Step S1704 also can include the computer system 106 performing further automated image enhancements such as, for example, image blurring, image sharpening, brightness optimization, and/or contrast optimization, on each reconstructed (and deblurred, where deblurring is performed) image slice in a known manner.

Additionally, in another example embodiment herein, the dimensions, position, and orientation of each image slice reconstructed in Step S1704 are the same as the corresponding characteristics of the orthogonal projection image. Thus, when tomosynthesis image slices (or portions thereof) and the orthogonal projection image are overlaid over one another, corresponding anatomical features appearing in the images will be overlapped and aligned without scaling, rotation, or other transformation of the images.

After Step S1704, control passes to Step S1716, which will be described below. Before describing that step, Steps S1706, S1708, and S1714 will first be described. Like Step S1704, Step S1706 is performed after Step S1702 is performed. (However, in other embodiments herein, Step S1704 is performed serially between Steps S1702 and S1706, and then the method continues from Step S1706 as shown in FIG. 17A. That is, control passes from Step S1702 to Step S1704, and then from Step S1704 to Step S1706, in which case, control does not pass from Step S1704 to Step S1716 as shown in FIG. 17A. In yet other example embodiments herein, Step S1704 is performed serially between Steps S1714 and Step S1716, instead of the order shown in FIG. 17A. That is, control passes from Step S1702 to Step S1706, at which point the method is performed until Step S1714 according to FIG. 17A, then control passes from Step S1714 to Step S1704, and then control passes from Step S1704 to Step S1716, but control does not pass from Step S1702 to Step S1704 as shown in FIG. 17A.)

Figure 18:
FIG. 18 illustrates an example orthogonal projection image.

Referring again to the embodiment represented in FIG. 17A, in Step S1706, the orthogonal projection image is extracted from the plurality of projection images acquired in Step S1702. Because, as described above, the orthogonal projection image is defined as the projection image captured while the x-ray source 104 is in the 0° scan angle position, no reconstruction is necessary to extract that image. In one example embodiment herein, the orthogonal projection image is extracted and stored in the main memory 232, although it may be stored instead in the secondary memory 234. For example, FIG. 18 illustrates an example orthogonal projection image.

In Step S1708, the orthogonal projection image extracted in Step S1706 is received as input and processed to generate as output a verified list of pixel coordinates of the orthogonal projection image that do not contain a predetermined type of information, e.g., anatomic or diagnostic information (such regions are hereinafter referred to as "non-anatomic regions" for convenience). Non-anatomic regions correspond to, in the imaged volume, air gaps, air pockets, and/or a mechanism for holding the x-ray detector 102, for example.

Step S1708 can be performed in different ways according to various example embodiments herein, including, but not limited to, either of the subprocesses illustrated in FIGS.

17B and 17C. The subprocesses shown in FIGS. 17B and 17C will now be described in turn.

Figure 17B:
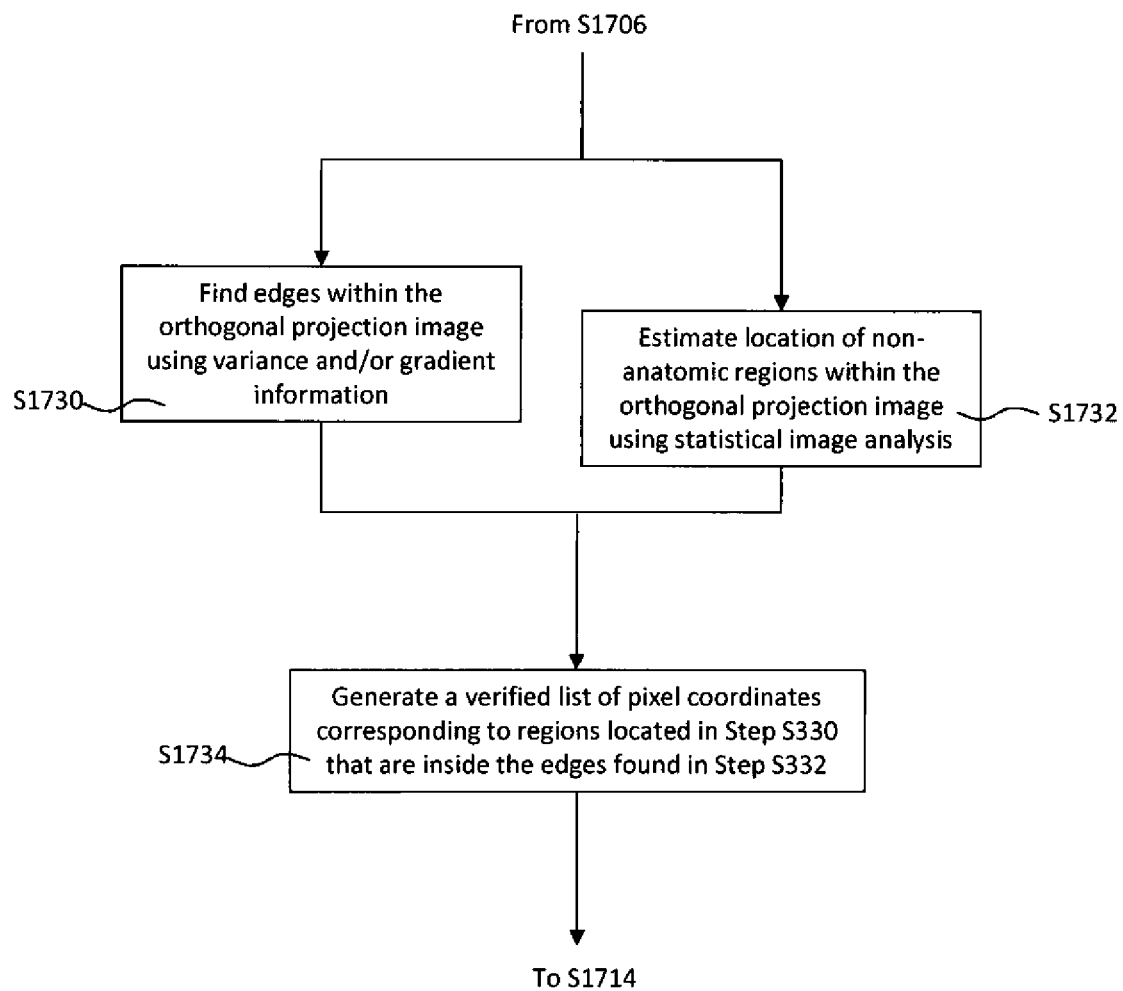
FIG. 17B is a flowchart illustrating a subprocess of FIG. 17A, namely features of step S1708 of FIG. 17A, according to an example embodiment herein.

In one example embodiment herein, Step S1708 (FIG. 17A) may be performed according to the subprocess illustrated in FIG. 17B. The subprocess of FIG. 17B starts in Step S1730, object edges within the orthogonal projection image extracted in Step S1706 are detected by deriving at least one edge map from the orthogonal projection image and comparing the edge map to a threshold, in a manner described below. The edge map can be a variance image, a gradient image, or a combination thereof, and, in one example, the variance image and the gradient image can be derived by applying, respectively, a variance kernel operator and a gradient kernel operator to the orthogonal projection image extracted in Step S1706 in a manner described in greater detail below. The sensitivity of the variance and gradient kernel operators to edges, and the width of the detected edges on the variance and gradient images, can be adjusted by tuning the parameters of the operators. Additionally, after deriving the edge map but prior to comparing the edge map to a threshold, Step S1730 may also include a sub step of closing incomplete edges within the edge map, as will be described further below. Object edges detected in Step S1730 are characterized by a high spatial frequency (i.e., a sharp transition) and are typically associated with boundaries of objects of interest in an image.

Figure 19:
FIG. 19 illustrates a variance image corresponding to the orthogonal projection image of FIG. 18.

A variance image (mentioned above) can be derived in Step S1730 by iterating a variance kernel operator, for example, a 5×5 pixel matrix, through each pixel coordinate of the orthogonal projection image. At each iterative pixel coordinate, the statistical variance of pixel values of the orthogonal projection image within the variance kernel operator is calculated, and the result is assigned to a corresponding pixel coordinate in the variance image. Because variance represents the degree to which the value of a pixel varies from those of its neighbors, high spatial frequency regions, such as an object edge, have a high variance, while smooth, low spatial frequency regions have a low variance. For example, FIG. 19 illustrates a variance image derived from the orthogonal projection image illustrated in FIG. 18.

A gradient image (mentioned above) can be derived in Step S1730 by iterating a gradient kernel operator through each pixel coordinate of the orthogonal projection image. At each iterative pixel coordinate, the gradient kernel operator is convolved with pixel values of the orthogonal projection image at that pixel coordinate, and the result is assigned to a corresponding pixel coordinate in the gradient image. Examples of well-known gradient kernel operators include Roberts, Prewitt, and Sobel operators.

Figure 20:
FIG. 20 illustrates a gradient image corresponding to the orthogonal projection image of FIG. 18.

Because the gradient represents the magnitude of directional change in pixel value at a given pixel relative to its neighbors, a region with a greater directional change in pixel value, such as an object edge, will have a greater corresponding gradient value than a region with no change or non-directional change. For example, FIG. 20 illustrates a gradient image derived from the orthogonal projection image illustrated in FIG. 18.

In one example embodiment herein, the variance image and the gradient image may individually serve as edge maps, and may be derived simultaneously or sequentially. In yet other example embodiments herein, only one of the variance image and the gradient image serves as an edge map. In a further example embodiment herein, the edge map is derived by combining the variance image and the gradient image by way of a logic operator (e.g., AND, OR, etc.).

After the edge map is derived in Step S1730, Step S1730 may, in one example embodiment herein, further include a substep of closing incomplete edges within the edge map (also known as edge linking). The edge map may have incomplete edges due to a number of factors, including, for example, noise or discontinuities in the pixel values of the orthogonal projection image, the parameters of the variance and gradient kernels, and/or the threshold applied to the edge map. Incomplete edges can be closed according to mathematical techniques and/or localized curve fitting methods.

Finally, edges are extracted in Step S1730 by identifying pixels in the edge map that are greater than a threshold. The value of the threshold may depend on whether the edge map corresponds to the variance image, the gradient image, or a logical combination thereof. Furthermore, adjusting the threshold allows for control over the sensitivity to edges and the width of the detected edges, and thus it also is within the scope of the method of FIGS. 17A and 17B to employ an adjustable threshold in the edge extraction, wherein the threshold is adjusted based on predetermined criteria over iterations of edge extractions.

After Step S1730 is performed, control passes to Step S1734, which will be described below. Before describing that step, Step S1732 will first be described. Like Step S1730, Step S1732 is performed after Step S1706 (of FIG. 17A) is performed. (However, in other embodiments herein, Steps S1730 and S1732 can be performed serially. For example, instead of the order shown in FIG. 17B, in another example embodiment herein, Step S1730 is performed before Step S1732 (i.e., in between steps S1706 and S1732), whereas in another example embodiment herein, Step S1732 is performed before Step S1730 (i.e., in between steps S1706 and S1730)).

In Step S1732, image statistics of the orthogonal projection image (extracted in Step S1706) as a whole, including, for example, a mean pixel value, a median pixel value, a pixel value histogram, and a pixel value cumulative histogram, are calculated and used to estimate the locations of non-anatomic regions of the orthogonal projection image. As mentioned above, non-anatomic regions correspond to, in the imaged volume, air gaps, air pockets, and/or a mechanism for holding the x-ray detector 102, for example. Because no anatomy is present in these regions to absorb emitted x-rays 110, the detector 102 receives more x-rays 110 and outputs higher electrical signal in these regions, which appear, for example, as black or very dark areas on the projection images acquired in Step S1702. Thus, on the pixel value histogram, these non-anatomic regions have high pixel values relative to the rest of the orthogonal projection image, and may further correspond to one or more distinctive peaks at the high pixel values (such distinctive peaks in the pixel value histogram will correspond to large gradient increases in the pixel value cumulative histogram). The image statistics (e.g., the mean pixel value, the median pixel value, and the pixel value cumulative histogram) can be combined to determine a threshold point that separates pixel values corresponding to anatomy from pixel values corresponding to non-anatomy. For example, the threshold point may be specified manually by a user (via input unit 114 and/or display unit 108) or automatically by computer system 106 by selecting a pixel value that is above the median pixel value but below the distinctive peak(s). Based on the threshold point, a range of non-anatomic pixel values is deemed to correspond to regions containing no anatomic information. Finally, Step S1732 generates as an output a list of unverified non-anatomic pixel coordinates, which represents the estimated locations of non-anatomic regions of the orthogonal projection image, from the pixel coordinates of the orthogonal projection image (from Step S1706) that have pixel values within the range of non-anatomic pixel values.

Figure 21:
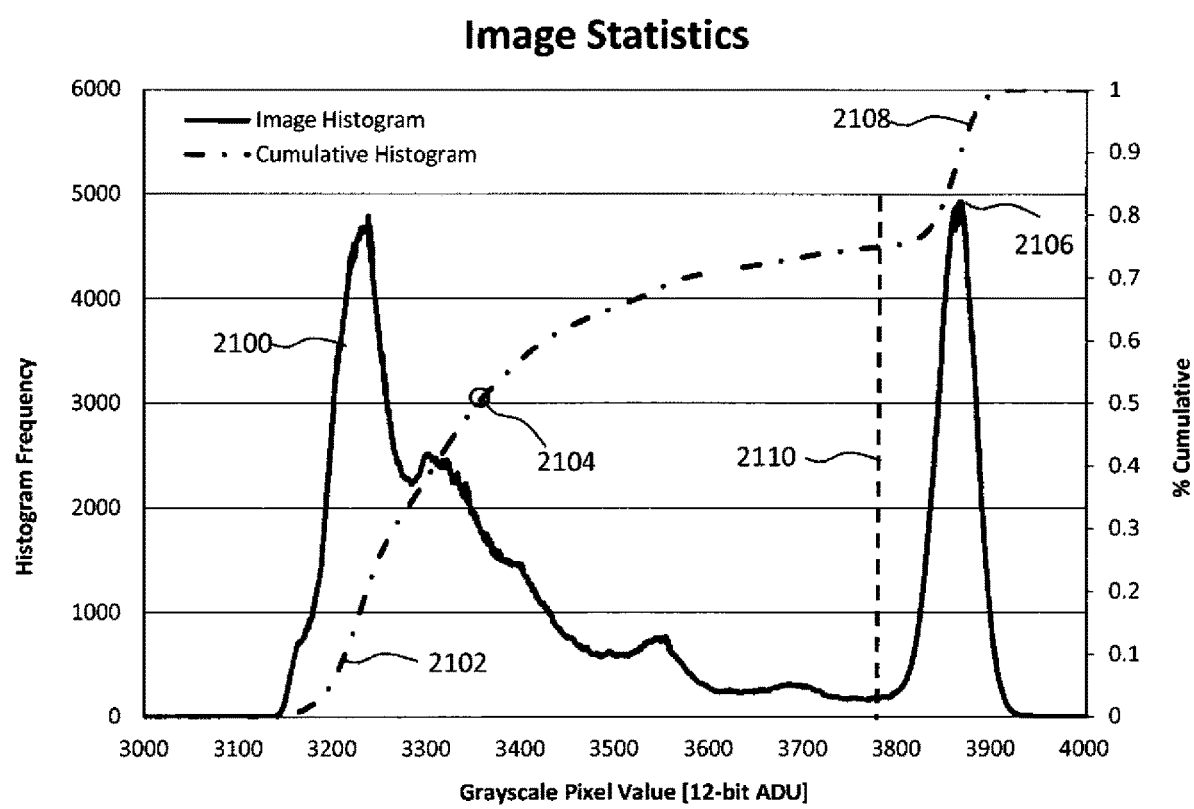
FIG. 21 illustrates image statistics corresponding to the orthogonal projection image of FIG. 18.

For example, FIG. 21 illustrates image statistics of the orthogonal projection image of FIG. 18, including a pixel value histogram 2100, a pixel value cumulative histogram 2102, a median of the cumulative histogram 2104, a distinctive histogram peak at high pixel values 2106, and a large gradient increase in the cumulative histogram at high pixel values 2108. A threshold point 2110 is determined for the example illustrated in FIG. 21 to be a pixel value of approximately 3800 based on the image statistics, and a range of non-anatomic pixel values of approximately 3800 and above is deemed to correspond to non-anatomic regions. Finally, Step S1732 outputs an unverified list (not shown) of non-anatomic pixel coordinates from the orthogonal projection image of FIG. 18 that have pixel values equal to or greater than 3800.

In certain circumstances, the list of unverified non-anatomic pixel coordinates generated in Step S1732 may imperfectly separate anatomy from non-anatomy because the threshold point determined in Step S1732 is based solely on the pixel value statistical information over the entire orthogonal projection image. That is, it may occur that some regions of the orthogonal projection image having pixel values within the range of non-anatomic pixel values (selected in Step S1732 based on the threshold point) do in-fact contain anatomic information.

Thus, in Step S1734, the computer system 106 checks which pixel coordinates of the list of unverified non-anatomic pixel coordinates generated in Step S1732 are inside a spatial boundary formed by the edges detected in Step S1730 in order to generate a list of verified non-anatomic pixel coordinates. In particular, pixel coordinates within the boundaries are deemed to be anatomic regions, while pixel coordinates outside the boundaries are deemed to be non-anatomic regions. Accordingly, pixel coordinates determined to be inside the boundaries (i.e., anatomic regions) are removed from the list, and pixel coordinates determined to be outside of the boundaries (i.e., non-anatomic regions) remain on the list, thereby providing a list of verified non-anatomic pixel coordinates that is provided to Step S1714 (FIG. 17A).

Figure 17C:
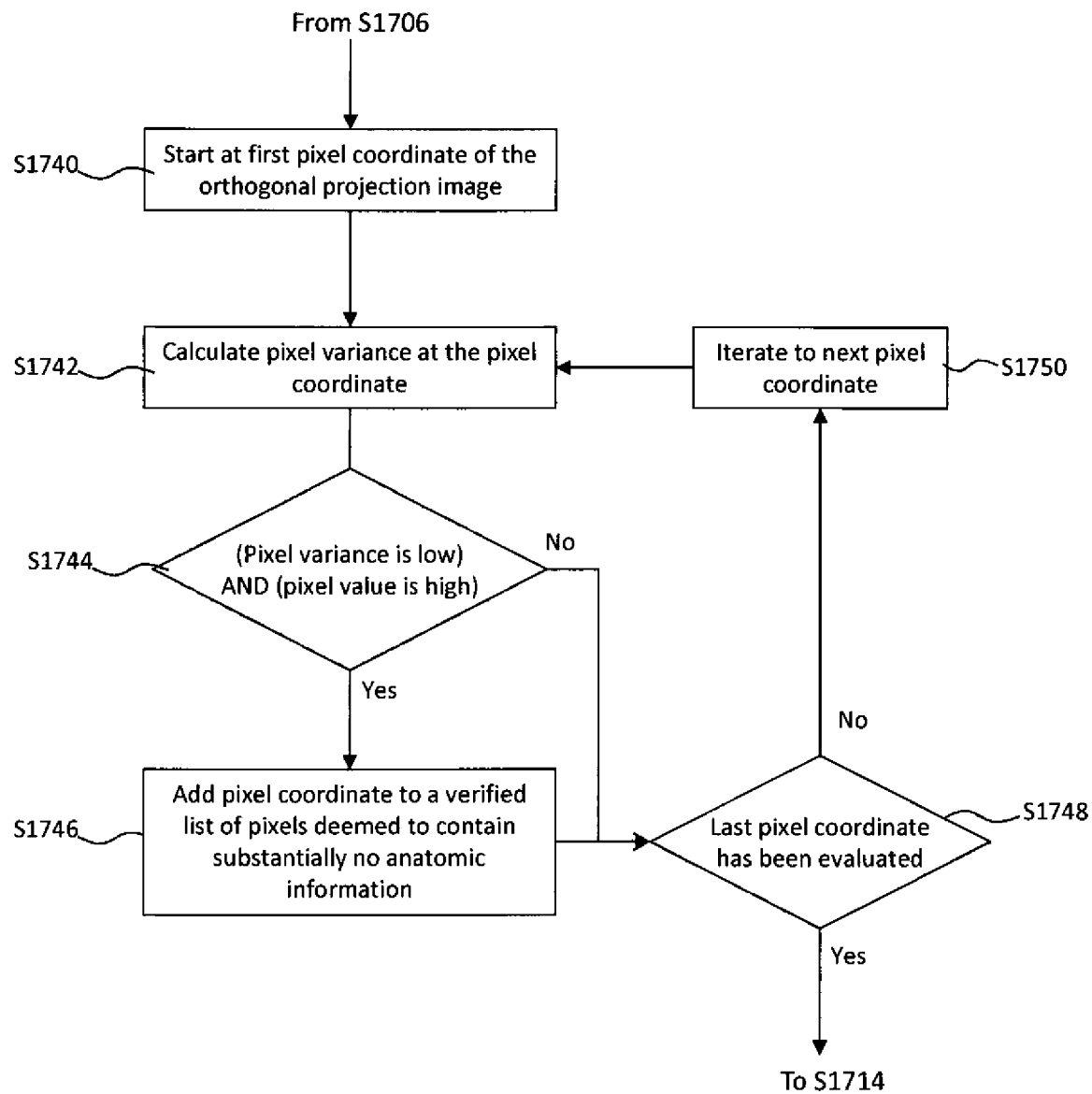
FIG. 17C is a flowchart illustrating a subprocess of FIG. 17A, namely features of step S1708 of FIG. 17A, according to another example embodiment herein.

In another example embodiment herein, Step S1708 may be performed according to the subprocess illustrated in FIG. 17C, which evaluates each pixel coordinate of the orthogonal projection image extracted in Step S1706 according to a conditional statement that states that if a pixel coordinate has a high pixel value and a low pixel variance, then that pixel coordinate contains substantially no anatomic information.

In particular, the subprocess of FIG. 17C iterates through each pixel coordinate of the orthogonal projection image extracted in Step S1706, starting with a first pixel coordinate in Step S1740. Then, in Step S1742, the pixel variance at the starting pixel coordinate is calculated, for example, by computing the statistical variance of pixel values of the orthogonal projection image within a variance kernel operator (e.g., a 5×5 pixel matrix centered on the starting pixel coordinate).

In decision block S1744, the computer system 106 evaluates whether the pixel variance calculated in Step S1742 is low (by comparing the pixel variance to a pixel variance threshold, which may be predetermined) and whether the pixel value at the pixel coordinate is high (by comparing the pixel coordinate to a pixel value threshold, which may be predetermined). If both conditions are satisfied in decision block S1744, then, in Step S1746, the pixel coordinate is added to a verified list of pixels deemed to contain substantially no anatomic information before control passes to decision block S1748. If either condition is not satisfied in decision block S1744, then control passes directly to decision block S1748.

A pixel coordinate satisfying both conditions is deemed to contain substantially no anatomic information because of the following presumptions regarding pixel variances and pixel values of the orthogonal projection image. First, areas of the orthogonal projection image containing anatomic information generally exhibit at least a moderately high pixel variance, while areas not containing anatomic information (e.g., air gaps, air pockets, or an x-ray detector holder) generally exhibit a low pixel variance. Second, as explained above with respect to Step S1732, pixel coordinates that contain no anatomic generally have high pixel values and appear black or very dark, because no anatomy is present to absorb the emitted x-rays 110. On the other hand, pixel coordinates containing anatomic information generally exhibit lower pixel values. Thus, if a pixel coordinate has both low pixel variance and high pixel value, it is deemed likely to not contain anatomic information.

In some example embodiments herein, the pixel value threshold used in decision block S1744 can be derived from image statistics of the orthogonal projection image extracted in Step S1706 as a whole, as described above with respect to Step S1732 of the subprocess illustrated in FIG. 17B.

At decision block S1748 (after decision block S1744 if "No" at decision block S1744 or after Step S1746 if "Yes" at decision block S1744), the computer system 106 checks if the last pixel coordinate in the orthogonal projection image has been evaluated by the conditional statement at decision block S1744. If the last pixel coordinate has not been evaluated yet ("No" at decision block S1748), then the subprocess continues to Step S1750, where the computer system 106 iterates to the next pixel coordinate and subsequently evaluates that next pixel coordinate in the above described manner (i.e., performs Steps S1742, S1744, S1746 if applicable, and S1748). If the last pixel coordinate has been evaluated ("Yes" at decision block S1748), then the subprocess of FIG. 17C ends by passing control and the verified list of pixels compiled in Step S1746 to Step S1714 (FIG. 17A).

It will be apparent to a person skilled in the relevant art(s) that while the subprocess of FIG. 17C is explained above on a pixel-by-pixel basis, the subprocess of FIG. 17C also can be performed by different computational techniques, including, for example, evaluating the conditional statement for the whole orthogonal projection image extracted in Step S1706 in a single matrix operation based on the orthogonal projection image and a variance image generated from the orthogonal projection image (e.g., a variance image can be derived as described above at Step S1730).

Figure 22:
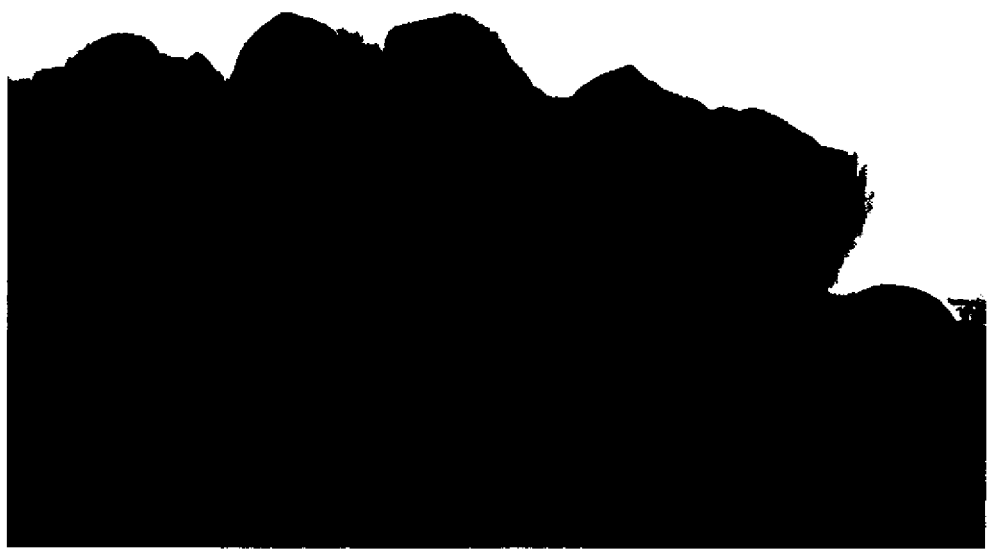
FIG. 22 illustrates an example binary mask image corresponding to the orthogonal projection image of FIG. 18.

Referring again to FIG. 17A, in Step S1714, a binary mask image, having the same dimensions as the orthogonal projection image, is formed based on the list of verified non-anatomic pixel coordinates provided in Step S1708. Each verified pixel coordinate on the binary mask image is assigned a pixel value of one. All other pixel coordinates on the binary mask image are assigned a pixel value of zero. For example, FIG. 22 illustrates an example binary mask image obtained in Step S1714 (and corresponding to the orthogonal projection image of FIG. 4).

Figure 23:
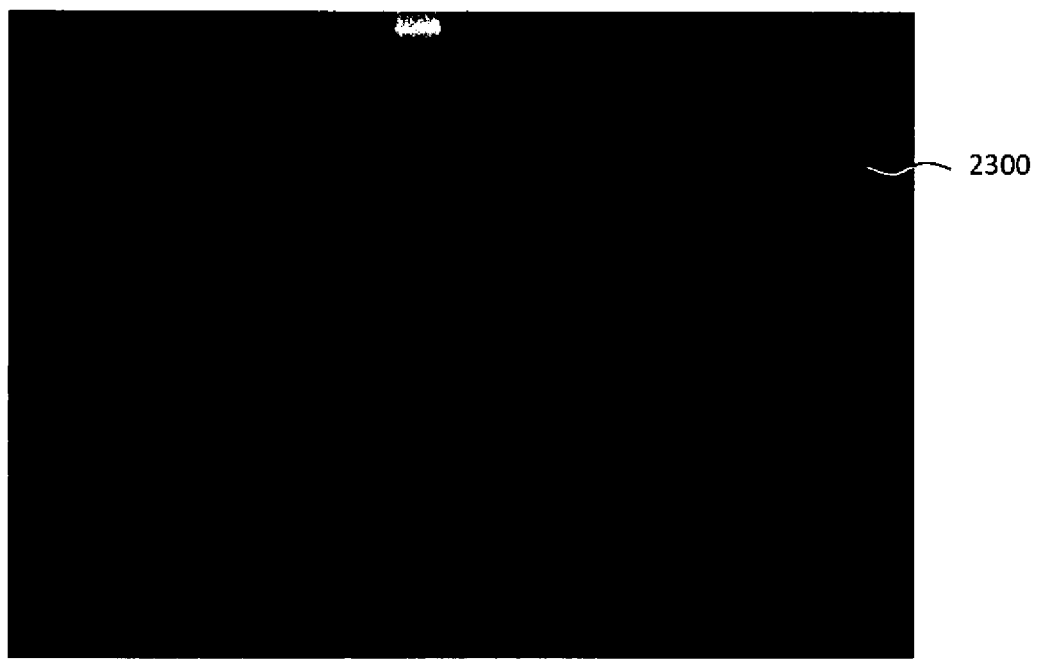
FIG. 23 illustrates a tomosynthesis image slice masked by the binary mask image of FIG. 8.

In Step S1716, each tomosynthesis image slice reconstructed in Step S1704 is masked by the binary mask image formed in Step S1714 to isolate the regions with no anatomic information. In an example embodiment herein, Step S1716 is performed by multiplying the binary mask image with each tomosynthesis image slice reconstructed in Step S1704 to provide a corresponding masked tomosynthesis image slice. For example, FIG. 23 illustrates a tomosynthesis image slice masked by the binary mask image of FIG. 22, resulting in an isolated nonanatomic region 2300.

Figure 24:
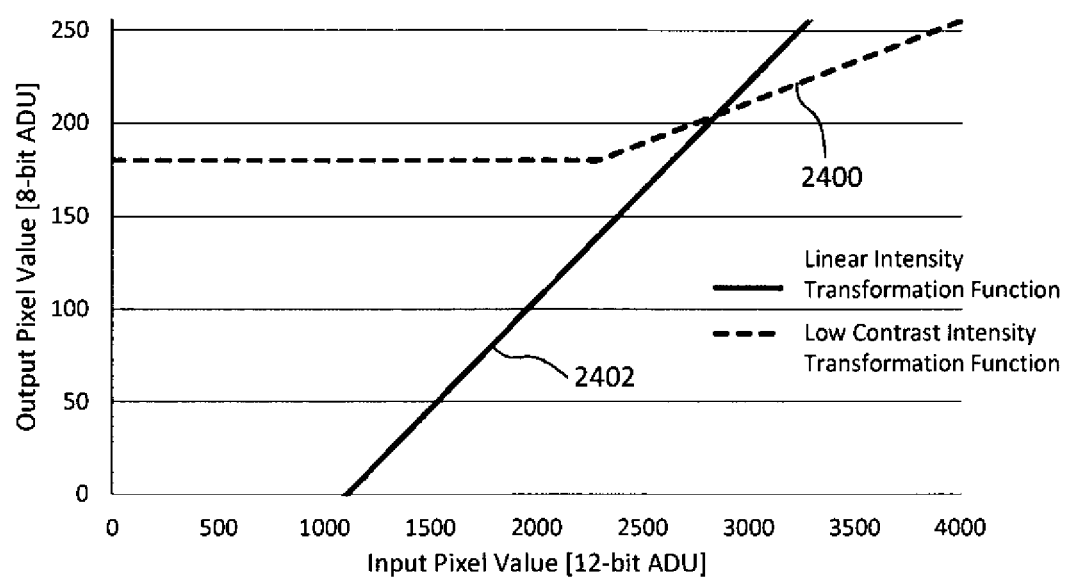
FIG. 24 illustrates a graph of an example intensity transformation function for compressing pixel values in isolated areas of a masked tomosynthesis image slice and a graph of an example intensity transformation function for linear mapping of pixel values in regions of the masked tomosynthesis image that contain anatomic information.

In Step S1718, the pixel values in the isolated nonanatomic regions of each masked tomosynthesis image slice obtained in Step S1716 are compressed to provide corresponding reduced-artifact tomosynthesis image slices. In an example embodiment herein, such compression is achieved by mapping the pixel values in the isolated regions through an intensity transformation function into different output pixel values. The intensity transformation function may be, in one example, configured to assign very low contrast to pixel values in isolated regions like, for example, the intensity transformation function illustrated by graph 2400 of FIG. 24.

Figure 25:
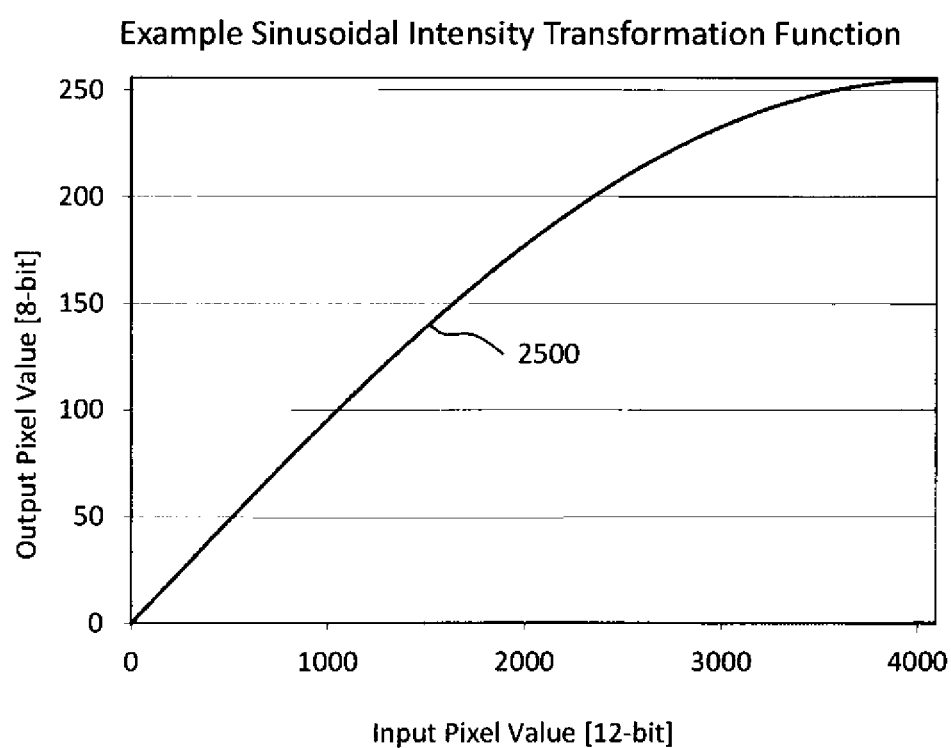
FIG. 25 illustrates a graph of an example intensity transformation function for sinusoidal mapping of pixel values in regions of the masked tomosynthesis image that contain anatomic information.

In addition to compressing pixel values in the isolated regions, Step S1718 may also include a further substep of applying an anatomic-region intensity transformation function to increase the contrast in regions containing anatomic information, the anatomic-region intensity transformation function being different from the intensity transformation function applied to isolated regions. Examples of anatomic-region intensity transformation functions include a linear intensity transformation function illustrated by graph 2402 of FIG. 24, a sinusoidal intensity transformation function illustrated by graph 2500 of FIG. 25, and a logarithmic intensity transform function (not shown). In the case that the foregoing substep is performed, Step S1718 outputs reduced-artifact tomosynthesis image slices where the pixel values in isolated regions have been compressed and pixel values in anatomic-regions have been contrast-enhanced.

Figure 26:
FIG. 26 illustrates an example reduced-artifact image slice.

In Step S1720, the computer system 106 displays one or more of the reduced-artifact image slices obtained in Step S1718 (i.e. the slices corresponding to respective tomosynthesis image slices reconstructed in Step S1704) on the display unit 108. In one example embodiment herein, the displaying can be performed so as to show all reduced-artifact image slices, or one or more selected reduced-artifact image slices, using display unit 108, and interactive controls are provided (e.g., via display unit 108 and/or input device 114) to enable a user to select between those two options, and to select one or more reduced-artifact image slices for display, and also to select one or more particular regions of interest in the reduced-artifact image slice(s) for display (whether in zoom or non-zoom, or reduced fashion). For example, FIG. 26 illustrates an example reduced-artifact image slice that may be displayed on the display unit 108.

In other example embodiments herein, reduced-artifact image slices obtained in Step S318 may also be utilized in further processing methods (not shown) with or without being displayed in Step S320. In one example embodiment herein, the reduced-artifact image slices can be utilized to generate clinical information from a tomosynthesis dataset according to the method described further herein below with reference to FIG. 2B. In another example embodiment herein, the reduced-artifact image slices can be utilized to interactively extract features for intuitive presentation to a clinician user, as described above. In another embodiment example, the reduced-artifact image slices can be utilized to render a 3D image of object 50 and/or sub-object(s) 52. In a further embodiment example herein, the reduced-artifact image slices can be utilized for measuring distances between points or structures of object 50 and/or sub-object(s) 52.

The process of FIG. 17A ends at Step S1722.

Three-Dimensional Image Rendering from Image Slices

Figure 27A:
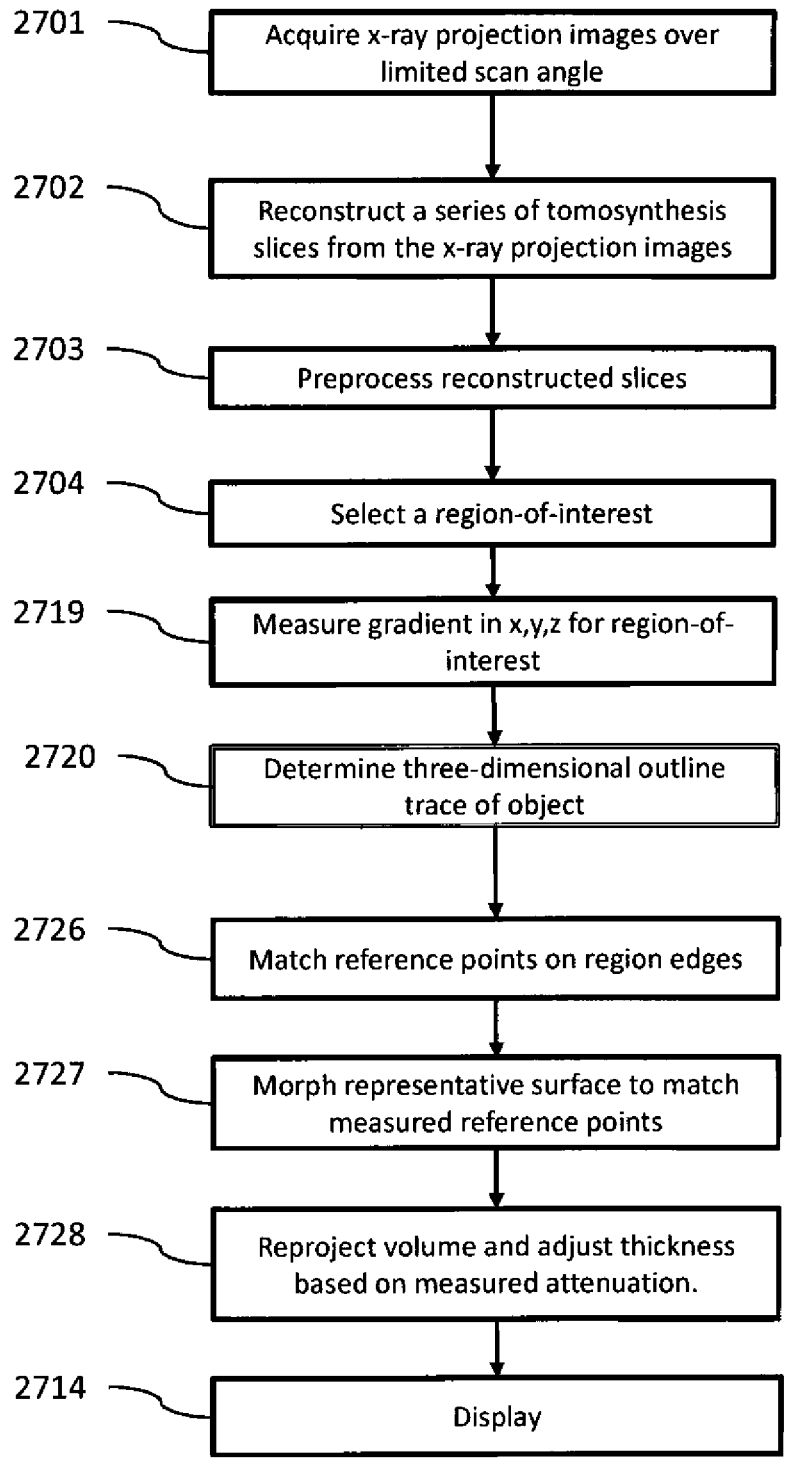
FIG. 27A is a flowchart illustrating a procedure for rendering a three-dimensional (3D) image from tomosynthesis slices according to an example embodiment herein.
Figure 27B:
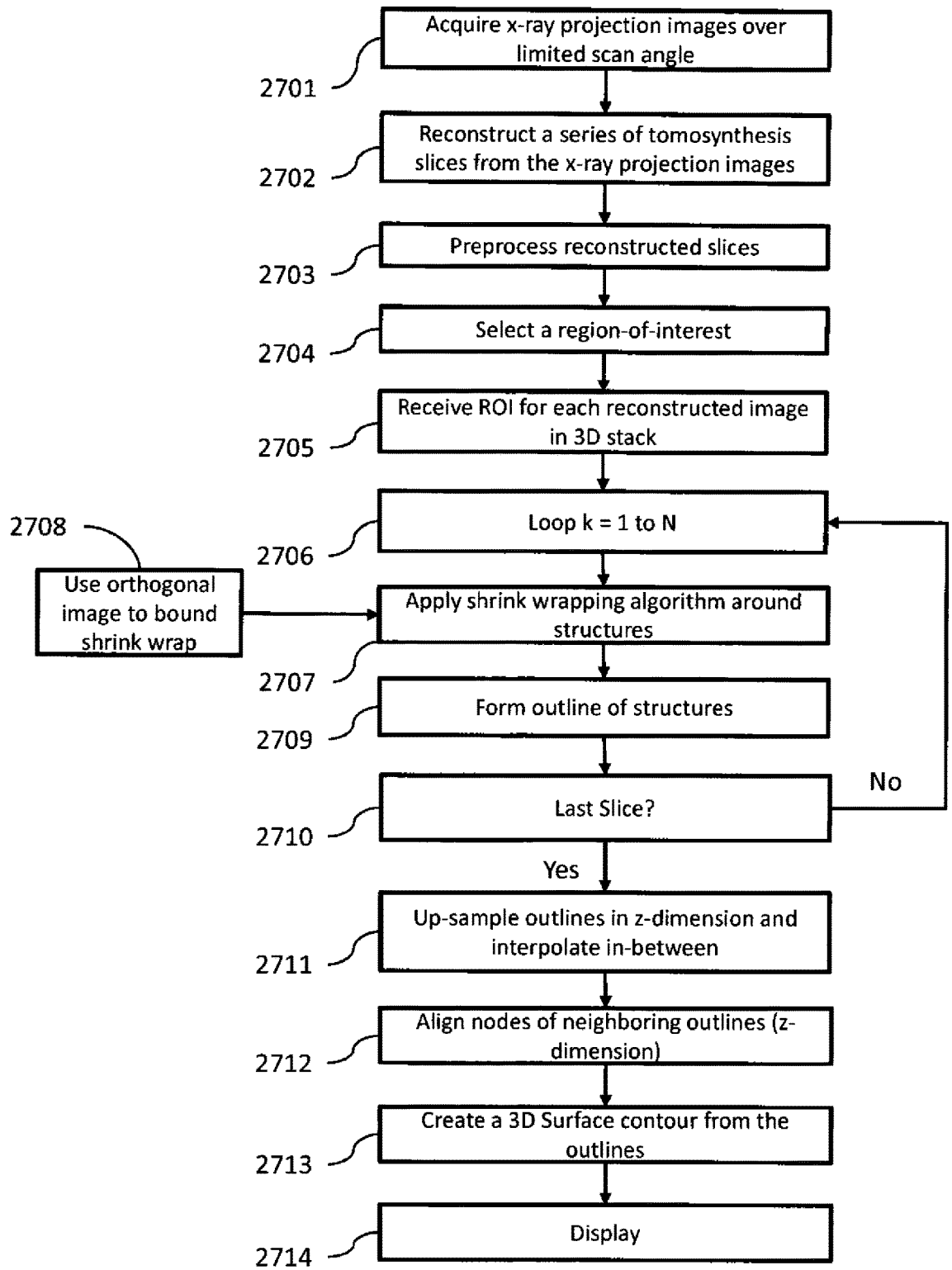
FIG. 27B is a flowchart illustrating another procedure for rendering a three-dimensional (3D) image from tomosynthesis slices according to an example embodiment herein.

FIGS. 27A and 27B are flow diagrams of processes for rendering a three-dimensional (3D) image from tomosynthesis slices according to example embodiments herein, or a sequence that can be used to enable such rendering.

Briefly, in FIGS. 27A and 27B, a series of two-dimensional x-ray projection images over a limited scan angle are obtained. Tomosynthesis slices are reconstructed from the x-ray projection images. A region-of-interest is defined in one or more of the tomosynthesis slices. An outline trace of one or more objects in the region-of-interest is created for each of the slices. Following this, a volume to be rendered may be generated by steps illustrated in either FIG. 27A or 27B, as discussed in more detail below.

As shown in FIGS. 27A and 27B, in step 2701, x-ray projection images are acquired over a limited scan angle. As discussed above, at each imaging position within the scan angle, x-ray source 104 emits x-rays 110 which pass through object 50 and are detected by the x-ray detector 102. For each imaging position, a projection image is obtained by the computer system 106 based on the intensity of the x-rays received by x-ray detector 102. Thus, the system 100 collects a plurality of projection images (also referred to herein as "projections") by positioning the x-ray source 104 at different angles, including, for example, the 0° position, and emitting x-rays 110 at each of those different angles through object 50 towards x-ray detector 102.

In step 2702 of FIGS. 27A and 27B, a series of tomosynthesis slices are reconstructed by computer system 106 from the plurality of projections images to form a tomosynthesis image stack. Each tomosynthesis slice is parallel to a plane in which the front surface of the x-ray detector 102 extends and at a particular depth in the z-axis direction corresponding to that tomosynthesis slice. Image reconstruction may be accomplished by several different reconstruction techniques including, for example, a shift-and-add method, filtered backprojection, matrix inversion tomosynthesis, generalized filtered backprojection, SIRT (simultaneous iterative reconstruction technique), or algebraic technique, among others.

In an exemplary embodiment, a shift-and-add method may be used. As discussed, the shift-and-add method takes into account the fact that objects at different heights (relative to the detector) will undergo varying degrees of parallax when exposed to x-rays at varying angles. To develop an image of objects at a specific height (i.e., a reconstructed tomosynthesis slice corresponding to a specific height), each projection image is shifted and added together with the other projection images at that height from different angles such that all objects in a plane at that height are in focus and objects outside of that plane are out of focus.

In step 2703 of FIGS. 27A and 27B, the reconstructed tomosynthesis slices obtained in step 2702 are preprocessed. The tomosynthesis slices may be preprocessed by undergoing one or more of edge enhancement, noise reduction filtering, and edge detection filtering. The preprocessing steps will be described more fully below with respect to FIG. 28.

Figure 29:
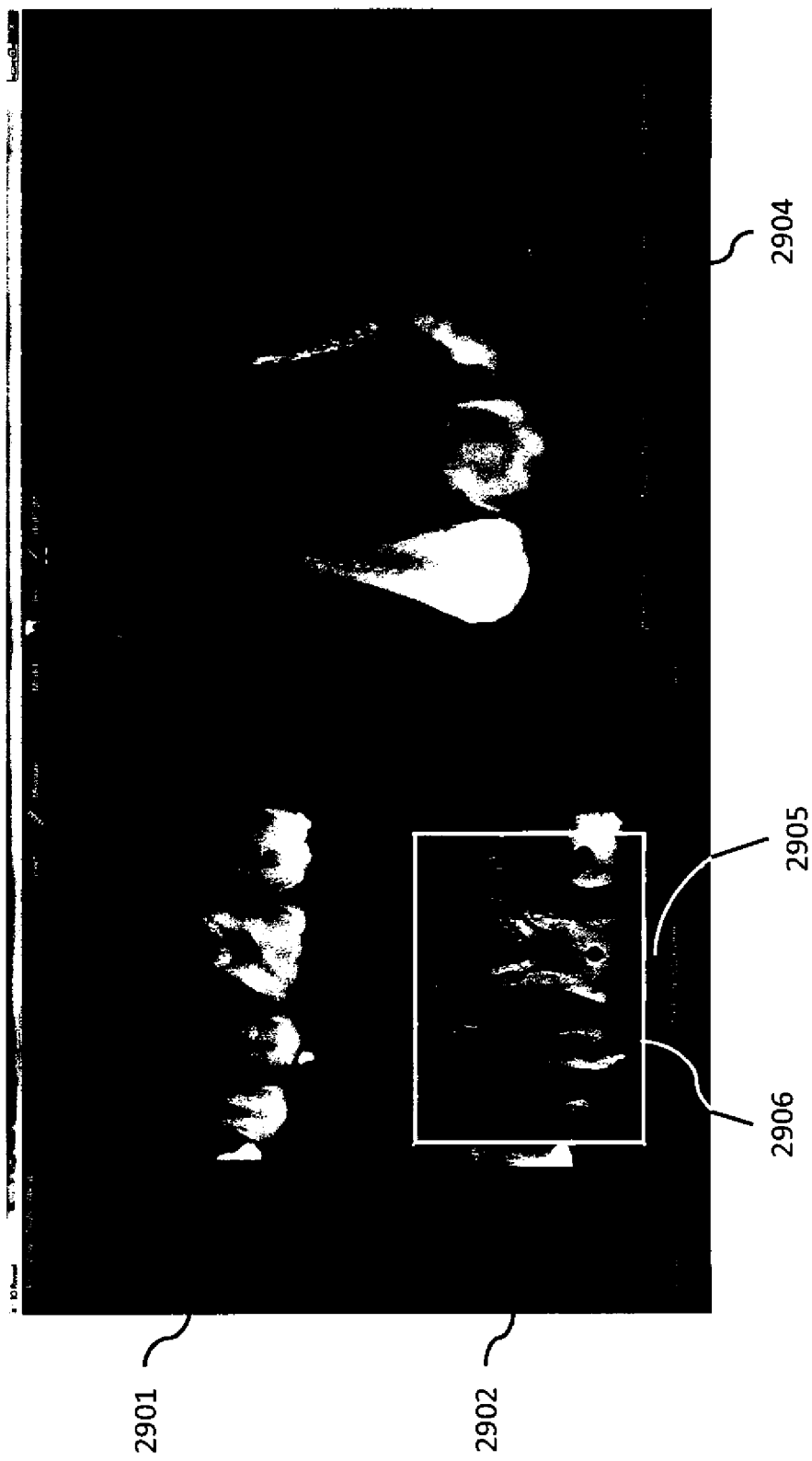
FIG. 29 is a view for illustrating display of a 3D image according to an example embodiment herein.

In step 2704 of FIGS. 27A and 27B, a region-of-interest in at least one of the slices that underwent preprocessing in step 2703 is selected for 3D rendering. In one example, an operator or user (such as a dentist) can operate an input unit (e.g., input unit 114) to define a region-of-interest in one or more of the tomosynthesis slices in the tomosynthesis image stack, while a display unit (e.g., display unit 108) displays the slice and the current region-of-interest. For example, an operator can drag a mouse to select a rectangle corresponding to the region-of-interest on a displayed 2-D tomosynthesis slice, as shown in FIG. 29 and described more fully below. Of course, the invention is not limited to this procedure for selecting a region-of-interest. In another example, the region could be traced on a display screen, selected by entering coordinates, or could be automatically selected based on predefined criteria.

As shown in FIG. 27A, after the region-of-interest is selected, the volume gradient for the region-of-interest, in directions parallel to the plane of the sensor, is measured in step 2719. From the measured volume gradient in step 2719, a three-dimensional outline trace of the object may be determined (step 2720) by a variety of techniques, including a gradient segmentation technique or a minimal path (geodesic) technique, as described below and illustrated in FIGS. 27C and 27D.

Figure 27C:
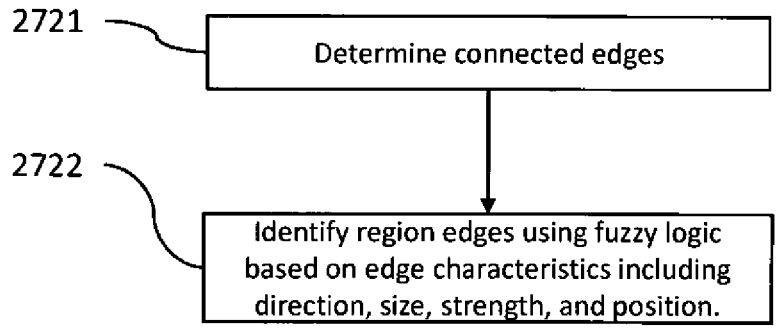
FIG. 27C is a flowchart illustrating one procedure for determining a three-dimensional outline trace of an object.
Figure 27D:
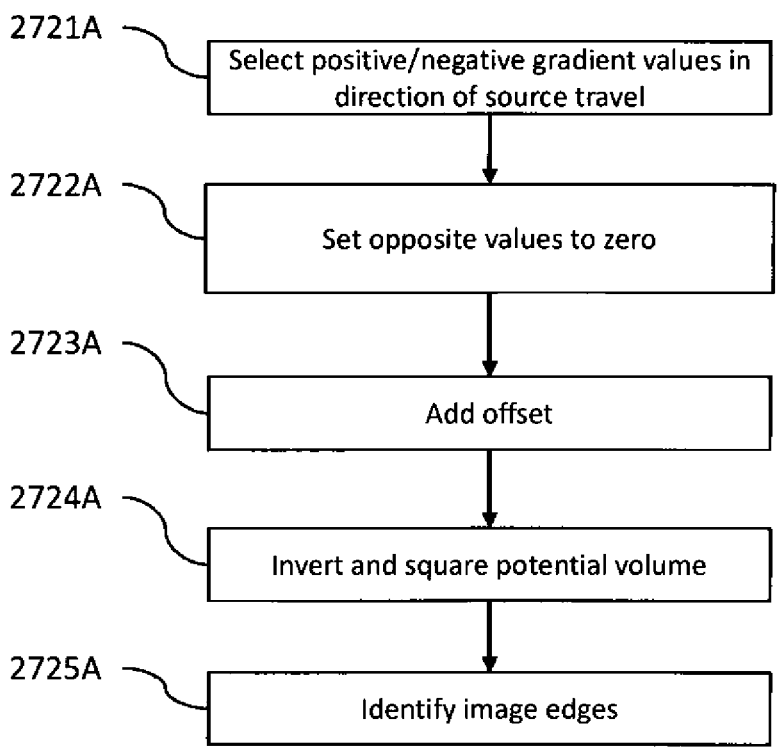
FIG. 27D is a flowchart illustrating another procedure for determining a three-dimensional outline trace of an object.

FIG. 27C illustrates exemplary steps in determining the outline trace using a gradient segmentation technique. In a gradient segmentation technique, the image volume is segmented (i.e., divided into sections) based on the magnitude of the gradient, and the output of the gradient segmentation is a binary image. The gradient is segmented to identify regions with a gradient magnitude (i.e., the absolute value of the gradient) above a certain threshold. Regions which are above the threshold are assigned one binary value (e.g., 1) and regions below the threshold are assigned another binary value (e.g., 0), resulting in a binary image. In step 2721, the measured volume gradient is processed as described above to produce a binary image which is then analyzed to determine connected edges, i.e., places where regions of different binary values are adjacent to one another. By determining the connected edges, separate objects may be identified and segmented from one another.

Once the objects are segmented, one or more object metrics such as the centroid, length, gradient direction, orientation, and root edge position relative to the region-of-interest may be calculated for each object. Based on one or more of these metrics, in step 2722, a fuzzy logic algorithm tailored to a specific root geometry for a tooth may be used to determine which edge of the connected edges of a segmented object is most likely to be a given part of the tooth. The specific root geometry may be selected from a library of root geometries stored in a computer. Fuzzy logic is a many-valued logic used to evaluate approximate reasoning. In this embodiment, fuzzy variables have values between zero (0) and one (1), inclusive. A value of zero (0) corresponds to false. A value of one (1) corresponds to true. Values between zero (0) and one (1) represent a probability of being true. For each relevant object metric, an acceptable range of values is identified and a measure of trueness is determined. For object metrics that are known to occupy a fixed range, for example, root edge position relative to the region-of-interest, the related fuzzy variable is zero outside of the range and a nonzero isosceles triangle within the range. More specifically, the probability increases linearly from one end of the range until a maximum probability is reached in the middle of the range, after which the probability linearly decreases until the end of the range is reached; thus forming an isosceles triangle with a maximum probability in the middle of the variable range. For object metrics that have a minimum value, the related fuzzy variable is zero below the minimum value and increases linearly until the object metric hits a defined saturation value. Each fuzzy variable corresponds to the probability that an object with a given metric value corresponds to a given portion of the tooth. The object metrics that are used are the maximum height, minimum height, the height, and the width of the object. To identify a given feature, the fuzzy variables are multiplied and the highest measure is selected. Alternately, a neural network may be used to identify the edges most likely to belong to the object.

In an alternative embodiment of embodiment 1, the outline trace is calculated using geodesic approach, that is by determining the quickest travel time between two points on a curved surface. First, a potential volume is estimated from the gradient volume calculated in step 2719. In an exemplary embodiment, the potential volume may be estimated by selecting either positive or negative gradient values in the direction of source travel (step 2721A). Each value in the gradient volume may be compared to a threshold value to identify regions that have relatively high gradient values, either positive or negative. Either positive or negative gradient values are selected, and the non-selected opposite gradient values are set to zero in step 2722A. To avoid unreal values when the thresholded gradient volume is inverted, an offset is added to the zero values in step S2723A. The amount of offset is chosen to reduce the ratio of the highest and lowest values in the estimated travel time to below a predetermined value (e.g., 10:1 ratio between highest and lowest values). The thresholded gradient volume is then inverted and squared (S2724A) to produce a potential volume.

Once the potential volume has been calculated, paths of minimal travel are determined to identify edges of objects (S2725A). One exemplary technique for calculating the paths of minimal travel is a fast march method, however, other techniques may also be used. In a fast march method, a series of calculations are performed to determine the quickest travel time from a starting point to one of the adjacent points (point A). Then, another series of calculations are performed to determine the quickest travel time from point A to one of the adjacent points (point B). This process repeats until the travel path reaches the desired point. Here, the quickest travel path coincides with an edge of the object and thus may be used to identify the edges (as opposed to the techniques discussed above for steps 2721 and 2722). This technique has the advantage of automatically identifying three-dimensional branches and being insensitive to small breaks in an edge. In a case where any spurious edges (i.e., edges that are not part of the tooth) are identified, those edges may be eliminated by reference to a nearby volume intensity, edge shape, or a known tooth topology. For example, a nearby volume intensity may be used to determine a difference in intensities between volumes on either side of the identified edge. If the edge corresponds to a tooth, then the difference in intensities should be above a certain threshold. If the difference is below that threshold, then the edge likely does not correspond to a tooth's edge and may be considered a spurious edge. In another example, if an identified edge bends abruptly then it is unlikely to be part of a real tooth. Furthermore, if the topology of the tooth is known then the identified edge may be compared to the known topology to determine whether the edge corresponds to the tooth.

Once the outline trace is determined using either of the techniques discussed above for embodiment 1, the outline trace is matched to corresponding points on a reference object model in step 2726. The reference model object is a surface model of a representative object such as, for example, a molar with an appropriate number of roots. The reference model object may be obtained either from available digital databases or may be generated either by means of a commercial three-dimensional optical scanner or by means of an x-ray tomography system. Although the outline trace determines the spatial position of the edges of the object, the depth of the object may not be determined by the outline trace, as it is not visible in the limited angle reconstruction. The position in a depth direction of the front and back faces of the object are estimated based on the ratio of the width of the reference object model to the thickness of the reference object model (aspect ratio). Positions of points on the front and back of the object surface are determined using the reference object model aspect ratio and the width of the outline trace, so as to generate an estimated object with a similar aspect ratio to that of the reference object. In step 2727, a morphing transformation based on the relationship between the model object and the estimated object may be applied to the model surface to generate the estimated surface. A morphing transformation is a method of mapping one volume onto another volume in a continuous fashion. In an exemplary embodiment, a locally bounded three-dimensional Hardy transform may be used as a morphing transformation. The three-dimensional Hardy transform may be estimated based on the corresponding points on the reference model object and the estimated object.

Next, in step 2728, the estimated surface created above is converted to a volume model and is reprojected into images matching the size and dimension of the original projections while assuming nominal attenuation values for dentin/enamel/pulp/air. In one embodiment, the estimated surface may be converted to a volume model first by assigning points adjacent to the estimated surface to the volume model and then filling the resulting hollow volume model. This may be accomplished using projection matrices calculated to match the projection geometry and using a calculation technique similar or identical to techniques used to estimate the backprojection matrices used for reconstruction in order to ensure the generation of compatible artifacts in the reprojected volume. Once the projection matrices are calculated, each projection matrix is then multiplied by the volume model in a matrix multiplication operation to obtain a projection of the volume model. The number of two-dimensional projections corresponds to the number of projection matrices. The two-dimensional projection images obtained by reprojecting the volume model obtained above (i.e., by simulating the passage of x-rays through the volume model) are subtracted from the measured projections and the resulting images are inspected to determine whether or not the estimated volume model is consistent with the data. Regions of the two-dimensional projections that contain accurately calculated objects are expected to be substantially uniform and non-negative. As such, regions within the two-dimensional projections that are substantially non-uniform or negative indicate inaccuracy in the volume model. Such regions may be determined by a thresholding operation. More specifically, the difference between the calculated projection and the recorded projection may be calculated, and for a given pixel if the difference exceeds a threshold value, that pixel is determined to be a point of inaccuracy. The model surface is then adjusted by adjusting the position of the extrapolated points (the points on the front and back of the object surface) in order to improve the consistency of the model with the measured data. For instance, if the remaining attenuation in the subtracted projections is less than zero, the volume model thickness decreases. This is accomplished by local adjustment of the aspect ratio of the reference model used to calculate the model front and back surfaces.

The technique described above, is also applied to the pulp chamber and root canal. In step 2714, the resulting images are displayed or otherwise presented.

Alternatively, in embodiment 2 (FIG. 27B), after a region-of-interest in at least one of the slices that underwent preprocessing in step 2703 is selected for 3D rendering, corresponding region-of-interests ("ROI") are received by computer system 106 for each of the other slices in the tomosynthesis stack. In one example embodiment herein, the stack of reconstructed slices can be searched to identify those that are in focus for a region-of-interest selected in a single slice. As noted above, the tomosynthesis stack is composed of a series of tomosynthesis slices that are two-dimensional images in respective planes that are parallel to the surface of the x-ray detector. In an exemplary embodiment, a user may scroll through the tomosynthesis stack. For example, a user can operate an input unit (e.g., input unit 114) to "scroll" or "page" through each, or selected ones, of the tomosynthesis slices in the tomosynthesis stack, while a display unit (e.g., display unit 108) displays those slices. To enable viewing of the slices, the displayed tomosynthesis stack can include a manual scroll bar and/or automation controls such as play, pause, stop, rewind or the like. As such, if the user is interested in focusing on a particular region-of-interest, or in determining the depth placement of particular features in an image, the user may interact with such functions to scroll through the tomosynthesis stack and visually evaluate each image or selected images (e.g., in order to designate a corresponding region-of-interest in each of the images).

In step 2706, a loop is started to loop through each slice of the stack of N slices, e.g., slice "1" to slice "N".

In step 2707, a "shrink-wrapping" algorithm is applied around the structure in the current slice. Generally, a shrink-wrapping algorithm approximates a surface by starting with a triangular mesh and deforming the mesh to transform it to the required surface. A "shrink-wrapping" algorithm is a variant of an active contour/snake algorithm. An active contour/snake algorithm operates by establishing a set of grid points that form a contour enveloping the object and progressively evolving the positions of the grid points subject to rules based on the image content. For example, for a "shrink-wrapping" style operation, the initial grid positions are placed outside of the object and these positions are evolved by rules assuming a repulsive "force" associated with the object and an attractive force between adjacent grid points. Thus, according to one example embodiment herein, the outline trace of the region-of-interest in each slice is created by applying a shrink-wrapping algorithm.

At the same time (or in another embodiment, not at the same time), in step 2708, an orthogonal input image (acquired in step 2701 as an x-ray projection image captured while x-ray source 104 is in the 0° scan angle position) is used to bound the shrink-wrapping algorithm being performed in step 2707. Thus, an orthogonal projection image is extracted from the plurality of projection images acquired in step 2701. Because, as described above, an orthogonal projection image is defined as the x-ray projection image captured while the x-ray source 104 is in the 0° scan angle position, no reconstruction is necessary or performed in step 2702 to extract the orthogonal projection image. Accordingly, in each slice, the shrink wrapping is bounded by an orthogonal image of the object(s) in the region-of-interest received in step 2705.

In step 2709, an outline of the imaged object (i.e., object 50) is formed in each slice of the stack, based on the shrink-wrapping algorithm bounded by the orthogonal image. Thus, for each slice, an outline of the structure in the region-of-interest is obtained. In addition, in step 2709, each contour corresponds to a single slice through the volume.

The surface of that volume is smoothed to eliminate non-uniformities by, for example, Gaussian filtering of the volume or by Laplace flow smoothing of a surface mesh.

In step 2710, there is a determination, based on integrated edge strength adjacent to the contour, of whether the last slice of the object within the image stack has been processed in the loop. More specifically, the gradient magnitude is integrated along the edge contour to estimate the overall edge strength. If not, the procedure returns to step 2706 to process a next slice in the stack. On the other hand, if the last slice has been processed, the procedure proceeds to step 2711.

In step 2711, the outlines formed in step 2709 are up-sampled in the z-dimension, and linear or trilinear interpolation is performed in-between the outlines to provide a higher-resolution contour. In particular, the collection of outlines, e.g., the set comprising each respective outline for each slice in the stack obtained for the region-of-interest in step 2709, represents a discretized contour of a 3D surface, and interpolating between the outlines will provide a highly-sampled and smooth 3D contour.

In step 2712, the nodes of neighboring outlines are aligned in the z-dimension. Any discontinuities in the volume are eliminated by aligning the final position of the grid points of the active contour of neighboring outlines. This may be done by linearly interpolating the grid positions between those estimated in adjacent slices.

In step 2713, the 3D surface contour is created from the aligned outlines. In this manner, the output of this technique is a 3D rendering of the dataset which is subsequently displayed as shown, for example, as view 2904 in FIG. 29 or as view 3004 in FIG. 30, which will be discussed more fully below.

In step 2714, the 3D surface contour obtained in step 2713 is displayed or otherwise presented. The 3D contour can, for example, be displayed on a display screen in a separate window, as shown by view 2904 in FIG. 29 or view 3004 in FIG. 30. The display may be provided with lighting, rotational, camera, coloring, viewing controls for the 3D contour, and/or the like. Thus, for example, the contour can be rotated freely and a full 3D visualization, including side and back views, of the structures can be provided. In addition, measurement capabilities can be incorporated to provide true 3D measurements between multiple structures/features, as described more fully below with respect to FIG. 31A to FIG. 31C.

Figure 28:
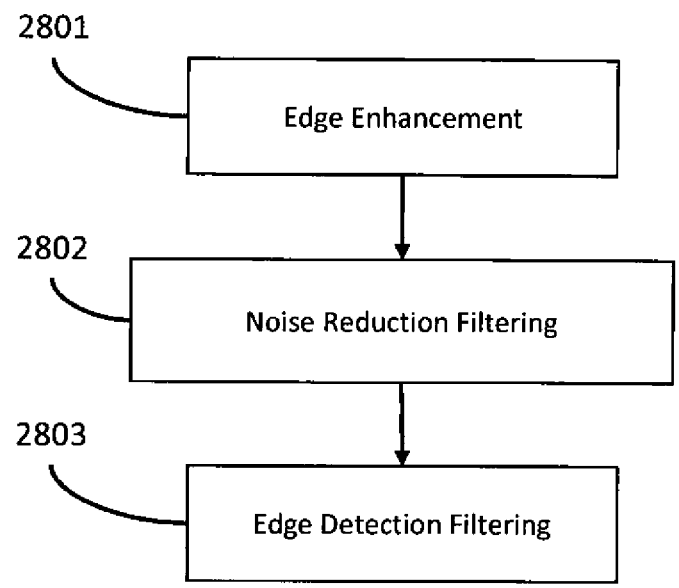
FIG. 28 is a flowchart illustrating a procedure for pre-processing tomosynthesis slices according to an example embodiment herein.

FIG. 28 is a flowchart (titled "Pre-Processing") illustrating a procedure for pre-processing reconstructed tomosynthesis slices according to an example embodiment herein, and represents in further detail the manner in which step 2703 in FIGS. 27A and 27B is performed. In step 2801, edge enhancement is performed for each slice reconstructed in step 2702, for example, by use of Fourier filter which ramps linearly from 100% to 30% ranging from maximum spatial frequency to zero spatial frequency. Thus, in one example herein, a filter is used to increase the edge contrast of each structure in the slice in order to improve its sharpness.

In step 2802, noise reduction filtering is performed on each of the slices, using, for example, a low-pass filter. Similarly, for example, each volume slice may be convolved with a Gaussian kernel with a radius between 0.25 and 1 pixel in order to reduce noise. Accordingly, noise and other artifacts can be removed or reduced from the slices.

In step 2803, edge detection filtering is performed on each slice, to more clearly define the edges of each structure (e.g., object 50, such as one or more teeth). Typically, edge detection filtering may be performed in many manners. One technique to estimate the image gradient in a given direction is by convolution with a kernel estimated from the derivative of a Gaussian in the given direction. As a result of the pre-processing described with respect to FIG. 28, the visibility of the slices is enhanced.

FIG. 29 is a view for illustrating a display and user interface according to an example embodiment herein.

In particular, as shown in FIG. 29, multiple windows can be presented (via, e.g., display unit 108) to allow for convenient control and analysis by a viewer.

In the example shown in FIG. 29, image 2901 is an image for defining a region-of-interest 2906, as described above with respect to step 2704 of FIGS. 27A and 27B. An example of a 3D rendering (of the region-of-interest 2906) is shown in image 2904, and can be obtained according to the procedure described in FIG. 27A.

As shown in FIG. 29, an image 2901 is an orthogonal projection image obtained in step 2701, and corresponds to an image captured while the x-ray source 104 is in the 0° position shown in FIG. 1A above. The orthogonal image 2901 can be displayed alongside an image 2902 of a current slice (as shown), in order to provide a reference view for comparison. Thus, in one embodiment, the orthogonal projection image 2901 is displayed as a default image regardless of whether the user has selected another slice, and is displayed separately from any currently selected slice, and, so as to provide a visual default reference.

Image 2902 depicts a currently selected tomosynthesis slice in the stack. Specifically, image 2902 is a currently selected image from the tomosynthesis stack (which was reconstructed in step 2702 from the projection images obtained in step 2701) that has undergone preprocessing in step 2703. A user may change the displayed tomosynthesis slice 2902 by navigating to different slices in the stack. In particular, using an input unit (e.g., input unit 114), the user can view images at different planes in the stack. For example, in the embodiment shown in FIG. 29, the user can click or otherwise designate arrow indicators on scroll bar 2905 to toggle through each slice to navigate to a desired slice. Scroll bar 2905 may also include additional visual indicators of the position of the currently displayed slice in the stack. For example, in the embodiment shown in FIG. 29, scroll bar 2905 displays the slice position relative to the detector plane for the corresponding slice image 2902. The scroll bar may, for example, indicate whether the slice is towards a buccal or lingual position.

Figure 30:
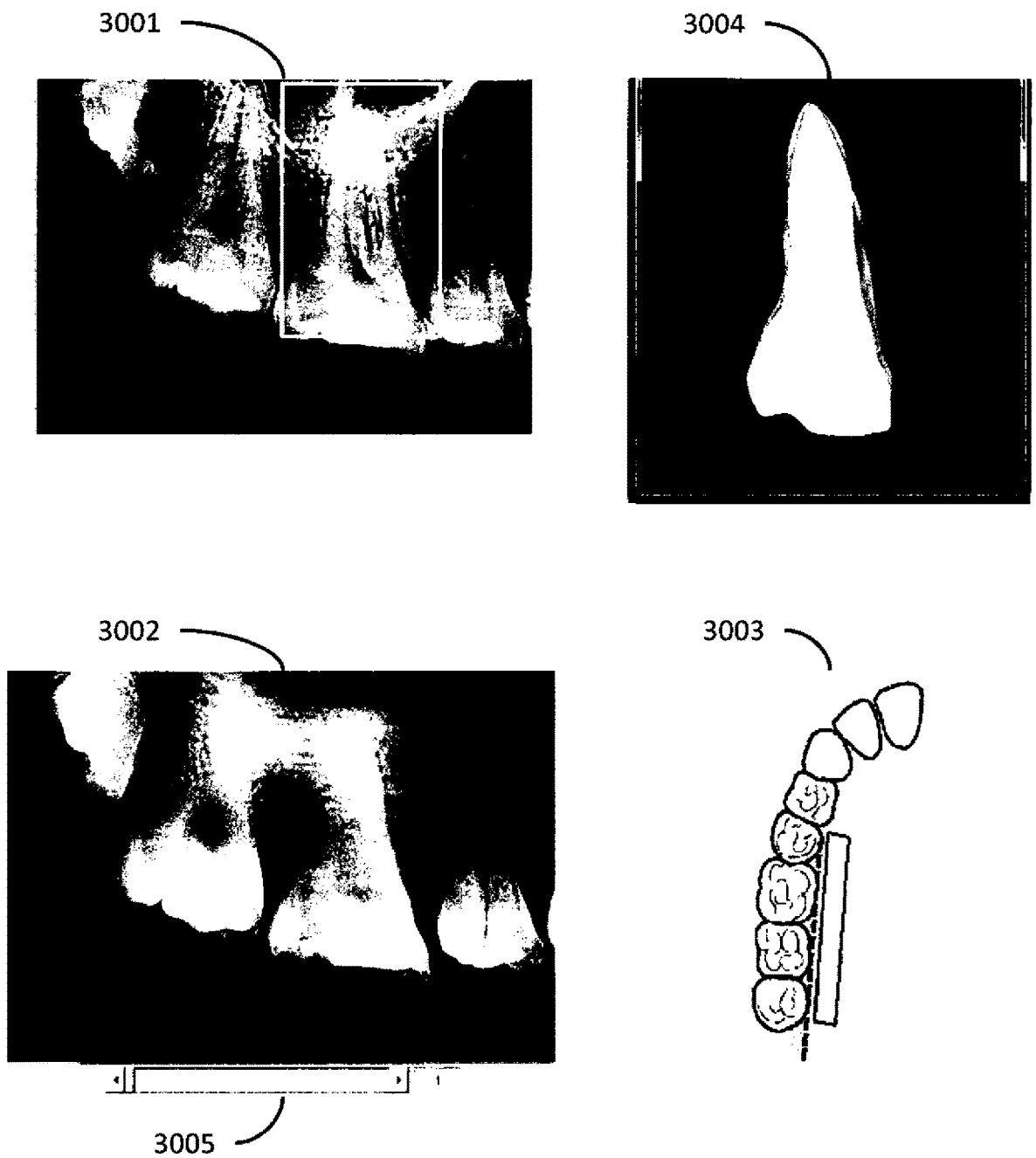
FIG. 30 is a view for illustrating a 3D surface rendering based on a region-of-interest according to an example embodiment herein.

FIG. 30 is a view for illustrating another example display and user interface according to an example embodiment herein. In FIG. 30, the orientation and function of images correspond generally to those depicted in FIG. 6, but after a rotation of the 3D rendering (see 3004). Thus, in FIG. 30, image 3001 corresponds to an image of the slice with the region-of-interest remaining highlighted, image 3002 depicts the current slice, image 3003 depicts the current position of the sensor, and scroll bar 3005 is for scrolling through the slices. Image 3004 depicts the 3D rendering of the tooth and may be rotated (in any direction) to allow additional 3D viewing of the structure of the object of interest (e.g. a root). The example of a 3D rendering shown in image 3004 can be obtained according to the procedure described in FIG. 27B. In one example embodiment, display in step 2714 is updated according to user input. In particular, the user can manipulate the 3D image in view 3004 to orient the displayed object in the manner desired, by, for example, accessing viewing controls or predefined input device actions (e.g., via input unit 114 shown in FIG. 1A), to thereby view different aspects of the tooth (or other structure). Accordingly, the 3D image is displayed in step 2714 (e.g., via display unit 108 shown in FIG. 1A), and visual aspects of the 3D image can be manipulated to provide a different display.

Figure 31A:
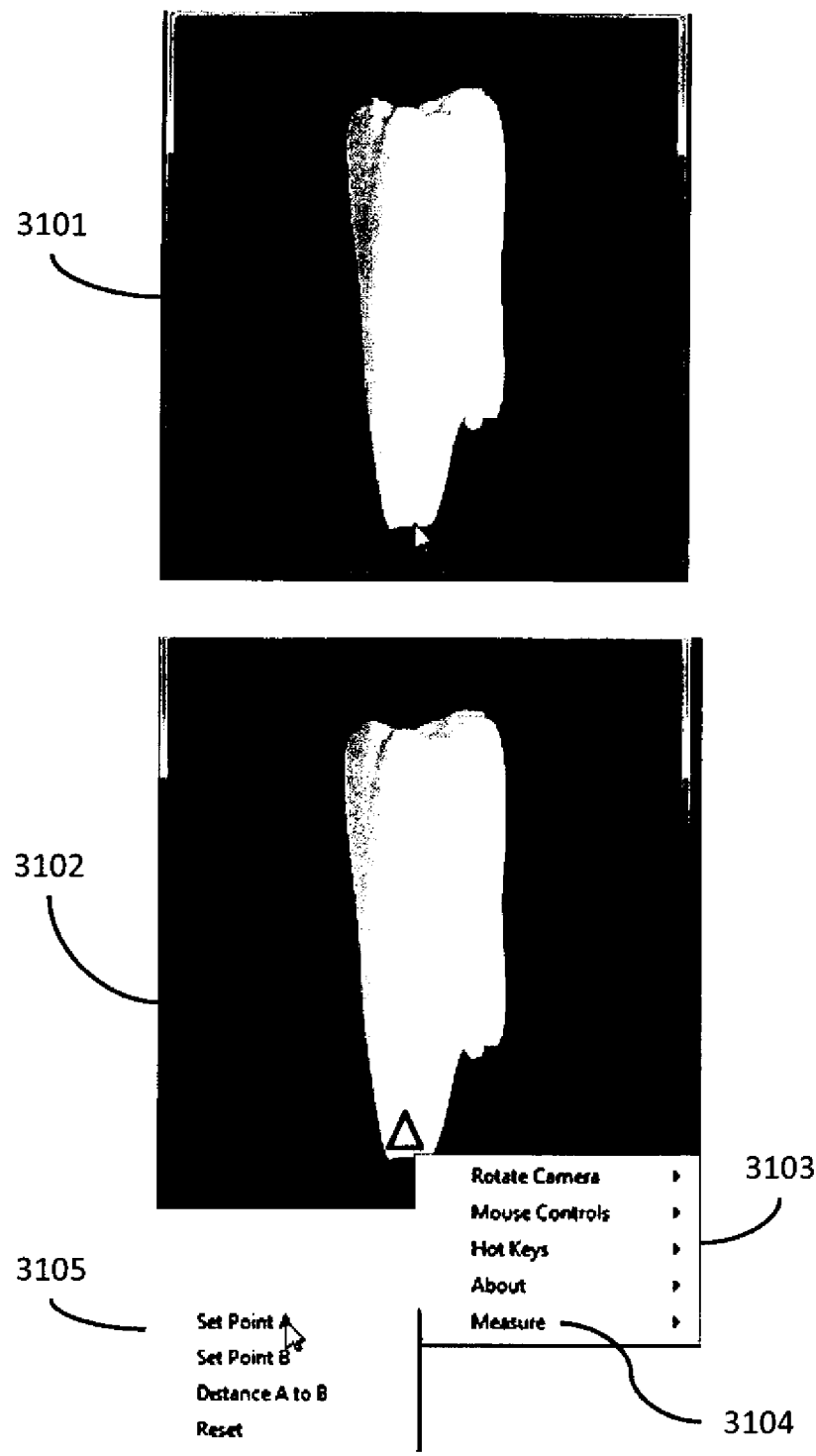

FIGS. 31A to 31C are views for illustrating measurement of distances in a 3D image according to example embodiments herein.

Specifically, FIGS. 31A to 31C show different states of a 3D rendering image of a tooth depicted on a display unit (e.g., via display unit 108 shown in FIG. 1A), as a user sets measurement points and enables measurement of distances on the 3D rendering.

Specifically, FIG. 31A is an illustration representing examples of how a measurement process between two points on a 3D rendering of a tooth can be started. As shown in image 3101, a point on the 3D rendering of a tooth (e.g., using a mouse or other interface device) is navigated to.

In image 3102, with the desired first measure point "A" having been navigated to, a user manipulates an input device (e.g., via input unit 114 shown in FIG. 1A) to display a user interface (e.g., menu 3103), for example by right-clicking on a mouse. Menu 3103 enables a user to, for example, rotate or manipulate the 3D rendering, set mouse controls, set hot keys, obtain further information ("about"), and measure between points on the 3D rendering. In the example shown in image 3102, the user has selected the "measure" option 3104, which brings up a further user interface 3105 enabling the user to set a measure point A, a measure point B, to request the distance between A and B, and to reset. As shown, the user selects "Set Point A" to set a first measurement point (indicated by the triangle in FIG. 31A).

Turning to FIG. 31B, the user follows a similar procedure to set the measure point B. As can be seen from image 3106, however, the 3D rendering has been rotated from the views shown in FIG. 31A. Thus, image 3106 represents an example of a case where the user has rotated and manipulated the view for better access to measure points desired for selection. Once measure point B is selected (represented by the cross in FIG. 31B), image 3107 is provided with a line 3108 connecting the two points A and B.

In FIG. 31C, in image 3109, the user selects to calculate the distance between the points A and B that were selected as shown in FIG. 31A and FIG. 31B. This can be accomplished with, for example, the same drop-down menu used to set the measurement points A and B. As a result, the distance between points A and B is calculated. For example, assuming the coordinates of point A in the 3D space are $(x_1, y_1, z_1)$ and the coordinates of point B in the 3D space are $(x_2, y_2, z_2)$, the distance can be calculated as $d=\sqrt{(x_2-x_1)^2+(y_2-y_1)^2+(z_2-z_1)^2}$.

In image 3110, a window 3111 appears, displaying the calculated distance between points A and B, along with coordinates of the points A and B in the 3D space. Accordingly, the user is provided with a convenient tool to easily view and measure distances between structures (or distances within structures) in the 3D rendering, whether the structures are in the same image slice or different image slices.

As discussed, for x-ray images to have value and utility in clinical diagnosis and treatment, they should have high image fidelity and quality (as measured by resolution, brightness, contrast, signal-to-noise ratio, and the like, although these example metrics are not limiting) so that anatomies of interest can be clearly identified, analyzed (e.g., analysis of shape, composition, disease progression, etc.), and distinguished from other surrounding anatomies. The processes described in FIGS. 27A and 27B can be used to improve image fidelity and quality by reducing image artifacts and optimizing image contrast.

Measuring Three-Dimensional Distances in a Stack of Images

Figure 32:
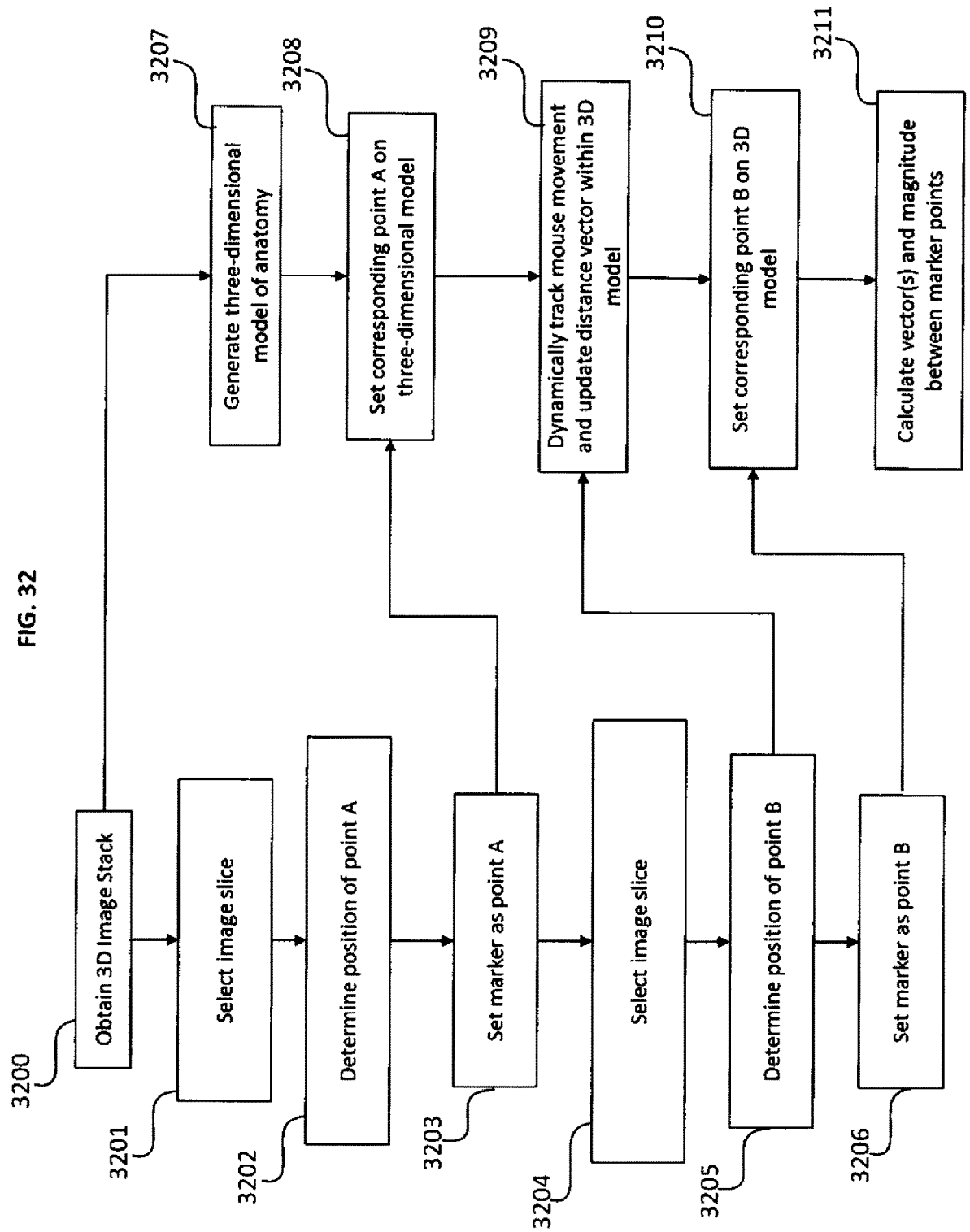
FIG. 32 is a flow diagram for explaining measurement of distances in tomosynthesis images according to an example embodiment herein.

In accordance with an example aspect described herein, a method, system, apparatus, and computer program product are provided for measurement between structures in tomosynthesis images, and more particularly, for measuring 3D distances in a stack of tomosynthesis images will now be further described in conjunction with FIG. 32, which shows a flow diagram of an exemplary process for measuring distances in a three-dimensional tomosynthesis images according to one example embodiment herein.

Briefly, by virtue of the procedure of FIG. 32 and as will be described below, distances between points in a three-dimensional space corresponding to a tomosynthesis dataset may be obtained. A stack of tomosynthesis images (slices) is obtained. Specifically, the stack of tomosynthesis images is reconstructed from x-ray projection images taken over a scan angle. The tomosynthesis slices are a series of images which are parallel to a plane defined by the surface of the x-ray detector 102. The tomosynthesis stack is comprised of the tomosynthesis slices. Each tomosynthesis slice is stacked on top of or below another slice in a direction orthogonal to the plane of the x-ray detector. Thus, the plurality of tomosynthesis slices comprising the tomosynthesis stack correspond to an image volume (i.e., a certain volume of space in three-dimensions). If the plane of the x-ray detector is defined as the x-y plane and a direction orthogonal to the plane of the x-ray detector is defined as the z-axis, then a point $P_i$ within the image volume may be identified by it three-dimensional Cartesian coordinates $(x_i, y_i, z_i)$.

In the exemplary embodiment shown in FIG. 32, a distance from one point in the image volume to another point in the image volume may be determined. Briefly, a first point on a first tomosynthesis slice and a second point on a second tomosynthesis slice (or the first tomosynthesis slice) are selected. The computer system 106 may determine the x-y coordinates of the first and second points from the pixel arrays corresponding to the respective tomosynthesis slices. As noted above, each tomosynthesis slice occupies a certain position within the tomosynthesis stack. In other words each tomosynthesis slice lies a certain distance from the surface of the x-ray detector along the z-axis. Thus, all the points within a tomosynthesis slice have the same value for a z-coordinate. Thus, by knowing the system geometry and the position of the tomosynthesis slice within the tomosynthesis stack, the z-coordinate may be determined.

As one of ordinary skill will appreciate, the x-y coordinates of a given point may correspond to a particular anatomical plane. For example, a tomosynthesis slice may lie in a plane substantially parallel to the occlusal surface. The relationship between the tomosynthesis slices and certain anatomical features will be further explained below in reference to FIGS. 39A-41B.

In step 3200, the computer system 106 generates a tomosynthesis stack comprising a plurality of tomosynthesis slices from a plurality of projections images, as discussed above and with reference to FIGS. 1A-1D.

In step 3201, a user selects a tomosynthesis slice from the tomosynthesis stack. In an exemplary embodiment, the user may operate an input unit (e.g., input unit 114) to "scroll" or "page" through each, or selected ones, of the slices in the tomosynthesis stack, while a display unit (e.g., display unit 108) displays those slices. To select a particular slice, the user may stop scrolling or otherwise moving through the stack. An example embodiment illustrating this process is shown in FIGS. 33A-33D, which will be discussed more fully below.

Once the user has selected a particular slice, the user may, in step 3202, use the input unit 114 to select a point on the displayed slice to place a marker, which then serves a first measurement point. In an exemplary embodiment, this marker indicates a particular anatomical location or plane. The user may also change the location of the marker after it is initially set. For example, the user may manipulate the input unit 114 (e.g., a mouse) to move the marker over the displayed slice, and then use another input (e.g., clicking a button on the mouse) to designate the placement of the marker once the marker is in a desired location (step 3203).

Once the marker is placed at the desired location, the location of the marker is set as a point A, and the x-y coordinates of point A are saved in memory as point A (or using some other designation). The marker for point A may be displayed differently from a marker in another later selected slice for a point B, in order to help the viewer quickly observe that the points are in different slices and thus at different positions along the z-axis. For example, a marker for point A may be displayed in a different color than a marker for point B. An example embodiment illustrating this process is shown in FIGS. 34A-37D, which will be discussed more fully below.

Turning now to step 3207, before or concurrently with the actions in steps 3201 to 3203, a three-dimensional volumetric image ("volumetric image") of the image volume is created. The volumetric image may provide for better visualization and representation of an imaged object. For example, if the imaged object is a tooth, the volumetric image may provide a user with a perspective view of the tooth which aids in determining a relative location of the slices. The volumetric image of the image volume may be generated from the tomosynthesis stack. As discussed above, the tomosynthesis stack includes a plurality of tomosynthesis slices at a plurality of depths, and the volumetric image of the image volume may be generated from the tomosynthesis slices. In another example embodiment herein, the volumetric image may represent the three-dimensional structure of the imaged anatomy or it may represent a model volume that approximates the shape of the anatomy.

As discussed above, each tomosynthesis slice in the tomosynthesis stack corresponds to a two-dimensional image in an x-y plane (parallel to the plane of the x-ray detector). The z-axis is orthogonal to the surface of the x-ray detector 102 and thus a coordinate value for the z-axis represents a distance from the surface of the x-ray detector 102. Thus, as discussed above, scrolling through the tomosynthesis slices, corresponds to traveling through the image volume in a direction towards or away from the surface of the x-ray detector.

If the system geometry is known (or deduced from one or more objects within the plurality of projection images such as alignment markers) the computer system 106 may determine a distance between two tomosynthesis slices. For example, if a tomosynthesis slice lies just beyond the surface of a tooth (e.g., proximate to but not including, for example, a buccal surface), the computer system 106 may identify that slice and produce a depth measurement based on the separation between that slice and another slice. For example, if a slice proximate to but not including a buccal surface of a tooth is labelled $S_i$, and another slice located beneath, and within the tooth structure is labelled $S_j$, then the depth of slice $S_j$ relative to the buccal surface may be calculated based on the difference between i and j and the known distance between slices.

In step 3208, the marker placed at point A is transferred to a corresponding location on the volumetric image. The coordinates of point A may also be set as a geometrical base (i.e., an origin) of a measurement vector from point A to point B (discussed below), in the image volume.

To determine point B (step 3205), a user may scroll through the tomosynthesis stack to a desired tomosynthesis slice (step 3204) and then place a second marker (step 3206) at a desired location (point B) on the displayed tomosynthesis slice. The x-y coordinates of point B are saved in memory under that designation (or some other designation). As discussed above, a user may operate the input unit (e.g., input unit 114) to scroll or page through each of the slices in the tomosynthesis stack, and the display unit (e.g., display unit 108) displays each slice. As discussed, a user may (at least temporarily) pause or stop scrolling, toggling, or otherwise moving through the stack when the user reaches the desired slice. Typically, the second marker would be placed on a different tomosynthesis slice ($S_2$) from the tomosynthesis slice containing the first marker. If the second marker were placed on the same slice as the first marker, then the measurement would correspond to a linear distance between the first and second marker within a plane defined by the tomosynthesis slice. In other words, a two-dimensional measurement as opposed to a three-dimensional measurement. Nevertheless, it should be understood that the second marker, and thus the second measurement point, could be in the same tomosynthesis slice as that of point A.

The second marker may be visually distinguishable from the first marker. For example, the second marker may be a different color, shape, or size from the first marker. Moreover, the first marker may remain visible on the displayed tomosynthesis slice, even if the displayed tomosynthesis slice is different from the tomosynthesis slice in which the first marker is placed. The user may therefore see the x-y location of the first marker as the user scrolls through the tomosynthesis stack.

As the user operates the input unit 114 to place the marker for the second measurement point, the computer system 106 calculates the measurement vector from point A to point B, which respectively correspond to the first and second measurement points in the image volume (step 3209). If the user moves the second measurement point (or the first measurement point) to a different location using the input unit 114, the computer system 106 may dynamically update a the measurement vector as the measurement point is moved. Thus, in one embodiment, the computer system 106 may dynamically update the measurement vector while either the first or second measurement point is moved or changed, in addition to calculating the measurement vector when the two measurement points are initially set.

In a similar manner to step 3208, a point corresponding to point B is placed on the volumetric image of the image volume generated in step 3207 (step 3210). As discussed, the volumetric image provides the user with a three dimensional view of the image volume. Thus, by placing points corresponding to points A and B, respectively, on the volumetric image, the user may appreciate the three dimensional relationship between points A and B, which may be not be obvious from the two-dimensional tomosynthesis slices.

In step 3211, the computer system 106 calculates the vector $V_{AB}$ between points A and B. The vector includes both a magnitude and direction. For example, assuming the coordinates of point A in the 3D space are ($x_1, y_1, z_1$) and the coordinates of point B in the 3D space are $(x_2, y_2, z_2)$, the vector magnitude may be calculated according to $d=\sqrt{\{\text{square root over }((x_2-x_1)^2+(y_2-y_1)^2+(z_2-z_1)^2)\}}$. The computer system 106 may also calculate the x, y, and z vector components. These vector components may also correspond to the mesiodistal, buccolingual and coronoapical axes as discussed below.

Of course, other methods or formulas for calculating the magnitude of the vector can be used in step 3211. The magnitude of the vector can then be displayed on the display unit 108 in a variety of manners, as discussed more fully below. The features described above and illustrated in FIG. 32 will now be explained in further detail below with reference to FIGS. 33A-41B.

FIG. 33A is a two-dimensional projection image 3301 recorded by the x-ray detector 102 at the 0° position, as shown in FIG. 1A above. As discussed above, the plurality of projection images are used by computer system 106 to create a tomosynthesis stack comprising a plurality of tomosynthesis slices. FIG. 33B illustrates the spatial relationship between a tomosynthesis slice 3302 (shown in FIG. 33C) located a distance $d_i$ from the x-ray detector 102 in the z-axis direction. The tomosynthesis slice is number $S_i$ of $S_j$ comprising the tomosynthesis stack, as indicated by slice number display 3304 adjacent to scroll-bar 3306. FIG. 33D is an illustration showing the location of the tomosynthesis slice 3302 within the image volume.

In an exemplary embodiment, one or more of the images shown in FIGS. 33A-33D may be displayed at the same time on a display unit (e.g., display unit 108), so that a user can conveniently view information relating to a current slice and its relative position.

As discussed above, a user may use an input unit 114 to change the displayed tomosynthesis slice. For example, the user may interact with scroll-bar 3306 to change the displayed tomosynthesis slice. The user may drag the scroll-bar icon positioned on scroll bar 3306 to toggle through each slice to navigate to a desired slice in the z-axis direction. Scroll bar 3306 may also include additional visual indicators of the position of the current slice in the stack. For example, a text box may be displayed concurrently with the tomosynthesis slice that shows a distance $(d_i)$ from the tomosynthesis slice to the surface of the x-ray detector 102. As the user scrolls through the tomosynthesis stack, the value $d_i$ may be concurrently updated to correspond to the displayed tomosynthesis image.

As discussed above in regard to steps 3202 and 3203, once a user selects a desired tomosynthesis slice, a marker 3402 may be placed at a desired location, as illustrated in FIG. 34. In one embodiment, the user may place the marker 3402 by a double-tap operation of a mouse, touchscreen, or similar device. In another embodiment, the user may use the input 114 to bring up a menu graphical user interface menu ("menu") that may include a command "Set As Point A," along with other commands (e.g., "Set As Point B", "Clear Point A", "Clear Point B", "Clear All Points", "Rotate Measurement Axis", "Reset 3D View"). Some of the commands may be "greyed out", i.e., unavailable, during the process illustrated in FIG. 32. By selecting the command "Set As Point A", the desired location may be set as point A, and a marker 3402 may be placed at that location.

Figure 35B:
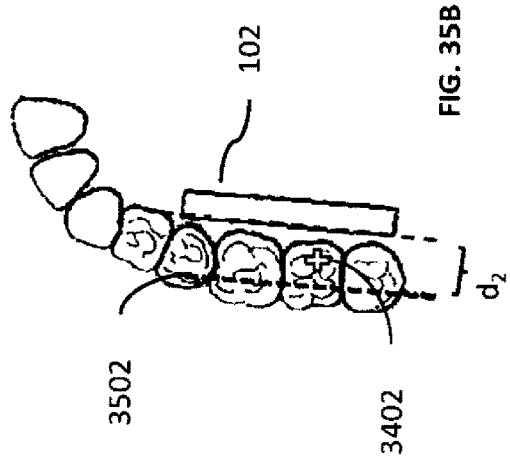
FIGS. 35A-D are illustrations of a two-dimensional x-ray projection image, another tomosynthesis slice, a distance between the tomosynthesis slice and the x-ray detector, and the other tomosynthesis slice within the image volume according to an example embodiment herein.
Figure 35D:
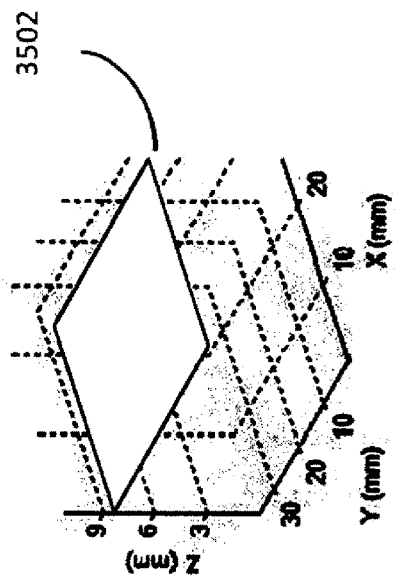
Figure 35A:
Figure 35C:

As discussed above in reference to steps 3204-3206, once point A is selected, the user may select another point (point B) on the same tomosynthesis slice or a different tomosynthesis slice. As discussed above, the user may use input unit 114 to navigate to the desired tomosynthesis slice (if applicable). FIG. 35C is an illustration of a second tomosynthesis slice 3502 ($S_2$) located a distance $d_2$ from the x-ray detector 102 (as illustrated in FIGS. 6B and 6D) which the user has navigated to. As shown in FIG. 35C, the slice number display 3304 now reads $S_2$. FIG. 35A is the x-ray projection image recorded at the 0° position and is identical to FIG. 33A, discussed above. As discussed above, one or more of these images may be displayed on display unit 108, either concurrently or individually. While FIGS. 35B-35D illustrate a tomosynthesis slice 3502 which is further away from the surface of the x-ray detector 102 in the z-axis direction, the second tomosynthesis slice could also be located closer to the x-ray detector 102. As discussed, a text box may also be displayed on the display unit 108 which indicates the distance from the selected tomosynthesis slice 3502 to the x-ray detector 102. It should be noted, that the distance from the tomosynthesis slice 3502 to the x-ray detector 102 is only one type of distance that could be displayed. If, as discussed above, the computer system 106 determines that a particular tomosynthesis slice corresponds to a position proximate to, but not including, a surface of the imaged object, a distance from that tomosynthesis slice to any other tomosynthesis slice may also be calculated and displayed (either alone or along with another distance). Such a distance calculation may provide an approximate depth from the surface of the imaged object to the displayed tomosynthesis slice.

As shown in FIG. 35C, the marker 3402 placed at point A may be visible in the displayed tomosynthesis slice 3502. In an exemplary embodiment, the marker 3402 may be displayed differently when a different tomosynthesis slice is displayed. For example, as shown in FIG. 35C, marker 3402 is filled with dashed lines which indicate that the marker 3402 was placed in a different tomosynthesis slice from the one displayed (tomosynthesis slice 3502). Alternatively, one or more of the size, shape, color, fill pattern, and transparency of marker 3402 may also be changed.

Figure 36:
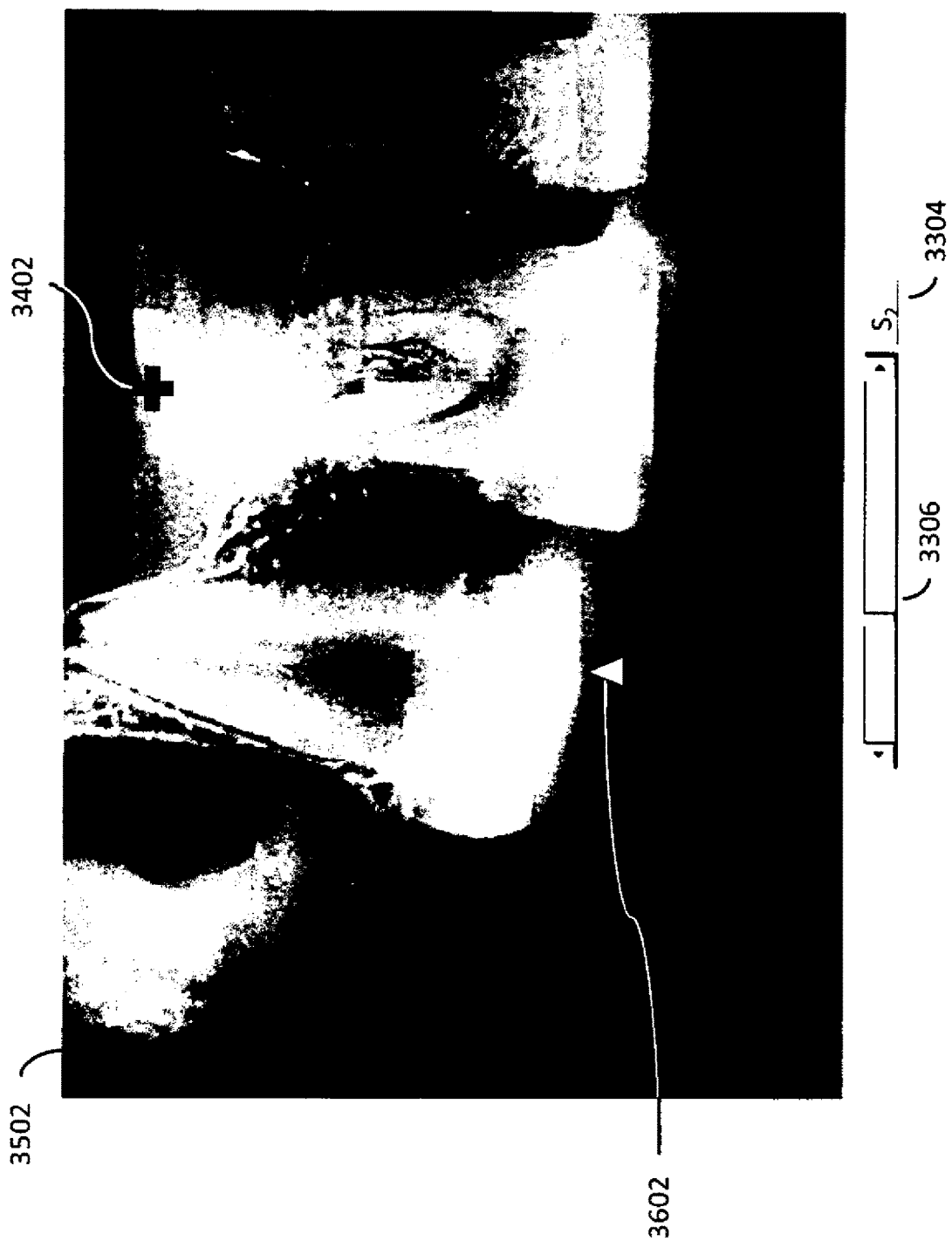
FIG. 36 is an illustration of the other tomosynthesis slice according to an example embodiment herein.

FIG. 36 is an enlarged view of tomosynthesis slice 3502 shown in FIG. 6C. As discussed above, a user may place a second marker 3602 at a desired location. In the example shown in FIG. 36, the second marker 3602 is a triangular shape to distinguish it from the first marker 3302. However, the markers 3402 and 3602 may be the same shape, but have different colors or sizes to distinguish one from the other. The markers 3402 and 3602 may also have different fill patterns or transparencies to distinguish one from the other. As discussed, the second marker 3602 may be set through an input from the input unit 114. For example, if the user is using a mouse, the user may right-click to bring up a menu (as discussed above) that includes one or more commands, such as "Set As Point A", "Set As Point B", "Clear Point A", "Clear Point B", "Clear All Points", "Rotate Measurement Axis", "Reset 3D View".

Figure 37B:
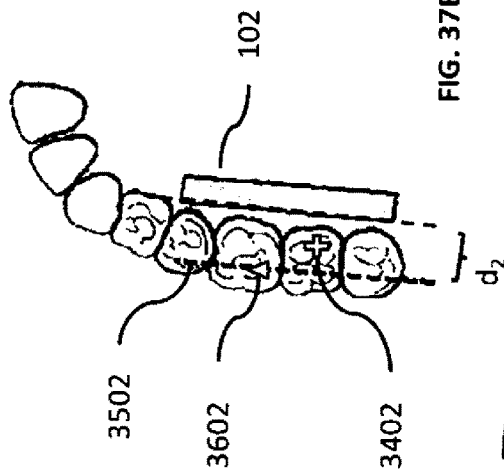
FIGS. 37A-D are illustrations of a two-dimensional x-ray projection image, a tomosynthesis slice, a distance between the tomosynthesis slice and the x-ray detector, and a vector within the image volume according to an example embodiment herein.
Figure 37D:
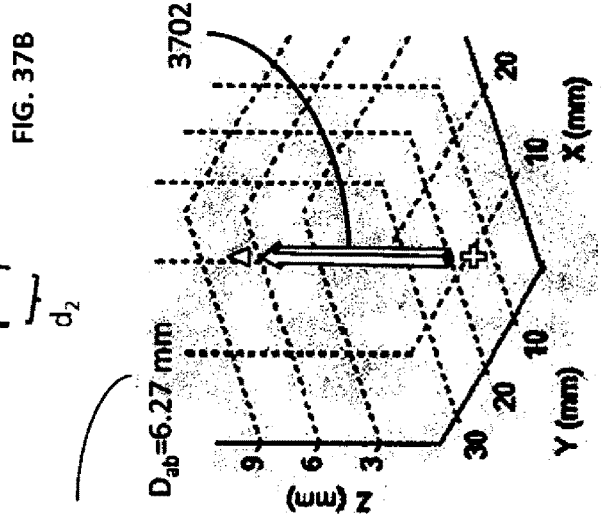
Figure 37A:

As shown in FIGS. 37A-37D, once the second marker 3602 is set, the vector $(V_{ab})$ 3702 may be calculated from the first marker 3402 to the second marker 3602 and displayed three-dimensionally in a coordinate system representing the image volume (see FIG. 37D). As discussed above, the vector magnitude 3704 ($D_{ab}$) may be calculated and displayed as well.

In an exemplary embodiment, however, the user does not have to set the second marker 3602 in order to calculate and display a corresponding vector. Rather, as the user moves the second marker 3602 over the displayed tomosynthesis slice 3502, the computer system 106 dynamically tracks the movement of the second marker 3602 and produces the vector magnitude 3704 and the displayed vector 3702 between points A and B on the volumetric view of the image volume (see FIG. 37D). As discussed in further detail below, depending upon the type of diagnostic image and the selected points, the displayed vector 3702 may correspond to certain anatomical measurements, such as, for example a mesiodistal length, coronoapical length, and buccolingual length Accordingly, even without setting the second marker 3602 at the second measurement point (point B), the user is provided with the vector magnitude and a visual depiction of the vector from the first measurement point (point A) represented by the first marker 3402 to the second measurement point (point B) represented by the second marker 3602. As such, the vector is dynamically updated as the second marker is moved to a new location.

Figures 38A, 38B:
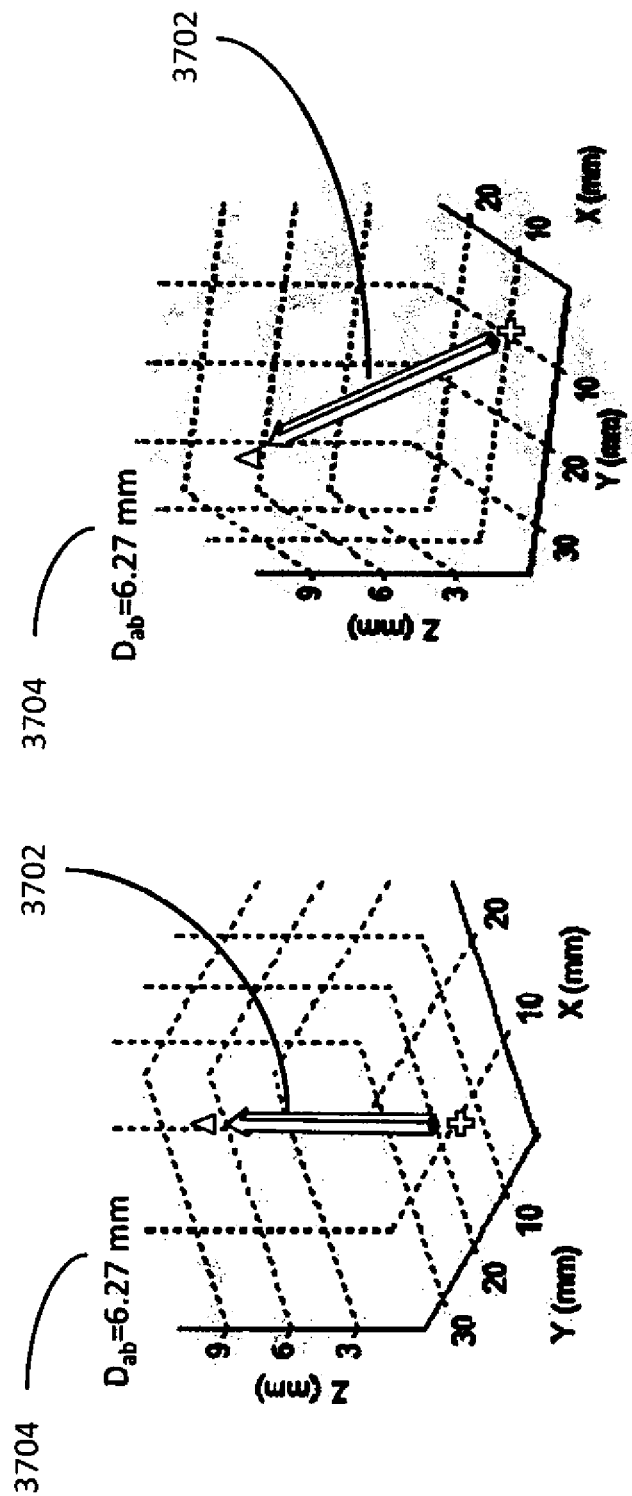
FIGS. 38A-B are illustrations of image volume with a vector therein from two different orientations according to an example embodiment herein.

In an exemplary embodiment, the volumetric view of the image volume may be rotated to provide the user with a different viewing angle, as illustrated in FIGS. 38A and 38B. FIG. 38A is identical to FIG. 37D, which is a default viewing angle for the volumetric view. FIG. 38B is another volumetric view of the image volume, which has been rotated to provide an additional perspective view. The particular perspective view shown in FIG. 38B is only exemplary. The image volume (and the calculated vectors displayed therein) may be viewed from any angle or perspective. In addition, the user may select from a GUI menu one or more preset views, such as, for example, an X-Y view, an X-Z view, and a Y-Z view. Therefore, according to the example embodiment herein, a view of the three-dimensional coordinate space may be rotated.

Figure 37C:

In an exemplary embodiment, a user may quickly navigate through the tomosynthesis stack using one or more of the markers. As discussed, the computer system 106 may cause the display unit 108 to change the displayed tomosynthesis slice based on a command received through the input unit 114. If a user selects a marker corresponding to a tomosynthesis slice which is not currently displayed, the user may enter a command through the input unit 114 which will cause the computer system 106 to retrieve and display the corresponding tomosynthesis slice. The user may select the marker by, for example, double-clicking on the marker, or by right-clicking on the marker to bring up GUI menu system, and then selecting an appropriate command, such "Display Corresponding Tomosynthesis Slice". For example, if tomosynthesis slice 3502 is currently displayed (as shown in FIG. 37C), the user may double-click on the first marker 3402 (corresponding to tomosynthesis slice 3302), and the computer system 106 will then cause the display unit 108 to display tomosynthesis slice 3302 (see FIG. 33C). The slice number display 3304 will then display the corresponding tomosynthesis slice number (e.g., $S_1$). As such, it is possible for a user to quickly return to a view where a marker was originally set, or other views where other markers were set.

While the above description has detailed the placement of first and second markers, more markers may be placed, either on the same tomosynthesis slice or other tomosynthesis slices. The computer system 106 may, in a manner similar to that described above, calculate and display additional vectors corresponding to these markers on display unit 108. The respective magnitudes of these vectors may also be displayed (like in FIG. 37D), either concurrently with other vector magnitudes or individually.

Figure 39A:
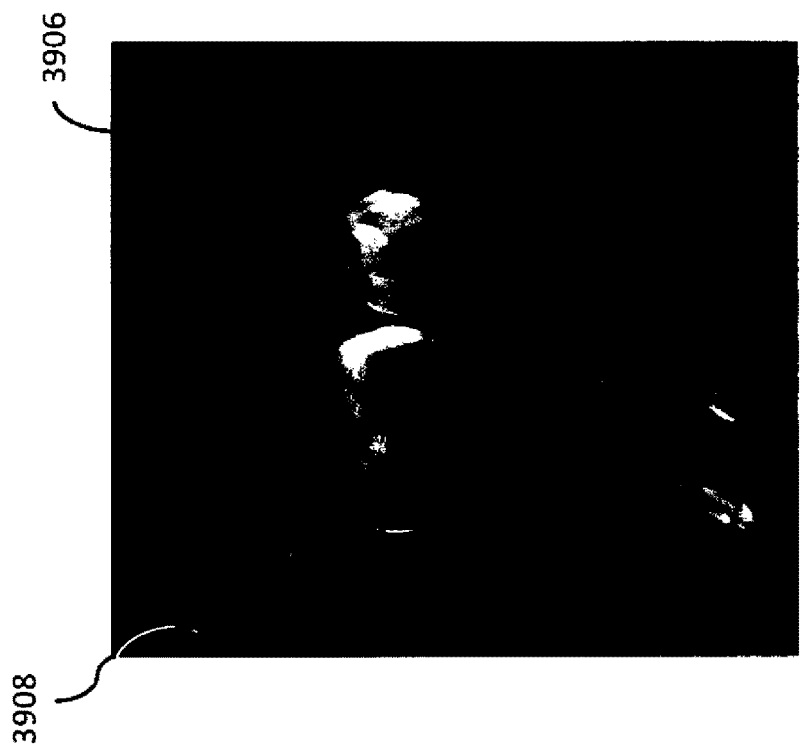
FIGS. 39A-C are illustrations of a two-dimensional x-ray projection image, a tomosynthesis slice, and a volumetric image of the image volume according to an example embodiment herein.

FIGS. 39A-41B illustrate another exemplary embodiment. FIGS. 39A-39C are illustrative of three images which may be simultaneously or individually displayed on display unit 108. In FIG. 39A, a two-dimensional x-ray projection image 3902 corresponding to the 0° angle shown in FIG. 1A is displayed on display unit 108. In the manner discussed above, a user may select a tomosynthesis slice 3904 from the tomosynthesis stack (using, for example, scroll-bar 3306), which may also be displayed on display unit 108. In that regard, the user may use a scroll bar 3306 to scroll between tomosynthesis slices in the tomosynthesis stack, and the corresponding slice number may be displayed in slice number display 3304. As discussed above, the computer system 106 may generate a three-dimensional volumetric image 3906 (FIG. 39C) of the image volume. In the exemplary embodiment illustrated in FIG. 39C, the three-dimensional volumetric image 3906 is displayed on display unit 108 as opposed to a volumetric view of the image volume (e.g., FIG. 33D). However, both the three-dimensional volumetric image 3906 and a volumetric view of the image volume may be displayed on display unit 108 at the same time.

Figure 39B:
Figure 39C:
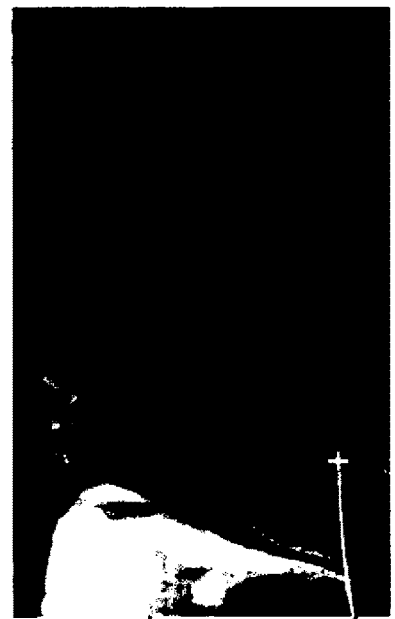

As illustrated in FIG. 39C, coordinate axes 3908 may also be provided to show the user the viewing orientation of the volumetric image. Rather than labeling the coordinate axes in Cartesian nomenclature, the axes may be described using anatomical nomenclature (e.g., mesiodistal (M), coronoapical (C), and buccolingual (L)) to provide the user with information regarding the anatomical orientation of the image volume. In an exemplary embodiment, the ends of the scroll bar 3306 may be labelled with corresponding descriptions of the axes. For example, if the particular diagnostic image results in the tomosynthesis stack being arranged along the buccolingual axis then the ends of the scroll bar 3306 may labelled "buccal" and "lingual". Thus, the user can easily determine which direction to scroll the slider to move in one anatomical direction or another.

As described above, once the user has selected a particular tomosynthesis slice, a first marker 3910 may be placed at a first measurement point (point A), as illustrated in FIG. 39B. The user may then select a second tomosynthesis slice 4002 and place a second marker 4004 to designate a second measurement point (point B), as illustrated in FIG. 40B. As described above, the second tomosynthesis slice 4002 may be the same slice or a different slice. As discussed, the user may move the second marker 4004 to any location on the second tomosynthesis slice 4002 and the computer system 106 may dynamically calculate and update the magnitude of a vector 4006 from the first measurement point to the second measurement point. The magnitude of that vector (corresponding to a distance between the two points) may be displayed, along with the magnitudes of the individual vector components, in a text box 4008 (as illustrated in FIG. 40C). As shown in FIG. 40C, the vector 4006 may be displayed in partial relief, that is the vector 4006 may be partially shaded when the vector traverses through a structure. The vector 4006 may also be shown in relief by other visual means such as, for example, a dashed line.

Figures 41A, 41B:
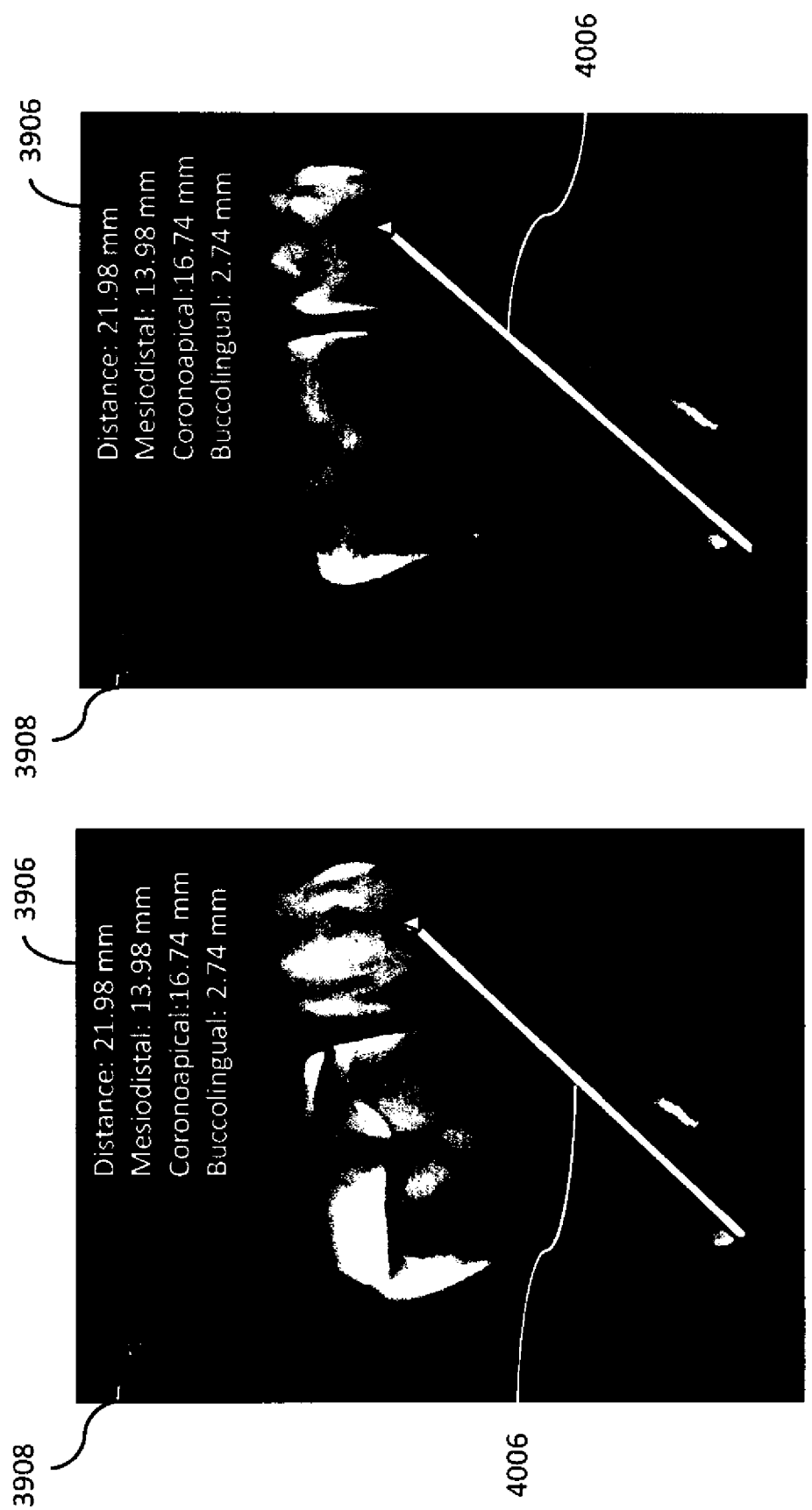
FIGS. 41A-B are volumetric images of the image volume from different orientations with a vector disposed therein.

In an exemplary embodiment, the volumetric image 3906 may be rotated by the user to provide different views of both the volumetric image 3906 and the vector 4006 contained therein. For example, as shown in FIG. 41A, the volumetric image 4006 has been rotated to provide a clearer view of the occlusal surface of the imaged tooth. The coordinate axes 3908 have also been rotated to provide the user with an indication of the anatomical directions. In FIG. 41B, the volumetric image 3906 has been rotated to provide a view of the coronoapical-mesiodistal plane (i.e., in a direction of the buccolingual axis). For simplicity, vector 4006 has not been shown in relief in FIGS. 41A-41B, however, the computer system 106 may cause the display unit 108 to display vector 4006 in relief to provide additional visualization of the vector 4006 for the user.

The volumetric image 3906 may be rotated through a variety of means. For example if the input unit 114 is a mouse, the user may click on a part of the display volumetric image 3906 and drag the mouse to displayed volumetric image 3906 to rotate in a corresponding manner. In another example, a GUI menu may be displayed which shows one or more icons that may be clicked on by the user to cause the volumetric image to rotate. In yet another example, the computer system 106 may display a list of predetermined viewing perspectives which the user may select from. If the type of diagnostic image is known, a set of corresponding views which may be useful for the particular diagnostic operation may be presented in the form a GUI menu by the computer system 106. The user may then select one of those views which will be displayed by display unit 108. For example, if the diagnostic operation is a measurement of thickness of the lingual and buccal plates, a view along the mesiodistal axis (i.e., of the buccolingual plane) may be predetermined view selectable from the GUI menu.

Accordingly, by virtue of the example embodiments described herein, 3D measurement in a stack of tomosynthesis images is provided, even across or within images of the stack. For example, it is possible to measure the distances between points on objects or structures represented by tomosynthesis images, even though the images themselves are only two-dimensional. Moreover, it is possible to provide useful information based on such measurement.

Measuring and Visualizing Lingual and Buccal Plate Thickness

As described below, methods, systems, apparatuses, and computer program products are provided for measuring the thicknesses of the lingual and buccal plates.

Figure 42A:
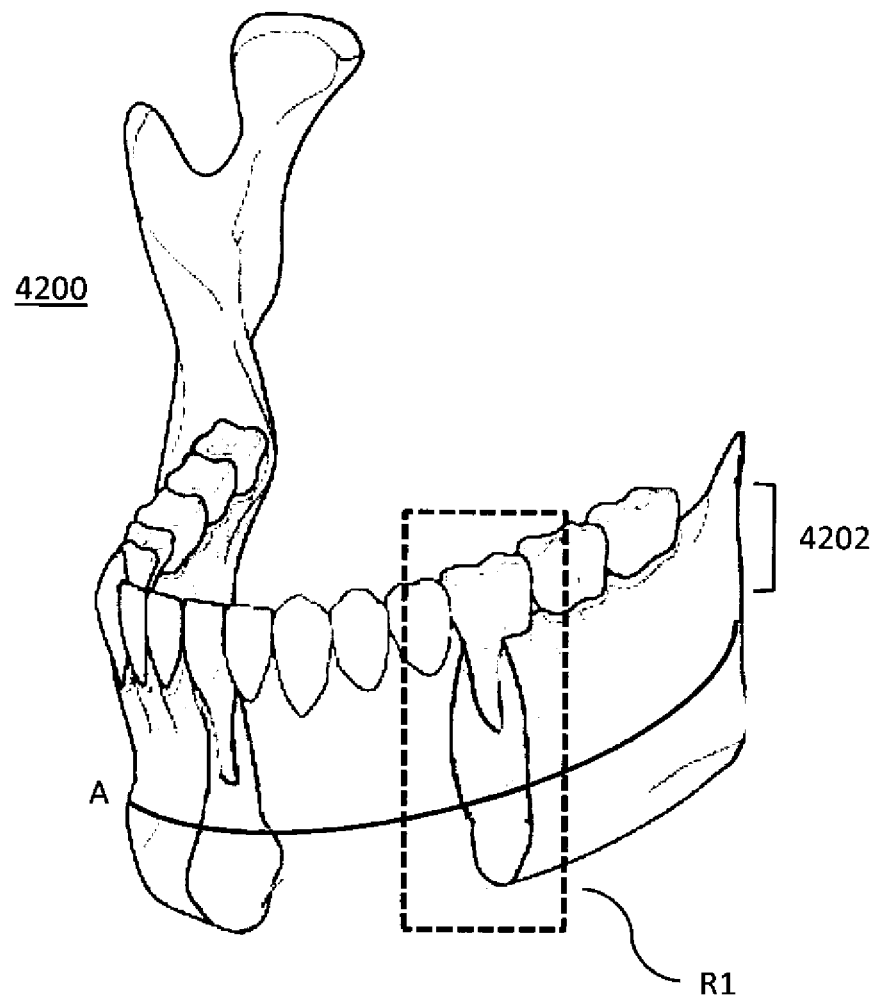
FIG. 42A is an illustration of the human mandible.
Figure 42B:
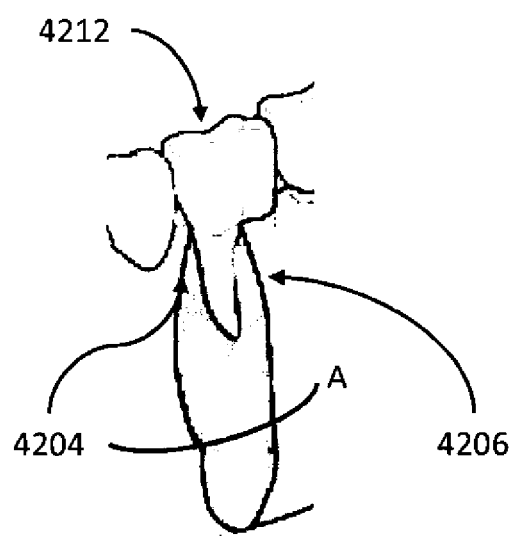
FIG. 42B is an illustration of region R1 in FIG. 42A.

FIG. 42A is a perspective view of the human mandible 4200. The mandible 4200 includes the alveolar process 4202 (indicated as region above line A), which is a thickened region that contains the tooth sockets. As shown in FIG. 42B, the alveolar process 4202 includes a lingual bone plate 4204 and a buccal bone plate 4206 disposed on opposite sides of a tooth cavity for tooth 4212. If a problem arises with tooth 4212 such that it must be replaced with an implant, the lingual plate 4204 and the buccal plate 4206 must have sufficient strength to support the implant. If the lingual plate 4204 and the buccal plate 4206 lack sufficient strength, a fracture may occur when the implant is exposed to forces incurred during the chewing process. The respective strengths of the lingual plate 4204 and the buccal plate 4206 are directly related to their respective thicknesses in a region that supports the implant. Traditional x-ray imaging in the periapical direction is incapable of resolving the thicknesses of the lingual and buccal plates because, for one, the imaging direction (i.e., the direction in which an x-ray travels from the x-ray source) is generally perpendicular to the lingual and buccal plates. However, the imaging direction is not the only reason traditional x-ray imaging is incapable of resolving the thicknesses of the lingual and buccal plates, as explained below.

Figure 43A:
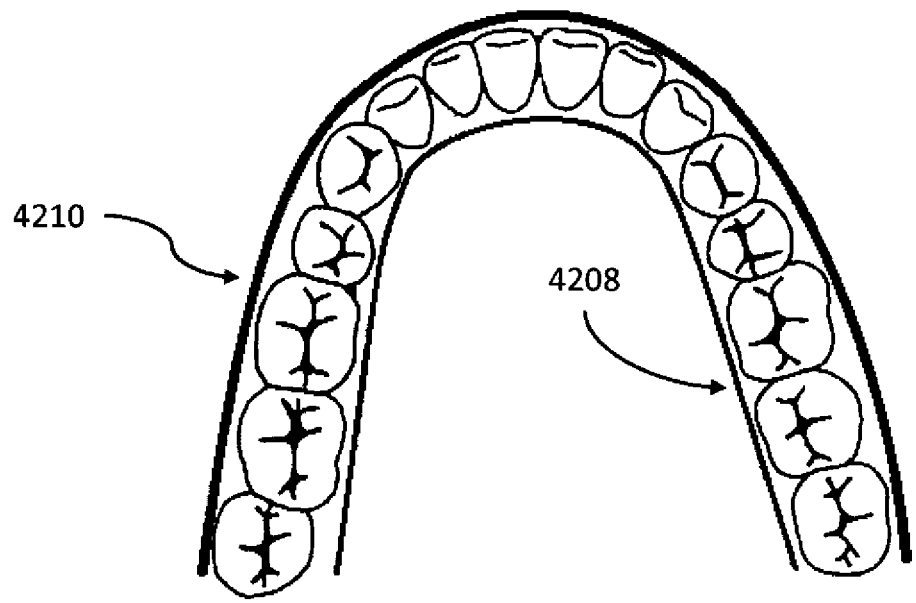
FIG. 43A is an illustration of the human maxilla from an occlusal viewpoint.
Figure 43B:
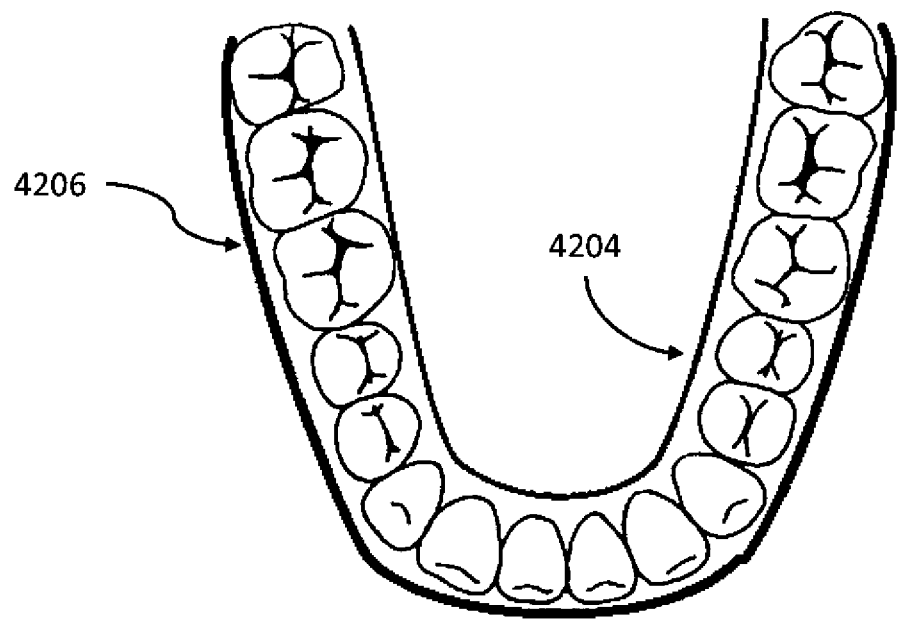
FIG. 43B is an illustration of the human mandible from an occlusal viewpoint.
Figure 60A:
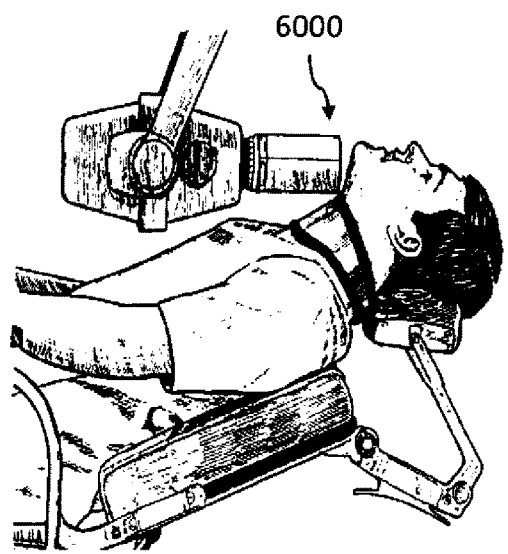
FIG. 60A is an illustration of a person positioned for an occlusal image of the mandible according to a conventional technique.
Figure 60B:
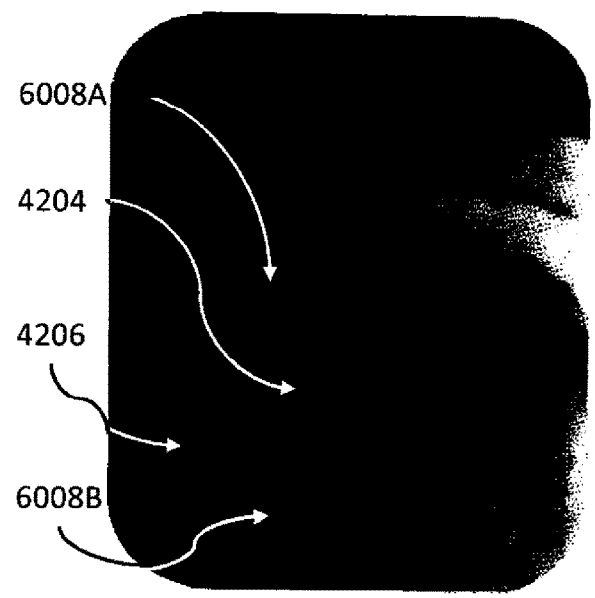
FIG. 60B is a traditional two-dimensional x-ray image.
Figure 60C:
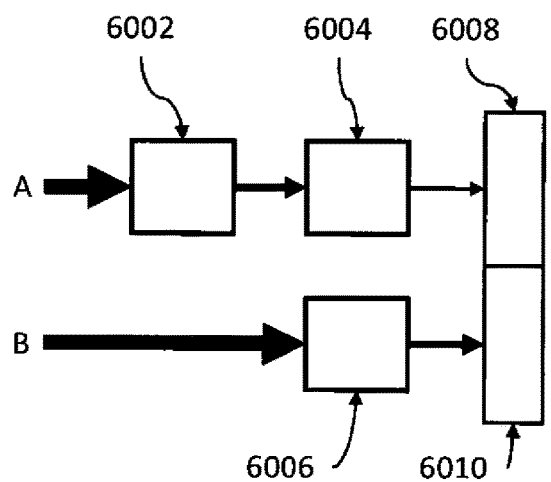
FIG. 60C is an illustration of two x-rays propagating through matter.

FIGS. 43A and 43B are illustrations of the maxilla (FIG. 43A) and mandible (FIG. 43B) from the occlusal direction with the lingual plates 4204 and 4208 and the buccal plates 4206 and 4210 shown. Unlike when imaging in the periapical direction, here the lingual and buccal plates are substantially parallel to the imaging direction. However, as discussed above in reference to FIGS. 60A & 60C an traditional x-ray image lacks depth information and overlapping objects easily obscure one another. For example, as shown in FIG. 60B, at least a portion of an incisor tooth 6008A and a portion of the buccal plate 4206 lie in the same x-ray path. Thus, the incisor tooth 6012A obscures at least a portion of the buccal plate 4206, making it difficult to precisely determine the boundaries of the buccal plate 4206. In a similar fashion tooth 6008B obscures the view of the lingual plate 4204.

Moreover, a thickness measurement of the lingual and buccal bones from occlusal direction using a traditional x-ray image may lead to an inaccurate measurement, as discussed below.

Figure 60D:
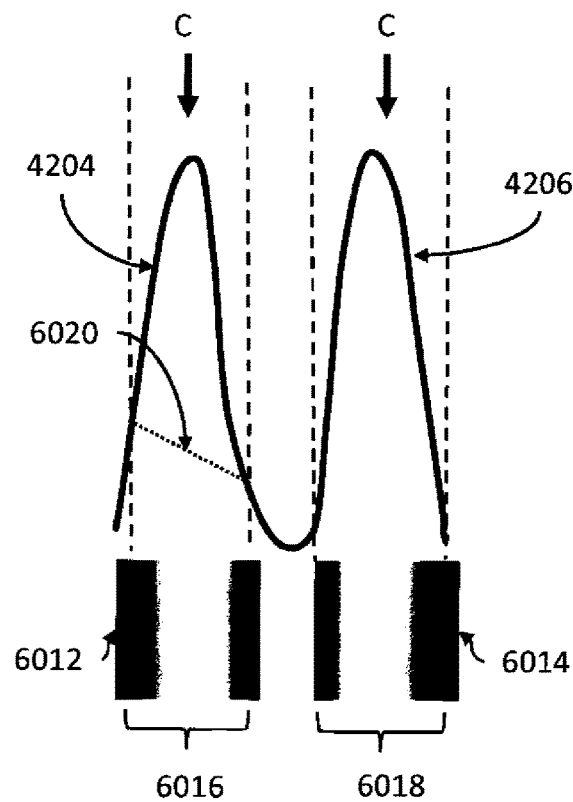
FIG. 60D is an illustration of lingual and buccal plates imaged according to a conventional technique.

FIG. 60D shows cross-sectional views of the lingual plate 4204 and buccal plate 4206, and the resulting x-ray projection images (6012 and 6014) from those plates for x-rays incident in the direction of arrow C. If one were to measure the width of the white portion of images 6012 and 6014 in an attempt to determine the thicknesses of the lingual plate 4204 and the buccal plate 4206 (as indicated by 6016 and 6018) at a particular depth in the imaging direction (defined by ray C), the resulting measurement may over represent the thicknesses of the plates. This because the white portions in the image represent the widest points of the imaged object which may not be at the same depth. This is illustrated in FIG. 60D. The thickness measurement 6016 corresponds to a plane 6020 that is angled relative to the occlusal surface of the tooth (which is generally perpendicular to the imaging direction). Thus, the lack of depth information may lead to an improper diagnostic measurement.

Figure 44:
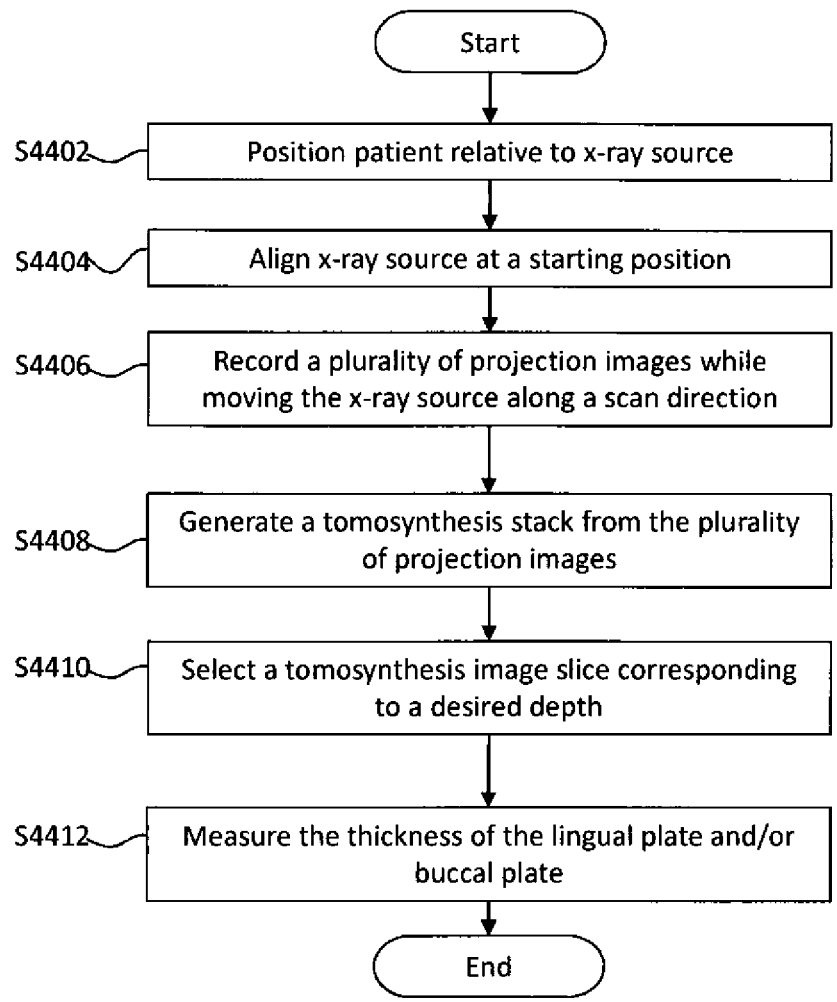
FIG. 44 is a flowchart illustrating an exemplary method of measuring the thickness of the lingual and buccal plates.

FIG. 44 is a flow chart illustrating the steps in measuring the thickness of the lingual and buccal plates, in accordance with one exemplary embodiment.

Figure 45:
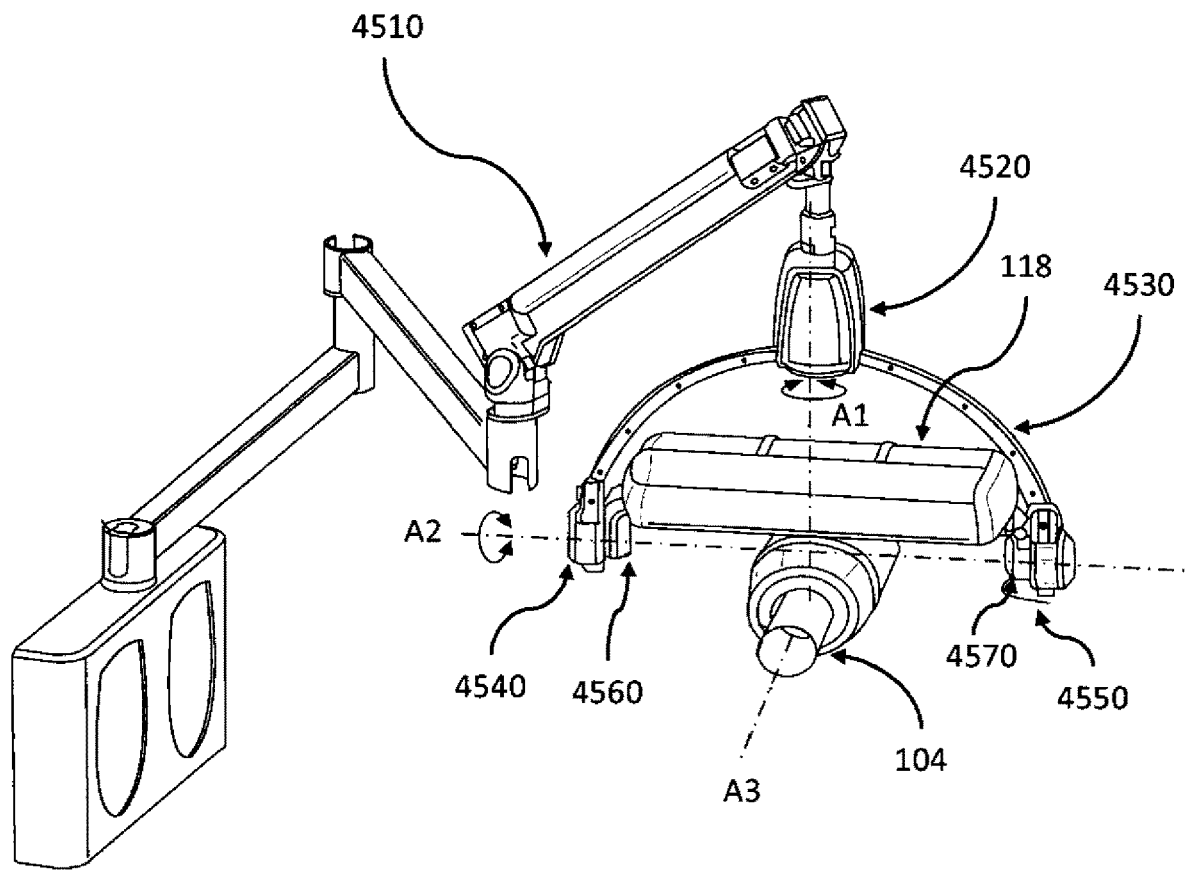
FIG. 45 is a perspective view of a portion of an exemplary tomosynthesis system 100.

First, in step S4402 the patient is positioned relative to the x-ray source 104. More specifically, an x-ray detector 102 (e.g., one of the intraoral sensors described above) is carefully positioned inside of a patient's mouth. The patient bites down gently on the x-ray detector 102 to fix its position within the patient's mouth. A protective cover may be placed over the x-ray detector 102 to prevent the x-ray detector 102 from being damaged, as well as for sanitary reasons. Next, the x-ray source 104 is moved to an appropriate starting position for the radiographic scan (S4404). FIG. 45 is an exemplary illustration of an x-ray source 104 mounted in such a manner that it may be positioned at any location within a three-dimensional space.

As shown in FIG. 45, the x-ray source 104 may be connected to an adjustable arm 4510, which may be segmented and include one or more joints such as: a hinge, a swivel, a universal joint, or the like. The adjustable arm 4510 allows the x-ray source 104 to freely translate in three-dimensional space. Attached to one end of the adjustable arm 4510 is a vertical member 4520. The other end of the adjustable arm 4510 may be mounted to a stationary structure, such as a wall or a ceiling. The vertical member 4520 is suspended vertically from the adjustable arm 4510 by a joint that allows the vertical member 4520 to freely rotate about an axis (A1) substantially defined by the vertical member 4520, regardless of the position and orientation of the adjustable arm 4510. The vertical member 4520 includes a bearing assembly which acts as a channel through the vertical member 4520. A yoke 4530 is movably constrained within the channel, and can be angularly displaced through the bearing assembly and thus through the vertical member 4520. A brake may hold the yoke 4530 in place and substantially prevent any motion of the yoke 4530 through the bearing assembly, thus locking the position of the yoke 4530 relative to the vertical member 4520. A brake release button may also be provided such that an operator can release the brake and allow the yoke 4530 to rotate through the vertical member 4520.

The motorized stage 118 may include arms 4560 and 4570 which are movably attached to the yoke ends 4540 and 4550, respectively, each point of attachment forming a pivot such that the motorized stage 118 can be pitched about an axis (A2) which is substantially defined by the yoke ends 4540 and 4550 and substantially orthogonal to the axis (A3) of the x-ray source 104. In the exemplary arrangement illustrated in FIG. 45, the x-ray source 104 may be appropriately positioned at any desired location in three-dimensional space such that the axis A3 of the x-ray source 104 is substantially perpendicular to the surface of the x-ray detector 102.

Figure 46:
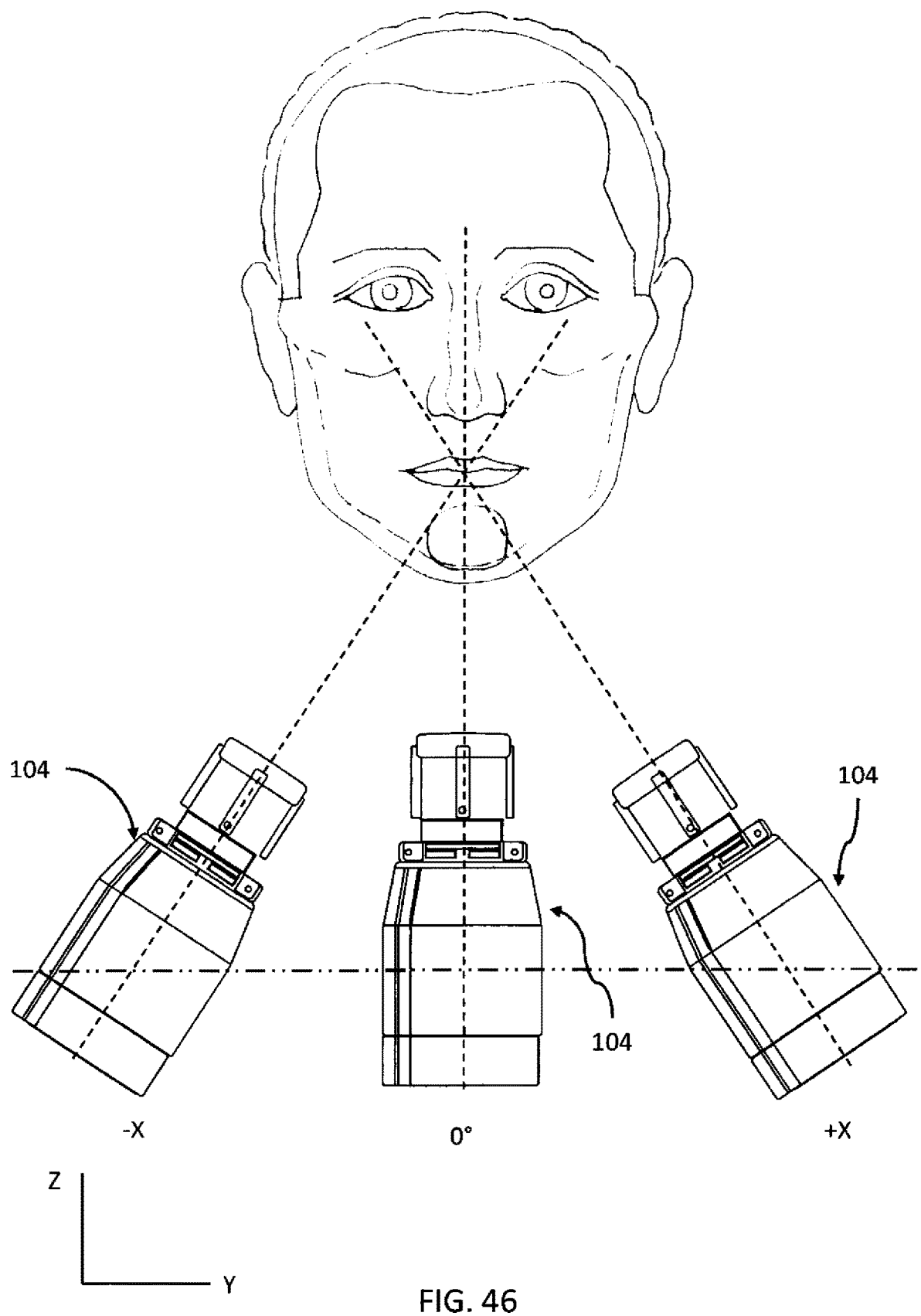
FIG. 46 is an illustration of an x-ray source at different positions during an exemplary radiographic scan.
Figure 47:
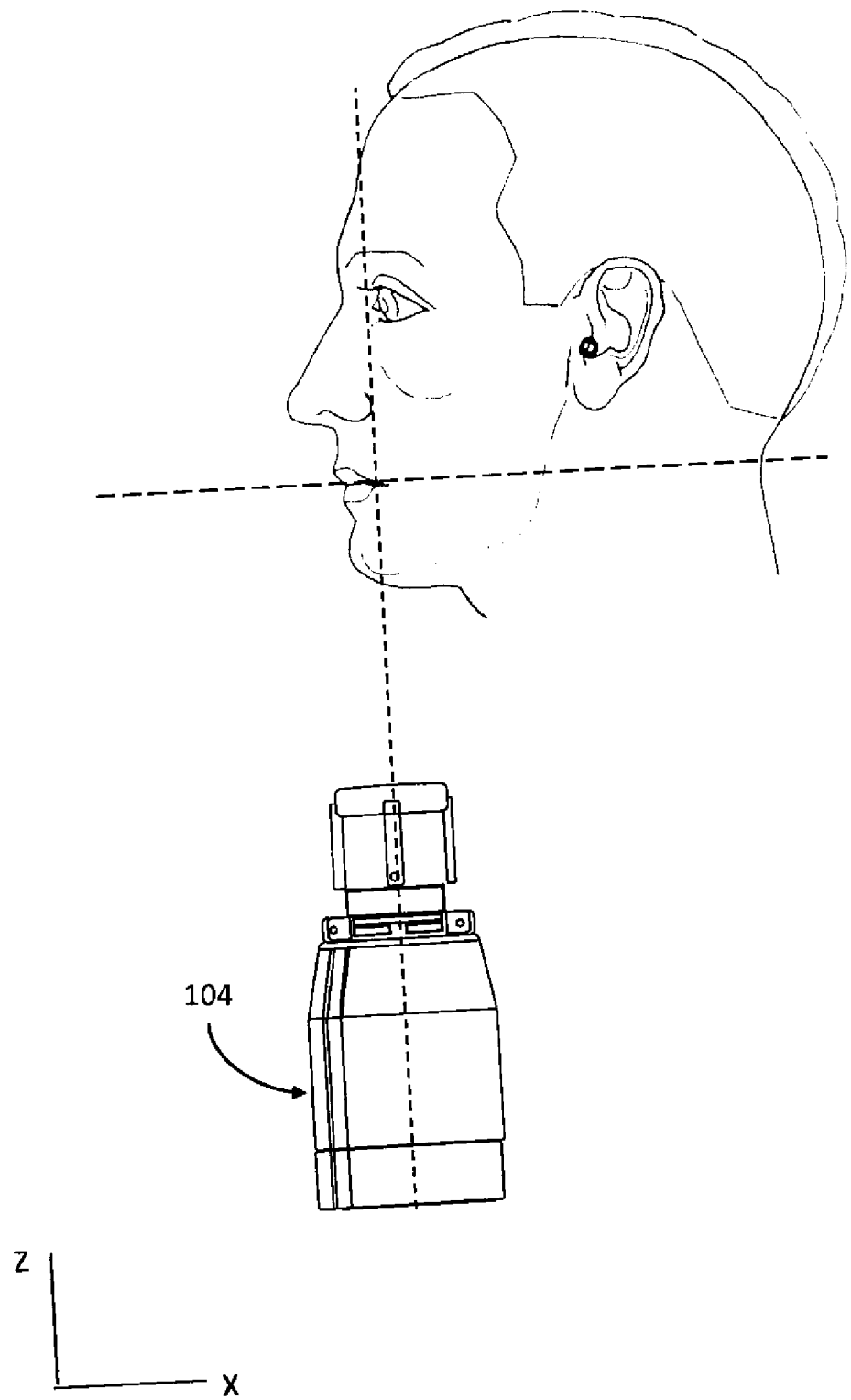
FIG. 47 is an illustration of an x-ray source positioned relative to a patient.
Figure 48:
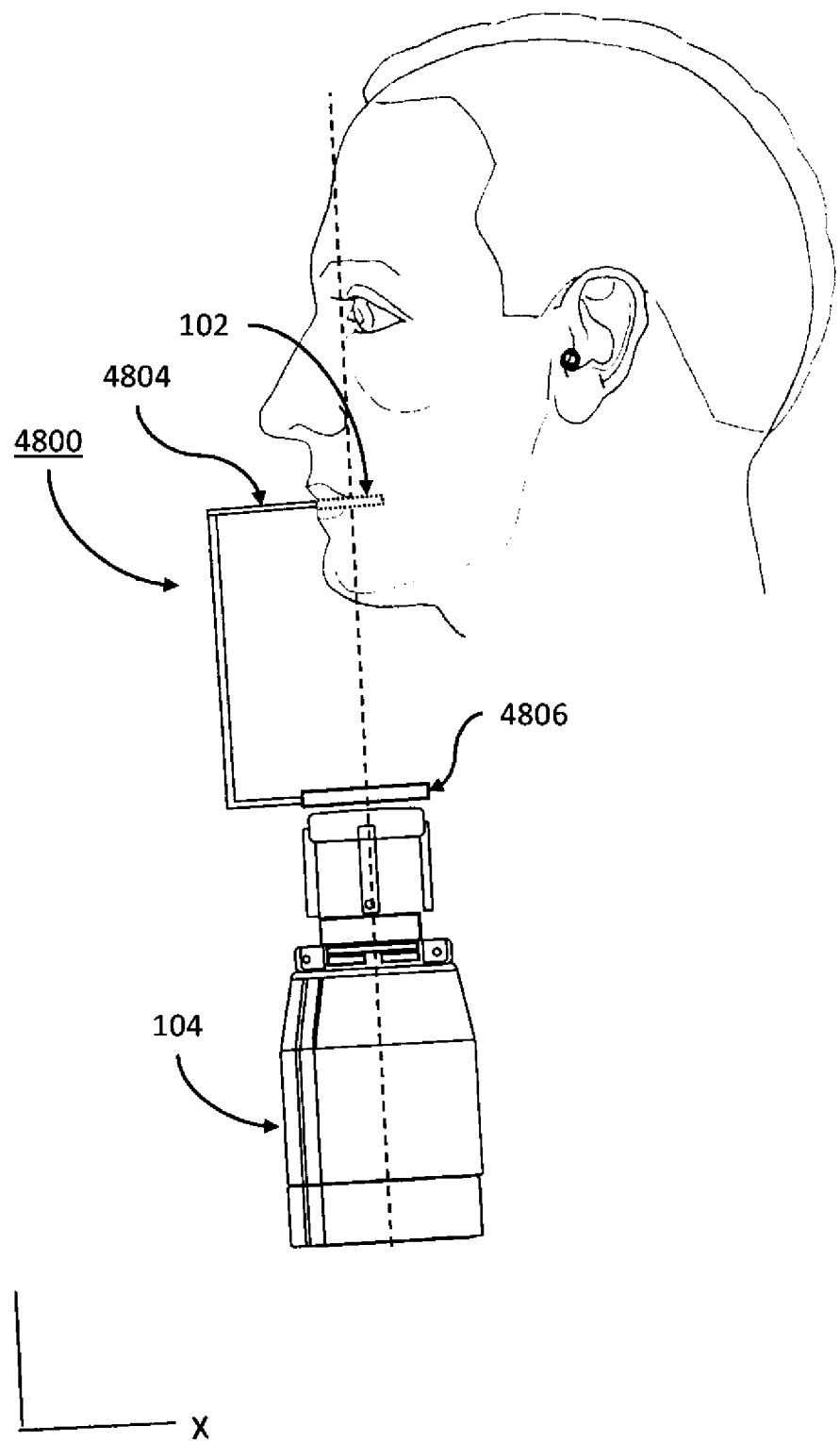
FIG. 48 is an illustration of an x-ray source positioned relative to a patient with the aid of an aiming device.

Returning to the discussion of step S4402, if the thicknesses of the lingual plate 4204 and the buccal plate 4206 in the mandible bone are desired, the x-ray source 104 should preferably be positioned below the patient's jaw, as illustrated in FIGS. 46-48. With this configuration, the teeth and the mandible (including the lingual plate 4204 and the buccal plate 4206) comprise the object 50 and sub-objects illustrated in FIG. 1A. In an exemplary embodiment, the x-ray source 104 is initially positioned at the 0° position in the scan angle, which typically corresponds to a middle position in the scanning range (S4404). However, the x-ray source 104 may be initially positioned at any location within the scanning range. As shown in FIG. 47, it is preferable that a plane corresponding to the surface of the x-ray detector 102 is orthogonal to the imaging direction of the x-ray source 104. An aiming device 4800 may be provided to aid with the alignment of the x-ray source 104 relative to the x-ray detector 102, as illustrated in FIG. 48.

FIG. 48 shows the x-ray source 104 which has been positioned with respect to the x-ray detector 102 with the assistance of an aiming device 4800. The aiming device 4800 includes an arm 4804 which is connected to the x-ray detector 102 and the aiming ring 4806. The connections between (i) the arm 4804 and the x-ray detector 102 and (ii) the arm 4804 and the aiming ring 4806 may be made by a mechanical connection (e.g., a snap-fit connection or a friction fit connection), a magnetic connection, an electrical connection, a chemical connection (e.g., glue), or a combination thereof. For example, the cross-sectional dimension of the arm 4804 may be substantially the same as an opening (see opening 4904 in FIG. 49) in the aiming ring 4806 that receives the arm 4804, such that there is a significant amount of friction between the opening and the arm 4804 when the arm 4804 is inserted into the opening, thus establishing a friction fit. The amount of friction is sufficient to ensure that the aiming ring 4806 does not move during the radiographic scan. The arm 4804 may also extend through an opening so that the distance between the aiming ring 4806 and the x-ray detector 102 is adjustable and may be appropriately set by an operator. Once that distance is set, the friction between the opening and the arm 4804 will prevent the aiming ring from moving further. An opposite end of the arm 4804 may include a holder that is configured to receive the x-ray detector 102 via a snap-fit connection.

Figure 49:
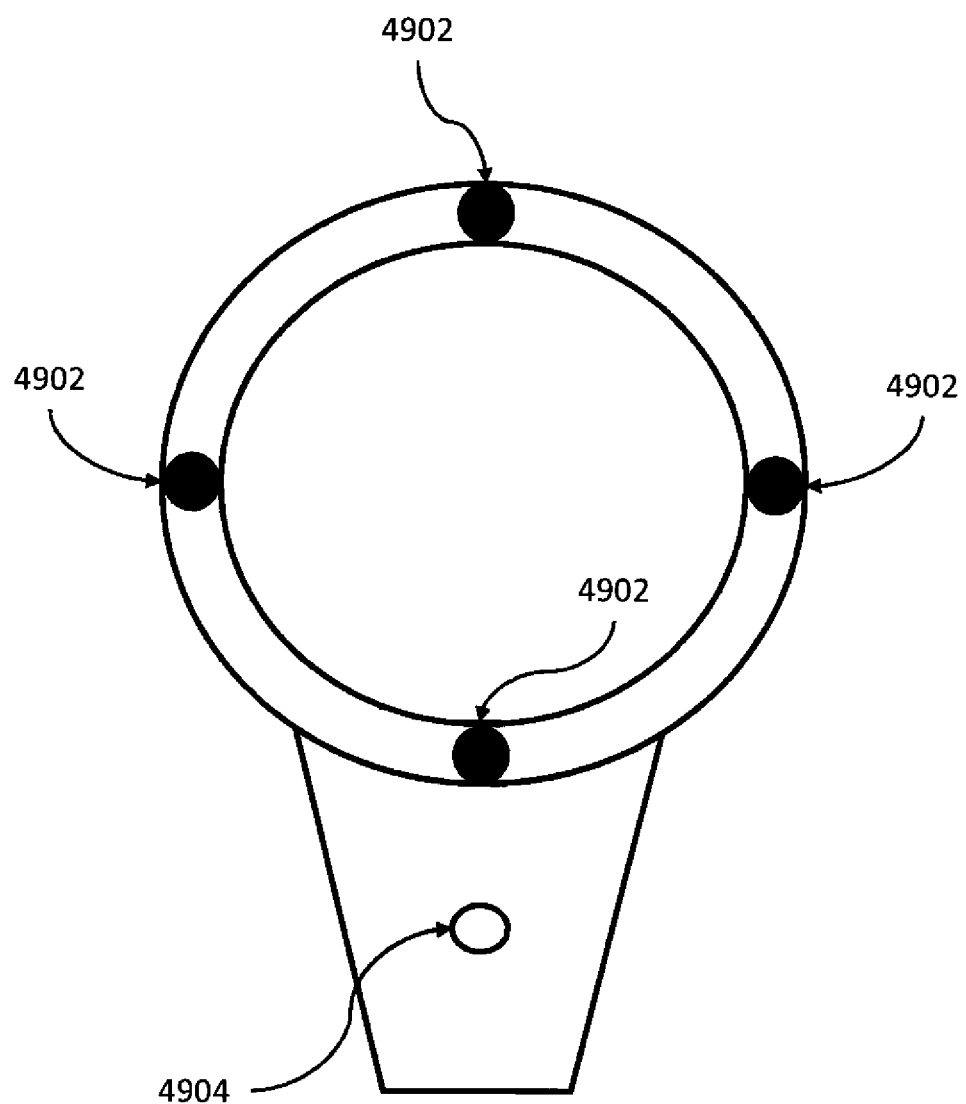
FIG. 49 is an illustration of an exemplary aiming device.

The aiming ring 4806 may also include a plurality of alignment markers 4902, as shown in FIG. 49. The alignment markers 4902 may be formed from a known material whose attenuation factor is known. The alignment markers 4902 may be visible in the recorded two-dimensional x-ray projection image, and can serve as reference markers during the image processing. The alignment markers 4902 may also be used to measure the system geometry (i.e., the spatial relationship between the x-ray source and the x-ray detector). While a particular geometry may be assumed, the actual geometry may differ from the assumed geometry, due to misalignment of the x-ray source, vibration or flexure of the arm of the aiming ring (or the structure on which the x-ray source is mounted), or motion of the patient. Since, in one embodiment, the system geometry may determine which backprojection matrix is used and may also modify the filtering step in a filter backprojection, the positions of the alignment markers 4902 in the recorded image can provide useful information regarding the system geometry. As noted above, the aiming ring 4806 may also be provided with one or more openings 4904 through which the aim 4804 may be inserted to connect the aiming ring 4806 to the x-ray detector 102.

Figure 50:
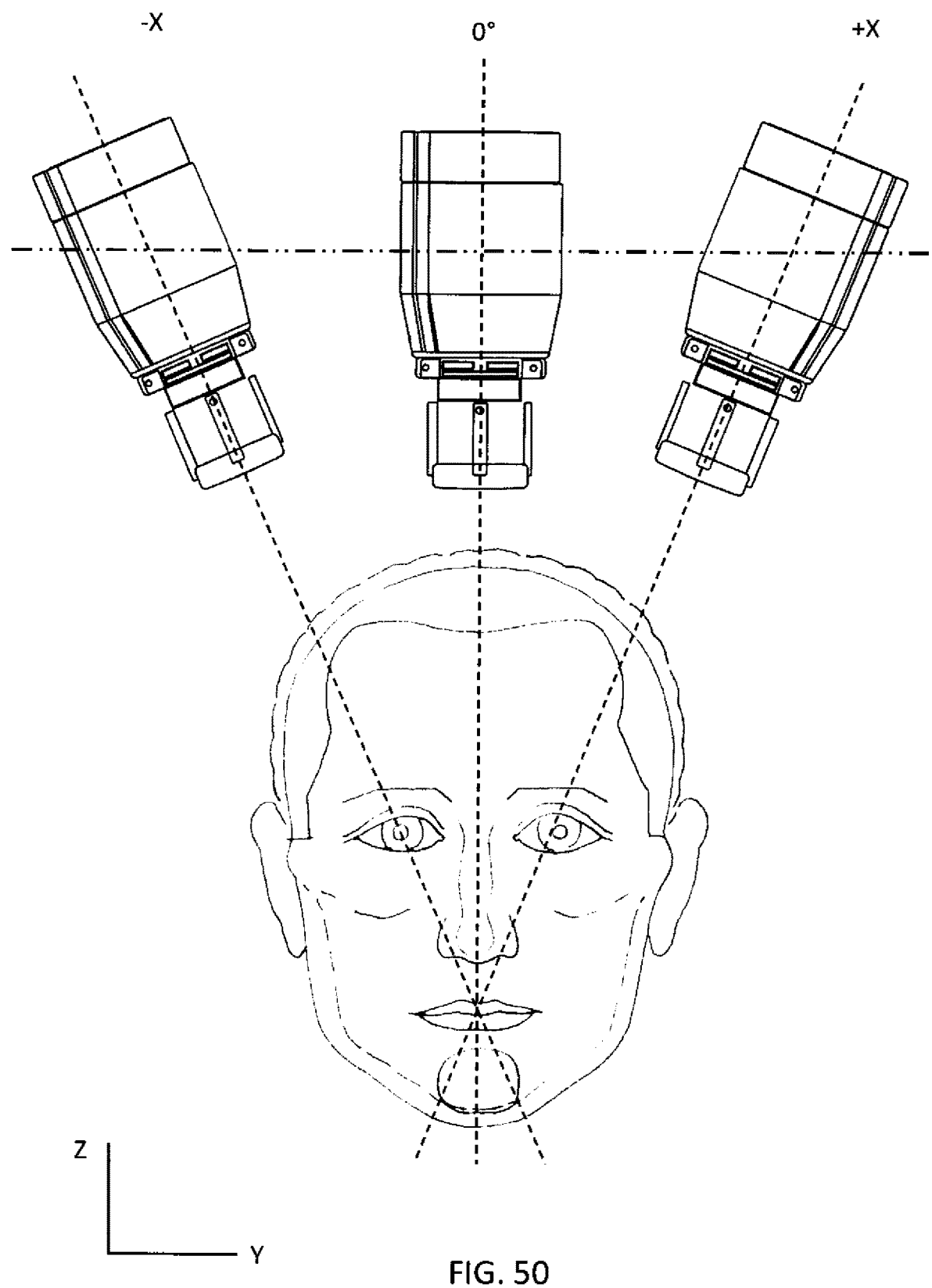
FIG. 50 is an illustration of an x-ray source at different positions during an exemplary radiographic scan.
Figure 51:
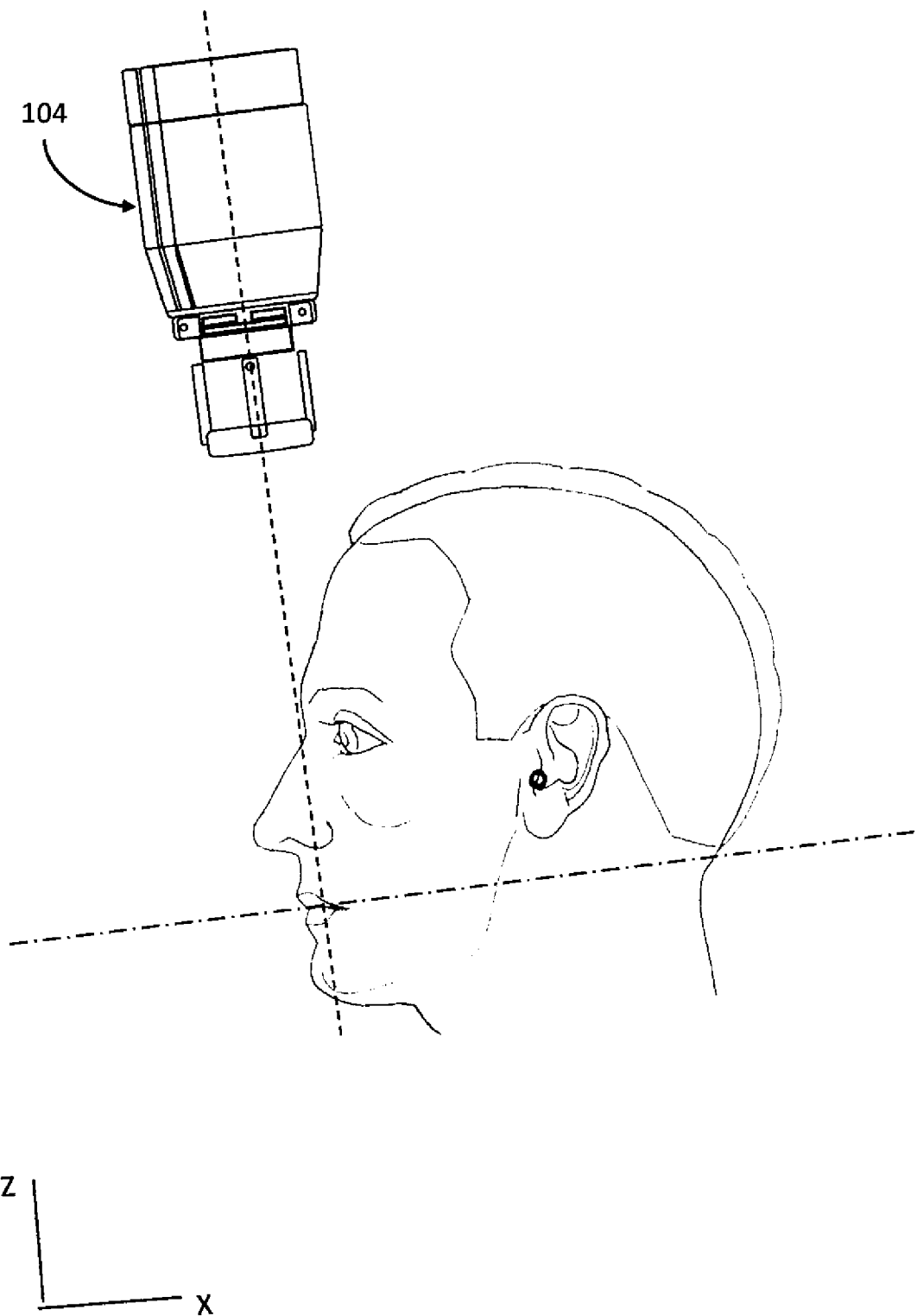
FIG. 51 is an illustration of an x-ray source positioned relative to a patient.
Figure 52:
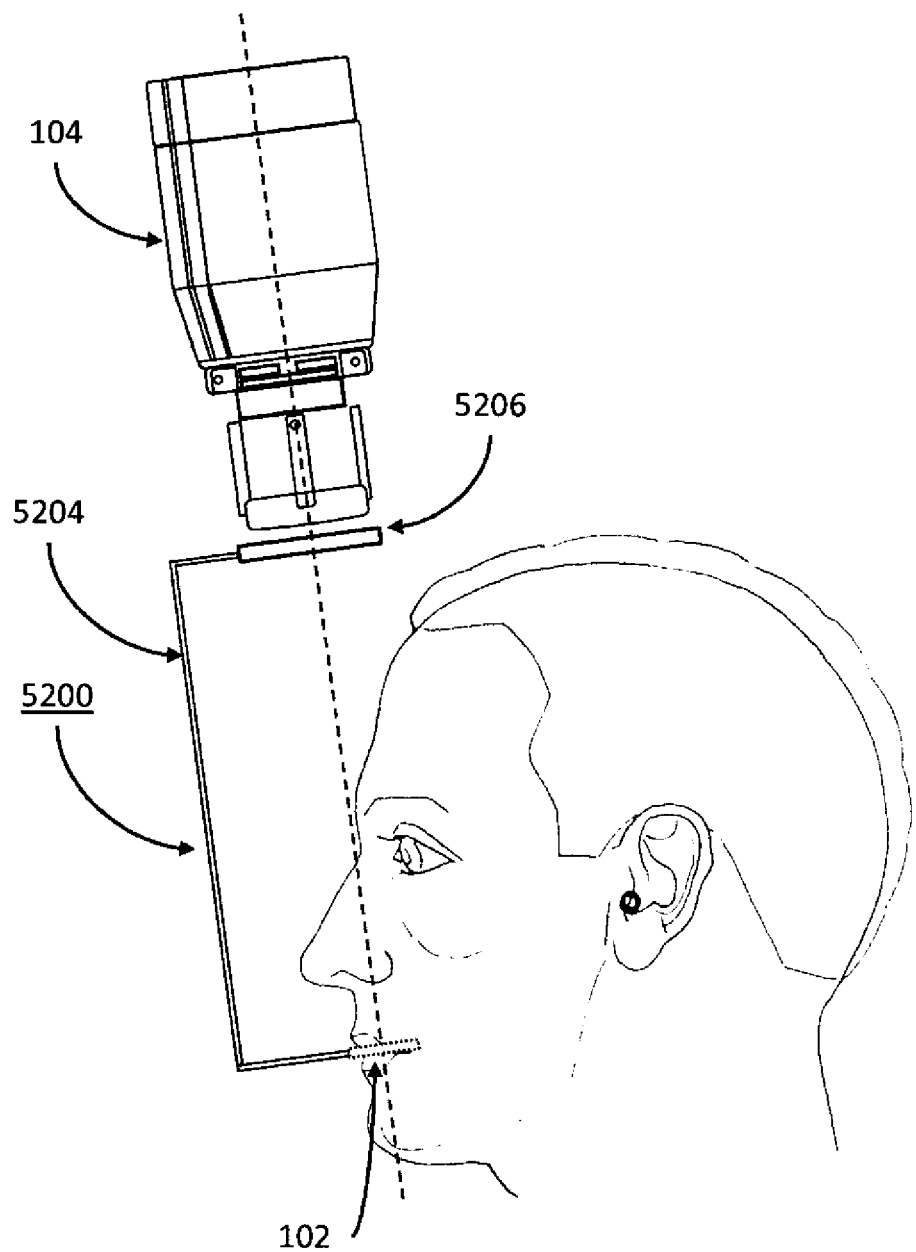
FIG. 52 is an illustration of an x-ray source positioned relative to a patient with the aid of an aiming device.

A similar process may be performed if the thicknesses of the lingual plate 4208 and the buccal plate 4210 in the maxilla are desired. In this case, the x-ray source 104 may preferably be positioned above the patient's head, as illustrated in FIGS. 50-52. Like with a scan of lingual plate 4204 and the buccal plate 4206 in the mandible, the x-ray source 104 may preferably be positioned such that the imaging direction defined by the axis of the x-ray source 104 is substantially orthogonal to the plane of the x-ray detector 102, as illustrated in FIG. 51.

As shown in FIG. 52, an aiming device 5200 may also be used to aid in the alignment of the x-ray source 104 with the x-ray detector 102. Like aiming device 4800, aiming device 5200 includes an arm 5204 which is connected to the x-ray detector 102 and the aiming ring 5206. One or more of the components of the aiming device 5200 may be the same as the components of the aiming device 4800. The components of the aiming device 5200, however, may also be different from those included in aiming device 4800, and specifically constructed for use in imaging the lingual plate 4208 and the buccal plate 4210 of the maxilla from an occlusal direction. Like with aiming device 4800, the connections between (i) the arm 5204 and the x-ray detector 102 and (ii) the arm 5204 and the aiming ring 5206 may be made by a mechanical connection (e.g., a snap-fit connection or a friction fit connection), a magnetic connection, an electrical connection, a chemical connection (e.g., glue), or a combination thereof. Like with aiming device 4800, the distance between the aiming ring 5206 and the x-ray detector 102 may be adjustable.

With the x-ray source 104 properly aligned with the x-ray detector 102, the computer system 106 initiates the scanning operation to record a plurality of projection images in step S4406. As discussed above, on-board motor controller 120 controls the motorized stage 118 so as to translate the x-ray source 104 through a plurality of locations within the scan angle 112, as illustrated in FIG. 46.

FIG. 46 illustrates the translation (and rotation) of the x-ray source 104 during an imaging operation over a scan angle of X degrees (which may, for example, be ±20°). In FIG. 46, the x-ray source 104 translates along the motorized stage 118, but also rotates such that the x-rays 110 emitted from each of the different locations converge substantially at a focal spot 122, as illustrated in FIG. 1A. Of course, in another embodiment, the x-ray source 104 may be moved in a curved scan path 132 or a circular scan path 134, as described above.

At each location, the x-ray detector 102 records the intensity of the x-rays 110 received from the x-ray source 104 and converts those x-rays 110 into electrical signals. The computer system 106 then processes those electrical signals to generate a two-dimensional projection image. The x-ray source 104 then moves to the next position and a subsequent two-dimensional projection image is recorded. This process repeats at each desired scan location over the scanning range to generate a plurality of two-dimensional projection images.

In step S4408, the computer system 106 processes the plurality of projection images to reconstruct a series of two-dimensional tomosynthesis image slices that extend in a depth direction (the Z-axis in FIGS. 46-38 and 50-52), in the manner described above.

In step S4410, a particular slice corresponding to a desired depth in the depth direction may be selected. As discussed above, an operator may wish to know the thickness of the lingual and buccal plates at a particular depth or depths. For example, as illustrated in FIGS. 53A and 53B, the operator may wish to know the thicknesses at depths $D_1$ and $D_2$, which are within the depth of the tooth cavity. The operator may input one or more desired depths via the input unit 114 (or the display unit 108 if a touchscreen), and the computer system 106 may return a two-dimensional image corresponding to the desired depth, as illustrated in FIG. 53C for a depth $D_1$. Unlike a traditional two-dimensional x-ray image, the two-dimensional image shown in FIG. 53C is substantially parallel to the plane of the x-ray detector 102 at the depth $D_1$, and thus generally perpendicular to the lingual and buccal plates. As such, the thicknesses of the lingual and buccal plates can be determined by direct measurement using the two-dimensional image (S4412).

More particularly, in step S4412, an operator may select two points in the two-dimensional image and the computer system 106 will automatically return the distance between those points in a desired unit. In one embodiment, the operator may draw a line between two points (as illustrated in FIG. 53C) and the computer system 106 will return the distance between the end points of the line. For example, assume an operator enters a depth $D_1$, corresponding to a depth which is roughly one-third of the depth of the tooth cavity shown in FIGS. 52A and 52B (Note: the trabecular region is omitted from FIGS. 52A and 52B for simplicity purposes). The computer system 106 will return and display the two-dimensional image shown in FIG. 53C on a display unit 108. In FIG. 53C, the lingual plate 4204 and the buccal plate 4206 are clearly visible. As shown in FIG. 53C, an operator may draw lines 5302 and 5304 across the lingual plate 4204 and the buccal plate 4206, respectively, and the computer system 106 will calculate and display the length of those lines (5302 and 5304) in order to determine the thicknesses ($T_L$ and $T_B$) of the lingual plate 4204 ($T_L$) and the buccal plate 4206 ($T_B$) at that depth. By redrawing lines 5302 and 5304 at another location, the operator may determine the thicknesses of the lingual plate 4204 and the buccal plate 4206 at that location as well. If the operator wishes to make another thickness measurement at a second depth (e.g., depth D2 shown in FIGS. 53A and 53B), the operator need only provide the tomosynthesis system 100 with the desired depth information via the input unit 114, and the computer system 106 will return a corresponding two-dimensional image at that depth from which the operator can select points or draw a line so as to measure the thicknesses of the lingual plate 4204 ($T_L'$) and the buccal plate 4206 ($T_B'$). Thus, contrary to a traditional x-ray imaging, the above method allows the operator to determine the thicknesses of the lingual and buccal plates at a desired depth, without subjecting the patient to a relatively large dose of radiation, which they may receive from a CBCT scan.

As noted above, the tomosynthesis system 100 may receive guidance from the operator indicating a clinical aspect of interest, which may be the lingual and buccal plates. To aid the operator in identifying the lingual and buccal plates at a particular depth, the computer system 106 may analyze the tomosynthesis stack and automatically segment the anatomical features therein. In other words, the computer system 106 may automatically determine which portion of one or more two-dimensional images correspond to the clinical aspect of interest (i.e., the lingual and buccal plates). In one embodiment, the computer system 106 may use relative attenuation factors, determined from analyzing the plurality of projection images, to discern the presence of one or more objects within the tomosynthesis stack and segment those objects from each other. The computer system 106 may then highlight, outline, or color code those segmented objects and display them on the display unit 108. In one embodiment, the computer system 106, having segmented the lingual and buccal plates from the surrounding objects, may automatically measure the thicknesses of those plates at one or more locations on the two-dimensional image and display those measurements on the display unit 108. In an exemplary embodiment, a user may provide the computer system 106 with information regarding the location of a desired implant and a depth range for the implant. In return the computer system 106 may provide measurements of the plate thicknesses at one or more depths within that range. Of course, this does not preclude the operator from selecting a different set of points, or drawing a different line, at a desired location to measure the thickness of the lingual or buccal plate at that location.

Tracking Motion from Projection Images

Figure 54:
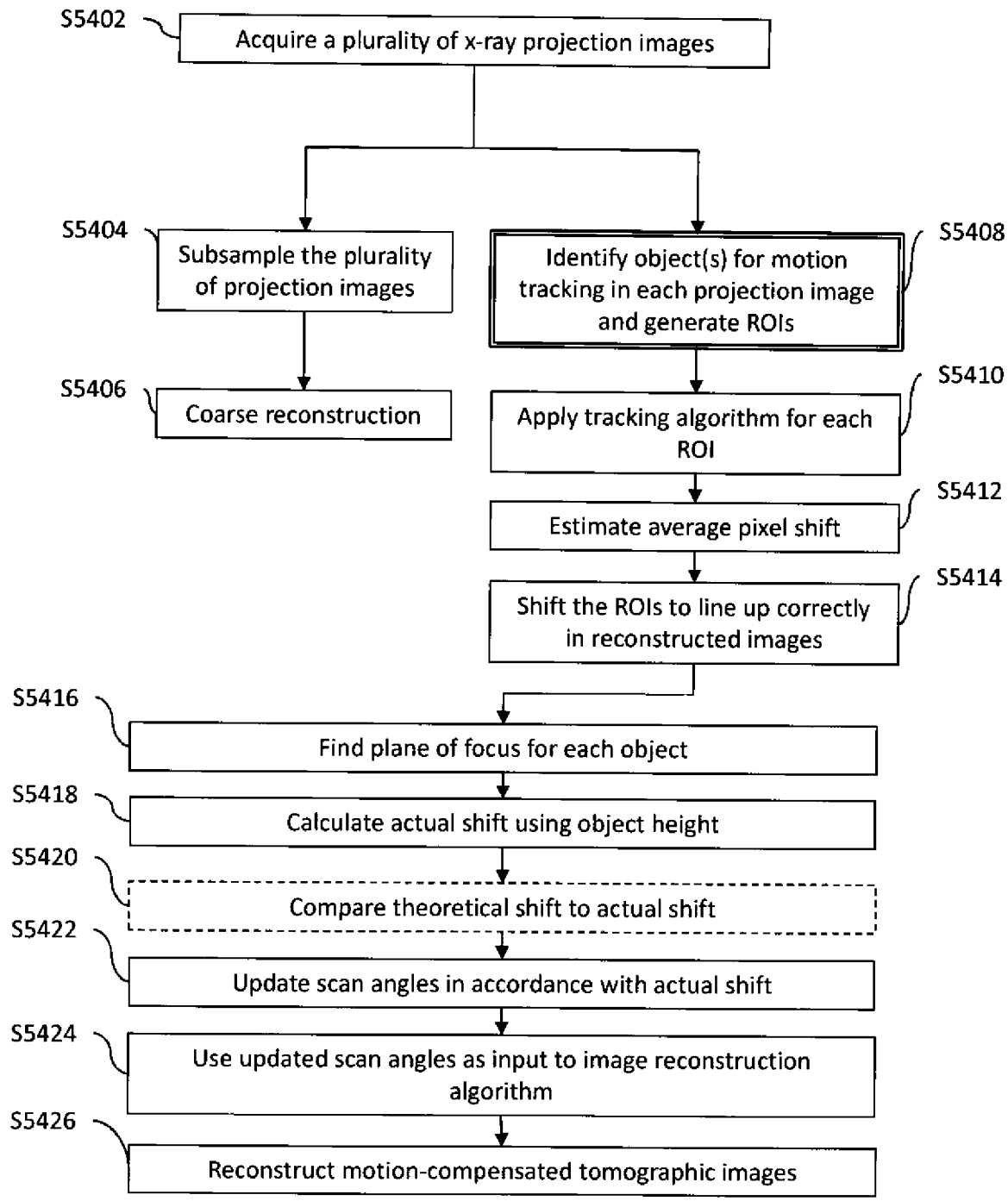
FIG. 54 is a flow diagram illustrating a procedure for tracking motion of an object according to an example embodiment herein.

The intraoral tomosynthesis system 100 will now be further described in conjunction with FIG. 54, which is a flow diagram illustrating a process of tracking motion of one or more objects using a plurality of projection images in an intraoral dataset according to an example embodiment herein. In one example embodiment, the process steps shown in FIG. 54 can be embodied in a control program stored in a non-transitory computer-readable storage medium and loaded into the main memory 232 and/or the secondary memory 234 of the computer system 106 using the removable-storage drive 238, the hard disk drive 236, and/or the communications interface 246. Control logic (software), when executed by the processor 222, causes the computer system 106, and more generally the intraoral tomosynthesis system 100, to perform the procedures described herein.

Prior to starting the process illustrated in FIG. 54, the x-ray detector 102 and x-ray source 104 are first aligned. Typically, the x-ray detector 102 and the x-ray source 104 are manually aligned by a clinician. In that regard, an aiming device may be used to ensure a proper initial alignment. However, relative motion of the x-ray detector 102 and the x-ray source 104 may occur during a scanning operation as a result of one or more factors including, for example, movement of object 50 (e.g., a patient), sub-object 52 (e.g., an object inside the patient), x-ray source 104, and/or x-ray detector 102. FIG. 54 describes an exemplary method for tracking such relative motion.

In Step S5402, the intraoral tomosynthesis system 100 acquires a plurality of projection images of object 50 over a scan angle range 112 (which may be predetermined), including the orthogonal projection image, in the manner described above. For example, the x-ray source 104 is moved by the motorized stage 118 and control circuitry 120 to different positions within the scan angle 112, and the computer system 106 controls the x-ray source 104 to emit x-rays 110 at each position. As discussed above, and shown in FIG. 1A, the x-ray source 104 may translate as well as rotate about a pivot point. In one example embodiment herein, the scan angle 112 ranges from −20° to +20°, with the scanning positions evenly distributed in increments of 0.8° to provide 51 scan angles, including the 0° position, although this example is not limiting. The x-rays 110 then pass through and are attenuated by the object 50 before being projected onto the x-ray detector 102. The x-ray detector 102 converts the x-rays 110 into electrical signals (either directly or indirectly, as described above) and provides the electrical signals to the computer system 106. The computer system 106 processes the electrical signals collected at each scan angle position to acquire the plurality of projection images, each image comprising an array of pixels. The image acquired with the x-ray source 104 at the 0° position is also referred to herein as an orthogonal projection image.

In one example embodiment herein, the color depth of each pixel value of the projection images may be 12-bit grayscale, and the dimensions of the projection images correspond to the standard dental size of the x-ray detector 102, as described above. For example, a Size-2 detector may produce projection images that are approximately 1700×2400 pixels in size, a Size-1 detector may produce projection images that are approximately 1300×2000 pixels in size, and a Size-0 detector may produce projection images that are approximately 1200×1600 pixels in size.

In Step S5402, the computer system 106 generates a sub-sample of projection images from the plurality of projection images obtained in step S5402. The sub-sample of projection images may be stored in, for example, main memory 232 or secondary memory 234. The sub-sample of projection images is for use in a coarse image reconstruction, performed in step S5406. By using a sub-sample of projection images, less computational resources and time are consumed by the image reconstruction process in step S5406. Of course, in an alternate embodiment, step S5404 may be skipped and the reconstruction process in step S5406 may be conducted using all of the projection images obtained in step S5404.

The sub-sample of projection images may include less than all of the projection images obtained in step S5402 (e.g., 25 out of 51 projection images may be included in the sub-sample of projection images). In one embodiment, for example, every other projection image in the plurality of projection images is included in the sub-sample of projection images. Preferably, at least half of the projection images are included in the sub-sample of projection images. Each individual projection image in the sub-sample of the projection images may be further sampled to reduce the number of pixels therein. For example, in one embodiment, half of the pixels in each projection image are filtered out (e.g., every other pixel in the projection image). This further reduces the computational intensity of the reconstruction process in step S5406. Of course, in another embodiment, all of the plurality of projection images may be retained for use in the reconstruction process in step S5406, but the number of pixels in each projection image may be reduced.

In step S5406, image reconstruction is performed using the sub-sample of projection images obtained in step S5404. This image reconstruction is considered a coarse reconstruction because less than all of the projection images and/or pixels are used in the reconstruction process. Computer system 106 may also perform deblurring and other image enhancements, as will be described further herein.

As discussed above, each reconstructed tomosynthesis image slice is comprised of an array of pixels that represent a cross-section of object 50 in a plane that is parallel to the surface of the x-ray detector 102 (the x-y plane in FIG. 1A). The plane is located a certain distance from the x-ray detector 102 in a direction that is orthogonal to the surface of the x-ray detector 102 (the z-axis direction in FIG. 1A).

Each tomosynthesis image slice has a certain thickness along the z-axis that is a function of the reconstruction technique used to create the tomosynthesis image slices and aspects of the geometry of the system 100, including, primarily, the scan angle 112. For example, each tomosynthesis image slice may have a slice thickness of 0.5 mm by virtue of the geometry of the system 100 and the reconstruction technique. The desired location of each tomosynthesis image slice along the z-axis is provided as an input to the reconstruction performed in Step S5406 either as a pre-programmed parameter in computer system 106 or by user input via input unit 114 and/or display unit 108. By example only, the computer system 106 can be instructed to reconstruct, from the plurality of projection images, a first tomosynthesis image slice that is one millimeter (1 mm) away from the surface of x-ray detector 102 along the z-axis, a last tomosynthesis image slice that is fifteen millimeters (15 mm) away from the surface of the x-ray detector 102, and one or more image slices between the first image slice and the last image slice at regular increments along the z-axis of two-hundred micrometers (200 μm), for a total of seventy-one image slices.

Reconstruction of the tomosynthesis image slices in Step S5406 may be performed in accordance with any existing or later developed reconstruction techniques. One exemplary technique which may be used is the shift-and-add technique. The shift-and-add technique utilizes information about the depth of sub-object(s) 52 along the z-axis that is reflected in the parallax captured by the plurality of projection images, as described above. According to this example embodiment, an image slice is reconstructed by first spatially shifting each projection image by an amount that is geometrically related to the distance between the image slice and the tomographic focal spot 122 along the z-axis. The shifted projection images are then averaged together to result in the image slice, where all sub-objects 52 in the plane of the image slice are in focus and sub-objects 52 outside of that plane are out of focus and blurry. This shift-and-add process is repeated for each image slice to be reconstructed. In the case of the image slice corresponding to the x-y plane that includes the focal spot 122, the projection images are averaged together without first shifting because sub-objects 52 are already in focus for that plane.

As mentioned above, a deblurring technique may be used to deblur reconstructed tomosynthesis image slices. In one example embodiment herein, a deblurring technique that substantially reduces or removes blurry, out-of-plane sub-objects from an image slice can be performed in conjunction with the reconstruction technique (whether shift-and-add or another technique). Examples of deblurring techniques that can be employed are, for example, spatial frequency filtering, ectomography, filtered backprojection, selective plane removal, iterative restoration, and matrix inversion tomosynthesis, each of which may be used in Step S5404 to deblur images reconstructed by the shift-and-add reconstruction technique (or another reconstruction technique, if employed).

In another example embodiment herein, Step S5406 also can include the computer system 106 performing further automated image enhancements such as, for example, image sharpening, brightness optimization, and/or contrast optimization, on each reconstructed (and deblurred, where deblurring is performed) image slice in a known manner.

Additionally, in another example embodiment herein, the dimensions, position, and orientation of each image slice reconstructed in Step S5406 are the same as the corresponding characteristics of the orthogonal projection image. Thus, when tomosynthesis image slices (or portions thereof) and the orthogonal projection image are overlaid over one another, corresponding anatomical features appearing in the images will be overlapped and aligned without scaling, rotation, or other transformation of the images.

Figure 55:
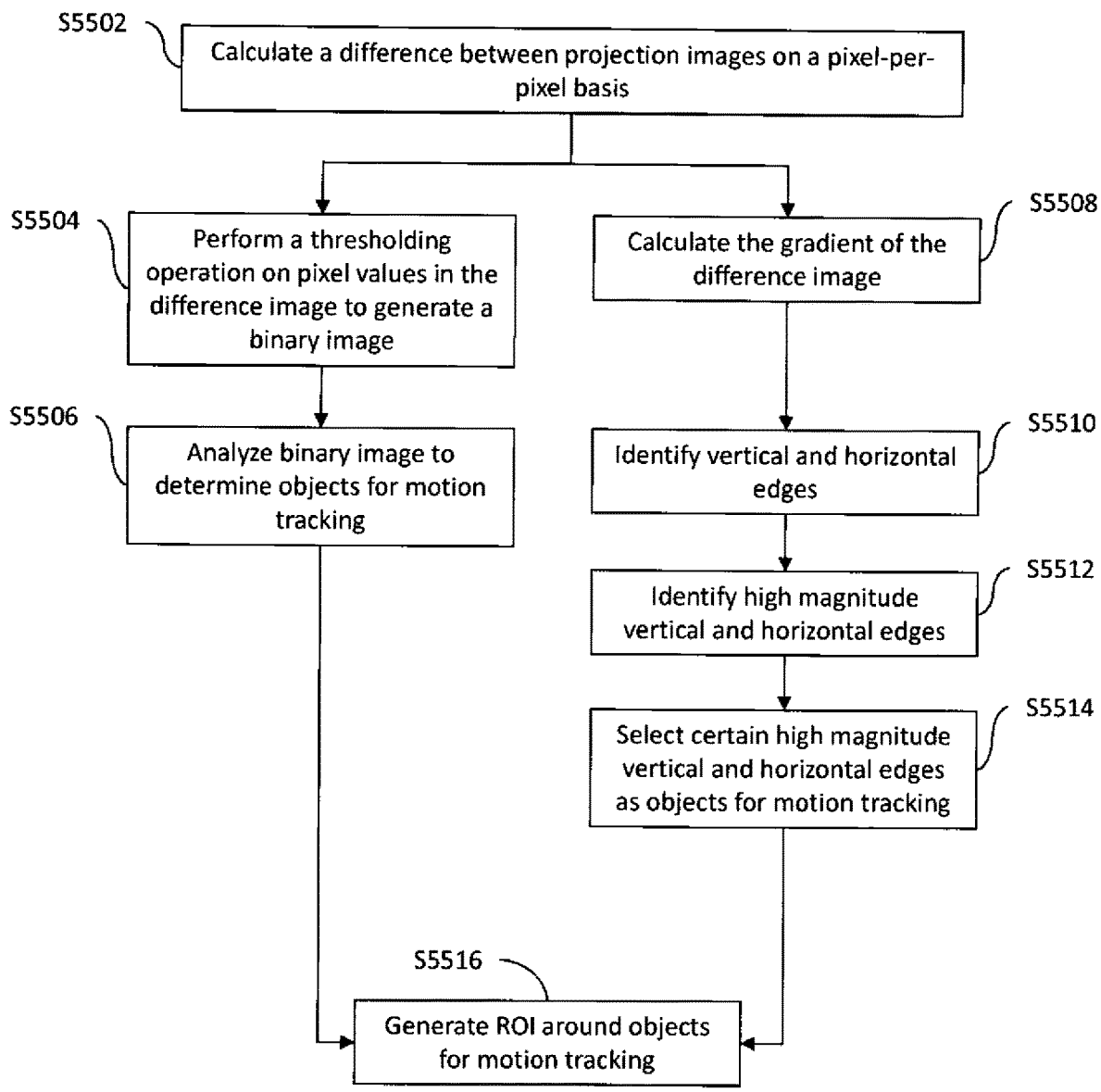
FIG. 55 is a flow diagram illustrating two methods for identifying objects in a projection image.

In Step S5408, the computer system 106 processes the plurality of projection images acquired in step S5402 to identify one or more objects in each projection image that may be appropriate for tracking motion. This process is detailed in FIG. 55.

As noted above, each projection image is comprised of a plurality of pixels, each with an assigned color depth (e.g., 12-bit grayscale). The total number of pixels in each projection image is dependent upon the size of the x-ray detector 102, as discussed above. In a preferred embodiment, each of the projection images acquired in step S5402 has the same number of pixels contained therein. In step S5502, a difference between neighboring projection images is calculated on a pixel-per-pixel basis, as shown in FIGS. 56A-57B.

Figure 56A:
FIG. 56A illustrates an example first projection image of teeth.
Figure 56B:
FIG. 56B illustrates an example second projection image of teeth.
Figure 57A:
FIG. 57A illustrates an example difference image determined from the first projection image of FIG. 56A and the second projection image of FIG. 56B.

FIG. 56A shows a first projection image 5600 recorded at a first scanning position in the scan angle 112. FIG. 56B is a second projection image 5602 recorded at a second scanning position in the scan angle 112. The first and second scanning positions are adjacent to one another in the scan angle 112. FIG. 57A is a difference image 5700, representing the difference between pixel values at the same x and y locations in the first and second projection images. The pixel values in the difference image (representing the difference between the first and second projection images) may be label as a set of values $D_2(x,y)$. While FIG. 57A shows a difference image 5700 corresponding to the first and second projection images, computer system 106 calculates a difference image for each adjacent pair of projection images (that is projection images corresponding to adjacent scanning positions) to create a series difference images with pixel values $D_{ij}(x,y)$.

The difference images calculated in S5502 may be used to identify objects for motion tracking. Alternative methods may be used to identify the objects for motion tracking. For example, a thresholding image method (S5504-S5506) or a gradient segmentation method (S5508-S5514) may be used. Briefly, in the thresholding image method (S5504-S5506), described in further detail below, a difference image 5700 is used to generate a binary image 5700 (see FIG. 57B), which is subsequently analyzed to determine connected segments. One or more of the connected segments (e.g., the four largest connected segments) are identified as objects for motion tracking. The computer system 106 then generates a region of interest (ROI) around the identified objects (S5516).

In the gradient segmentation method (S5508-S5514), described in detail below, a gradient segmentation operation is performed on the difference image 5700 (S5508). The gradient segmentation operation calculates the magnitude and direction of the gradient at each pixel location in the difference image 5700. The computer system 106 isolates the vertical and horizontal edges (S5510), based on the calculated gradient, and identifies the vertical and horizontal edges with a gradient magnitude above a certain magnitude (S5512). Of those vertical and horizontal edges, certain edges are selected as objects for motion tracking (S5514). The computer system 106 then generates a region of interest (ROI) around the identified objects (S5516).

Figure 57B:
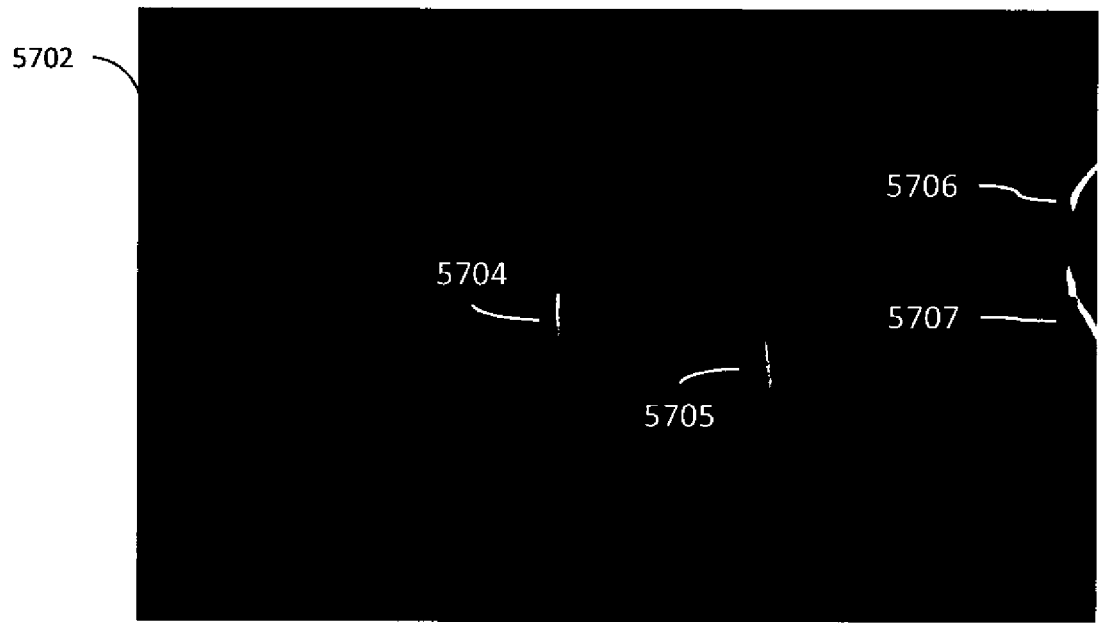
FIG. 57B illustrates an example binary image determined from the difference image of FIG. 57A and four objects identified thereon.

Turning to the thresholding image method, in step S5504 a thresholding operation is performed on the pixel values in the difference image $D_{ij}(x,y)$ to produce a binary image. More specifically, each pixel value in $D_{ij}(x,y)$ is compared to a threshold value. If the pixel value is greater than threshold value, then a pixel value at a corresponding point in a binary image (represented by a series of values $B_{ij}(x,y)$) is set to 1, otherwise the pixel value at the corresponding point is set to 0. In one embodiment, the threshold value may be set as the average pixel value in the difference image, resulting in half of the pixels in the binary image having a value of 1, and the other half having a value of zero. An exemplary binary image 5702 is shown in FIG. 57B.

Once the binary image 5702 is generated in step S5504, the binary image 5702, or more specifically the values $B_{ij}(x,y)$ comprising the binary 5702 image, are analyzed to determine connected segments (step S5506). This may be accomplished by analyzing the binary image 5702 to determine regions where values of "1" are continuously adjacent to one another. The largest connected segments in the binary image (i.e., the longest continuous chain of adjacent values of "1") are then identified by computer system 106, and one or more of those segments are identified as objects for motion tracking. In one embodiment, the computer system 106 identifies the four largest objects as objects for motion tracking; however, more or less objects may be used. As shown in FIG. 57B, the computer system 106 has identified four objects 5704-5707 for motion tracking from the binary image 5702.

Turning to the gradient segmentation method, in step S5508 the gradient of the difference image 5700 is calculated from the values $D_{ij}(x,y)$. The computer system 106 analyzes the direction of the gradient on a pixel level basis to identify vertical and horizontal edges. For example, the computer system 106 analyzes adjacent pixels to determine if the direction of the gradient is substantially vertical or horizontal (e.g., within a range of 10 degrees of either vertical or horizontal). If a pixel falls outside of this range, it is disregarded. If the direction of the gradient is substantially vertical for adjacent pixels, then the adjacent pixels may correspond to a horizontal edge. If the direction of the gradient is substantially horizontal then the adjacent pixels may correspond to a vertical edge. The computer system 106 may determine the presence of a vertical or horizontal edge if the gradient for a minimum number of adjacent pixels is in the horizontal or vertical directions, respectively. In step S5512, the computer system 106 analyzes the identified vertical and horizontal edges to determine the magnitude of the gradient along those edges. In step S5514, the computer system 106 identifies vertical and horizontal edges where the magnitude of the gradient is above a certain threshold. For those vertical and horizontal edges where the magnitude of the gradient is above the threshold, the computer system 106 determines the size of the edges and selects one or more of the largest edges as objects for motion tracking. In one embodiment, edges comprised of 200 or more pixels are used for motion tracking.

Figure 58:
FIG. 58 illustrates an example projection image of teeth and a region of interest indicated thereon for each identified object.

Regardless of whether the objects for motion tracking are determined by the thresholding image method or the gradient segmentation method, once the objects for motion tracking are identified, the computer system 106 automatically generates regions of interest (ROIs) around the objects, in step S5516. For example, FIG. 58 is a projection image where four regions of interest 5801-5804 have been generated around the positions of objects 5704-5707 in FIG. 57B.

After Step S5408 is performed, control passes to step S5410 in which the computer system 106 applies a tracking algorithm for each region of interest. The tracking algorithm is explained in further detail below, with reference to FIG. 59. In one embodiment, one or more processes (e.g., a filtering operation) may be performed prior to executing the tracking algorithm. For example, the pixel values in projection images may be filtered.

FIG. 59 shows two projection images (5902 and 5904) recorded at adjacent scanning positions within the scan angle 112. As shown in FIG. 59, the position of object 5906 is shifted up and to the left in the second projection image 5904. To determine the amount of shift, a region of interest 5908 may be generated over a portion of object 5906 in the first projection image 5902. In one embodiment, the region of interest 5908 may be windowed to reduce edge effects. The computer system 106 then overlays the region of interest 5908 at a first position ($P_1$) in the second projection image 5904, and multiplies the pixels value from the region of interest 5908 in the first projection image 5902 ($P_{ROI}(x, y)$) by the pixels values corresponding to the area of the second projection image which the region of interest 5908 overlays ($P_{5902-P1}(x,y)$), respectively, and then sums the result. The sum is a cross-correlation function. The summation (i.e., the cross-correlation function) is recorded and stored in memory 232 or 234. The region of interest 5908 is then translated to a second position and another multiplication is calculated and the corresponding summation is recorded. In one embodiment, the region of interest 5908 is translated by a unit of one pixel in either the x or y direction. However, the region of interest 5908 may be translated by a greater amount to reduce computational time. The region of interest is thus translated across the second projection image 5904, and a series of summations (of the plurality of individual multiplications) are recorded. When the region of interest 5908 is overlaid with the same portion of the object 5906 that the region of interest 5908 corresponds to in the first projection image 5902 (at an alignment position $P_A$), the resulting multiplication produce a relatively large result, and thus the summation of those multiplications is also relatively large and identifiable by the computer system 106. In other words, the computer system 106 determines the translation for which the cross-correlation function is a maximum as the alignment position. For example, assume the projection image is comprised of nine pixels arranged in a 3×3 array, with the center pixel having a value of pure white (e.g., 255) and the remaining pixels have a value of pure black (i.e., 0). If the ROI is the center pixel, then the pixel value for the ROI is also pure white (e.g., 255). Note, since the ROI only contains one pixel, there is only one multiplication operation and no summation operation in this example. The result of a multiplication of the pixel value corresponding to the ROI (255) by any pixel other than the center pixel (0) is 0. When the pixel value corresponding to the ROI (255) is multiplied by the center pixel (255), however, the result is 65,025. This result is a maximum among the calculations and thus corresponds to an alignment position. Since the translations of the ROI are approximately known, the possible alignment position is restricted to a set of possible alignment positions. In another embodiment, the cross-correlation function may be determined by applying a fourier transform technique.

With the alignment position and the position of the region of interest in the first projection image known, the computer system 106 may determine how much shift occurred in both the x and y directions between the first projection image 5902 and the second projection image 5904.

As noted above, the computer system 106 may track the motion of more than one object. As such, the above tracking algorithm may be performed for each ROI corresponding to the objects for motion tracking (e.g., objects 5704-5707 in FIG. 57B). If the motion of more than one object is tracked, then (in step S5412) an average pixel shift may be determined from the calculated shifts for each ROI, with the average pixel shift along the x and y axes calculated separately.

Through the above-described process, an average shift for each ROI between two projections images may be determined. This process may be used to calculate the average pixel shift for ROIs between projection images obtained at adjacent scanning positions across the scan angle 112. For example, an average ROI shift ($ROI_{12}$) between a first projection image (corresponding to scan angle of 20°) and a second projection image (corresponding to scan angle of 19.2°) may be calculated, as well as an average ROI shift ($ROI_{23}$) between the second projection image (corresponding to the scan angle of 19.2°) and a third projection image (corresponding to a scan angle of 18.6°).

Once all of the ROI shifts are calculated across the scan angle 112, it is necessary to shift each ROI in each projection image by the cumulative shift amount in order for all of the ROIs to align in the tomosynthesis stack.

The cumulative shift is the sum of the ROI shifts that occur in the x and y direction between the orthogonal imaging position (corresponding to 0° in the scan angle, e.g. $SP_{0x}$) and a particular scanning position. For example, assume there are 51 scanning positions within the scan angle 112. The cumulative ROI (along the x-axis) shift for scanning position $SP_{-2}$ (corresponding one end of the scan angle 112), is the sum of the cumulative ROI shifts between scanning positions $SP_{-25x}$, $SP_{-24x}$, $SP_{-23x}$, ..., to $SP_{-1x}$. In a similar manner, the cumulative ROI shift for scanning position $SP_{-13}$, along the x axis is the sum of the cumulative shifts between scanning positions $SP_{-13}$, $SP_{-12x}$, ..., to $SP_{-1x}$. In step S5414, the computer system 106 shifts each ROI in each projection image by the appropriate cumulative shift amount.

After Step S5414, control passes to Step S5416 which takes as input the coarse tomographic image slices reconstructed in step S5404 and the shifted ROIs of step S5414. In step S5416, the computer system 106 determines the plane of focus for each object used for motion tracking using, for example, the focus technique described above. In one embodiment, computer system 106 evaluates how in focus the ROI is for each slice in the tomosynthesis stack and assigns a corresponding focus factor. The computer system 106 determines the tomosynthesis slice with at least a local maximum focus factor which corresponds to the plane in which the object is in focus. By determining the plane in which the object is in focus, the location of the object relative to the surface of x-ray detector 102 and the x-ray source 104 can be determined. In other words, the distance in the imaging direction (the z-axis) from tomosynthesis image slice that contains a high-focus image of the object to the x-ray source 104 is used as the distance in the imaging direction from the object(s) for motion tracking to the x-ray source 104. With this information, the actual shift amount for the x-ray source between two projection images corresponding to adjacent scanning positions may be determined (step S5418).

It should be noted that the same object may not be used to determine the actual shift amount for each pair of projection images. An object used for motion tracking between a first and second projection image, may not be the same object used for motion tracking between a second and third projection image. If a different object is used, then the distance from the x-ray source 104 to the different object in the imaging direction will likely change. Nevertheless, the above process takes this fact into consideration, and thus produces actual shift amounts for the x-ray source between the projection images regardless of whether the same object is used for motion tracking or not.

In step S5420, the actual shift amounts for the x-ray source may be compared to theoretical shift amounts. As mentioned above, motion of the patient, the x-ray detector 102, and/or the x-ray source 104, may cause the actual shift amounts to depart from the theoretical shift amount, which assumes that the system geometry (the spatial relationship between the patient, x-ray detector 102, and x-ray source 104) is constant. However, this comparison is not necessary to generate motion-compensated tomographic images, and is therefore an optional step.

In step S5422, the scan angles (which are one input for the reconstruction algorithm) are updated based on the actual shift amounts for the x-ray source 104 for motion tracking. Corrections to the scan angles may be calculated based on the actual shift amounts and the pixel size (in mm) for a given x-ray detector 102. The updated scan angles are then input into the reconstruction algorithm (step S5424). The computer system 106 then performs image reconstruction on the motion-compensated projection images (step S5426).

The motion-compensated tomographic images may then be displayed on display unit 108. In one example embodiment herein, the displaying can be performed as to show the entire stack, or one or more selected image slices of the stack, using display unit 108, and interactive controls (e.g. via display unit 108 and/or input device 114) enable a user to select between those two options, and to select one or more image slices for display, and also to select one or more particular regions of interest in the image(s) for display (whether in zoom or non-zoom, or reduced fashion). In a further example embodiment, stack controls are provided and can include a scroll bar, which enables the user to manually select which image slice is displayed on the display unit 108, and/or can include selectable control items, such as play, pause, skip forward, and skip backward, (not shown) to enable the user to control automatic display of the tomosynthesis stack, as a cine loop for example, on the display unit 108.

As will be appreciated by those of skill in the relevant art(s) in view of this description, the example aspects described herein can be implemented using a single computer or using a computer system that includes multiple computers each programmed with control logic to perform various of the above-described functions.

The various embodiments described above have been presented by way of example and not limitation. It will be apparent to persons skilled in the relevant art(s) that various changes in form and detail can be made therein (e.g., different hardware, communications protocols, and the like) without departing from the spirit and scope of the present invention. Thus, the present invention should not be limited by any of the above-described exemplary embodiments, but should be defined only in accordance with the following claims and their equivalents.

In addition, it should be understood that the attached drawings, which highlight functionality described herein, are presented as illustrative examples. The architecture of the present invention is sufficiently flexible and configurable, such that it can be utilized and navigated in ways other than that shown in the drawings.

Moreover, the example embodiments described herein are not limited to intraoral tomosynthesis imaging. The example embodiments described herein can be used to perform scans of other anatomical regions. In addition, one or more of the above techniques may also be applied to tomography in general (including CT and CBCT).

Further, the purpose of the Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present invention in any way. It is also to be understood that the procedures recited in the claims need not be performed in the order presented.

What is claimed is:

1. A method comprising:
   measuring three-dimensional anatomical distances in a stack of tomosynthesis images by:
   stacking each image of the tomosynthesis images on top of or below another image in a direction orthogonal to a plane of an illumination detector;
   accepting selection of a plurality of points, placed via an input unit on a plurality of images in the stack of tomosynthesis images, the plurality of points are selected to include at least a first point placed on a first image and a second point placed on a second image;
   providing markers for the plurality selected points, the markers for the first and second points are provided to be distinguishable from each other and the marker for the first point is provided to be visible on a displayed image of the stack of tomosynthesis images during a scroll through the stack of tomosynthesis images even when said displayed image is different from the first image;
   generating a 3D vector having a magnitude and a direction based on at least the first and second points the generating being responsive to the accepting,
   wherein each image in the stack is in a respective plane along a z-axis, and
   wherein a z-coordinate of the respective plane corresponds to a distance from the plane to the surface of the illumination detector.

2. The method according to claim 1, further comprising displaying the 3D vector and the plurality of images corresponding to the first and second points.

3. The method according to claim 2, wherein the vector is displayed in a 3D coordinate space.

4. The method according to claim 3, further comprising rotating the 3D coordinate space.

5. The method according to claim 1, further comprising dynamically updating the 3D vector of the first and second points selected via the input unit responsive to a change in a position of the first or second point.

6. The method according to claim 1, further comprising preprocessing the tomosynthesis images for noise reduction and edge enhancement.

7. The method according to claim 1, further comprising calculating a distance and 3D vector length between the selected points.

8. The method according to claim 7, further comprising displaying the calculated distance and 3D vector length.

9. A system comprising at least one processor operable to:
   measure three-dimensional anatomical distances in a stack of tomosynthesis images by:
   stacking each image of the tomosynthesis images on top of or below another image in a direction orthogonal to a plane of an illumination detector;

accepting selection of a plurality of points, placed via an input unit, on a plurality of images in the stack of tomosynthesis images, the plurality of points are selected to include at least a first point placed on a first image and a second point placed on a second image;

providing markers for the plurality selected points, the markers for the first and second points are provided to be distinguishable from each other and the marker for the first point is provided to be visible on a displayed image of the stack of tomosynthesis images during a scroll through the stack of tomosynthesis images even when said displayed image is different from the first image;

generating a 3D vector based on at least the first and second points, the generating being responsive to the accepting;

wherein each image in the stack is in a respective plane along a z-axis, and wherein a z-coordinate of the respective plane corresponds to a distance from the plane to the surface of the illumination detector.

10. The system according to claim 9, wherein the processor is further operable to display the 3D vector and the plurality of images corresponding to the first and second points.

11. The system according to claim 10, wherein the vector is displayed in a 3D coordinate space.

12. The system according to claim 11, wherein the processor is further operable to rotate the 3D coordinate space.

13. The system according to claim 9, wherein the processor is further operable to dynamically update the 3D vector of the first and second points selected via the input unit responsive to a change in a position of the first or second point.

14. The system according to claim 9, wherein the processor is further operable to preprocess the tomosynthesis images for noise reduction and edge enhancement.

15. The system according to claim 9, wherein the processor is further operable to calculate a distance and 3D vector length between the selected points.

16. The system according to claim 15, wherein the processor is further operable to provide the calculated distance and 3D vector length to an output device for presentation to a user.

17. A non-transitory computer-readable storage medium storing a program which, when executed by a computer system, causes the computer system to:

measure three-dimensional anatomical distances in a stack of tomosynthesis images by:

stacking each image of the tomosynthesis images on top of or below another image in a direction orthogonal to a plane of an illumination detector;

accepting selection of a plurality of points, placed via an input unit on a plurality of images in the stack of tomosynthesis images, the plurality of points are selected to include at least a first point placed on a first image and a second point placed on a second image;

providing markers for the plurality selected points, the markers for the first and second points are provided to be distinguishable from each other and the marker for the first point is provided to be visible on a displayed image of the stack of tomosynthesis images during a scroll through the stack of tomosynthesis images even when said displayed image is different from the first image;

generating a 3D vector based on at least the first and second points, the generating being responsive to the accepting, wherein each image in the stack is in a respective plane along a z-axis, and wherein a z-coordinate of the respective plane corresponds to a distance from the plane to the surface of an illumination detector.

18. The storage medium according to claim 17, wherein the program further causes the computer system to display the 3D vector and the plurality of images corresponding to the selected points.

* * * * *